(12) United States Patent
Almo et al.

(10) Patent No.: US 11,226,339 B2
(45) Date of Patent: Jan. 18, 2022

(54) METHODS FOR HIGH THROUGHPUT RECEPTOR:LIGAND IDENTIFICATION

(71) Applicant: Albert Einstein College of Medicine, Bronx, NY (US)

(72) Inventors: Steven C. Almo, Pelham, NY (US); Ronald D. Seidel, III, Larchmont, NY (US); Brandan S. Hillerich, Larchmont, NY (US); Sarah C. Garrett-Thomson, New York, NY (US); James D. Love, New York, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 0 days.

(21) Appl. No.: 16/044,608

(22) Filed: Jul. 25, 2018

(65) Prior Publication Data
US 2020/0011875 A1 Jan. 9, 2020

Related U.S. Application Data

(63) Continuation of application No. 14/649,176, filed as application No. PCT/US2013/073275 on Dec. 5, 2013, now Pat. No. 10,048,271.

(60) Provisional application No. 61/735,791, filed on Dec. 11, 2012, provisional application No. 61/833,588, filed on Jun. 11, 2013.

(51) Int. Cl.
*G01N 33/68* (2006.01)
*G01N 15/14* (2006.01)
*G01N 33/543* (2006.01)

(52) U.S. Cl.
CPC ......... *G01N 33/6845* (2013.01); *G01N 15/14* (2013.01); *G01N 33/54326* (2013.01); *G01N 33/54366* (2013.01); *G01N 2015/149* (2013.01)

(58) Field of Classification Search
None
See application file for complete search history.

(56) References Cited

U.S. PATENT DOCUMENTS

| | | | |
|---|---|---|---|
| 5,635,363 A | 6/1997 | Altman et al. |
| 6,197,302 B1 | 3/2001 | Hirsch et al. |
| 6,211,342 B1 | 4/2001 | Hirsch et al. |
| 6,268,411 B1 | 7/2001 | Schneck et al. |
| 6,696,304 B1 | 2/2004 | Davies |
| 7,098,306 B2 | 8/2006 | Economou et al. |
| 7,186,804 B2 | 3/2007 | Gillies et al. |
| 7,670,595 B2 | 3/2010 | Gillies et al. |
| 8,992,937 B2 | 3/2015 | Hansen et al. |
| 9,284,349 B2 | 3/2016 | Tsunoda et al. |
| 9,359,424 B2 | 6/2016 | Le Maoult et al. |
| 9,494,588 B2 | 11/2016 | Springer et al. |
| 2002/0006664 A1 | 1/2002 | Sabatini |
| 2002/0031520 A1 | 3/2002 | Economou et al. |
| 2004/0038349 A1 | 2/2004 | Hilbert et al. |
| 2004/0161817 A1 | 8/2004 | Benton et al. |
| 2004/0209363 A1 | 10/2004 | Watts et al. |
| 2005/0003431 A1 | 1/2005 | Wucherpfennig et al. |
| 2005/0009012 A1 | 1/2005 | Holzberg et al. |
| 2005/0100926 A1 | 5/2005 | Chen et al. |
| 2006/0034865 A1 | 2/2006 | Hildebrand et al. |
| 2006/0269515 A1 | 11/2006 | Denis-Mize et al. |
| 2007/0036752 A1 | 2/2007 | Gillies et al. |
| 2007/0148162 A1 | 6/2007 | Bhardwaj et al. |
| 2007/0286843 A1 | 12/2007 | Pfizenmaier et al. |
| 2008/0199485 A1 | 8/2008 | Kundig et al. |
| 2008/0219947 A1 | 9/2008 | Linette et al. |
| 2008/0269070 A1 | 10/2008 | Ramseier et al. |
| 2010/0159594 A1 | 6/2010 | Hansen et al. |
| 2011/0002956 A1 | 1/2011 | Weiner et al. |
| 2011/0268737 A1 | 11/2011 | Favier et al. |
| 2011/0318380 A1 | 12/2011 | Brix et al. |
| 2012/0003220 A1 | 1/2012 | Chen |
| 2012/0121577 A1 | 5/2012 | Weidanz et al. |
| 2012/0177595 A1 | 7/2012 | Wong et al. |
| 2012/0264161 A1 | 10/2012 | Scholler et al. |
| 2013/0017199 A1 | 1/2013 | Langermann |
| 2013/0149305 A1 | 6/2013 | Ostrand-Rosenberg |
| 2014/0046026 A1 | 2/2014 | Garcia et al. |
| 2014/0162293 A1 | 6/2014 | Springer et al. |
| 2014/0242077 A1 | 8/2014 | Choi et al. |
| 2014/0348832 A1 | 11/2014 | Zhu et al. |
| 2015/0071987 A1 | 3/2015 | Selvaraj |
| 2015/0224186 A1 | 8/2015 | Nakagawa |
| 2015/0232532 A1 | 8/2015 | Ostrand-Rosenberg |
| 2015/0374788 A1 | 12/2015 | Paulsen et al. |
| 2016/0011204 A1 | 1/2016 | Almo et al. |
| 2016/0083477 A1 | 3/2016 | Klein et al. |

(Continued)

FOREIGN PATENT DOCUMENTS

CN 1791675 A 6/2006
CN 101384621 A 3/2009

(Continued)

OTHER PUBLICATIONS

Lázár-Molnár et al., "The PD-1/PD-L costimulatory pathway critically affects host resistance to the pathogenic fungus Histoplasma capsulatum" 105(7) Proceedings of the National Academy of Sciences USA 2658-2663 (Year: 2008).*

(Continued)

*Primary Examiner* — Nancy J Leith
(74) *Attorney, Agent, or Firm* — Fox Rothschild LLP

(57) ABSTRACT

Methods and systems for high-throughput Identification of receptor:ligand interactions are provided. Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

7 Claims, 26 Drawing Sheets
Specification includes a Sequence Listing.

(56) References Cited

U.S. PATENT DOCUMENTS

| | | |
|---|---|---|
| 2016/0090407 A1 | 3/2016 | Hosse et al. |
| 2016/0114019 A1 | 4/2016 | Li et al. |
| 2016/0152725 A1 | 6/2016 | Cheung et al. |
| 2016/0175397 A1 | 6/2016 | Umana et al. |
| 2016/0304580 A1 | 10/2016 | Ellmark et al. |
| 2016/0362465 A1 | 12/2016 | Nishimura et al. |
| 2017/0044229 A1 | 2/2017 | Garcia et al. |
| 2017/0058015 A1 | 3/2017 | Seidel, III et al. |
| 2017/0334951 A1 | 11/2017 | O'Reilly et al. |
| 2018/0064795 A1 | 3/2018 | Sugiyama |
| 2018/0208626 A1 | 7/2018 | Scheinberg et al. |

FOREIGN PATENT DOCUMENTS

| | | | |
|---|---|---|---|
| CN | 101418309 A | 4/2009 | |
| CN | 101448951 A | 6/2009 | |
| CN | 101688213 A | 3/2010 | |
| JP | 2000515363 A | 11/2000 | |
| JP | 2004501364 A | 1/2004 | |
| JP | 2005506058 A | 3/2005 | |
| JP | 2007530021 A | 11/2007 | |
| JP | 2009537175 A | 10/2009 | |
| JP | 2010524506 A | 7/2010 | |
| JP | 2012516854 A | 7/2012 | |
| JP | 2015537043 A | 12/2015 | |
| WO | 97/028191 A1 | 8/1997 | |
| WO | 2001/090747 A2 | 11/2001 | |
| WO | 2002/072631 A2 | 9/2002 | |
| WO | 2002/087613 A1 | 11/2002 | |
| WO | 2002093129 A2 | 11/2002 | |
| WO | 2002/102299 A2 | 12/2002 | |
| WO | 2004/029197 A2 | 4/2004 | |
| WO | 2004111190 A2 | 12/2004 | |
| WO | 2007/136778 A2 | 11/2007 | |
| WO | 2008/019888 A2 | 2/2008 | |
| WO | 2008/116468 A2 | 10/2008 | |
| WO | 2008/134461 A2 | 11/2008 | |
| WO | 2010/037395 A2 | 4/2010 | |
| WO | 2010/091122 A1 | 8/2010 | |
| WO | 2011/066342 A2 | 6/2011 | |
| WO | 2011/066389 A1 | 6/2011 | |
| WO | 2012/127464 A2 | 9/2012 | |
| WO | 2012/175508 A1 | 12/2012 | |
| WO | 2013003761 A1 | 1/2013 | |
| WO | WO 2013/079174 A1 * | 6/2013 | ........... A61K 39/395 |
| WO | 2014/083004 A1 | 6/2014 | |
| WO | 2014/093118 A1 | 6/2014 | |
| WO | 2015/112541 A2 | 7/2015 | |
| WO | 2015/164815 A1 | 10/2015 | |
| WO | 2015195531 A2 | 12/2015 | |
| WO | 2016/014428 A1 | 1/2016 | |
| WO | 2016000619 A1 | 1/2016 | |
| WO | 2016/025642 A1 | 2/2016 | |
| WO | 2016/029043 A1 | 2/2016 | |
| WO | 2016/030350 A1 | 3/2016 | |
| WO | 2016/164937 A2 | 10/2016 | |
| WO | 2016/168771 A2 | 10/2016 | |
| WO | 2017/023779 A1 | 2/2017 | |
| WO | 2017/059819 A1 | 4/2017 | |
| WO | 2017/151818 A2 | 9/2017 | |
| WO | 2017/151940 A2 | 9/2017 | |
| WO | 2017/201131 A1 | 11/2017 | |
| WO | 2019/051126 A1 | 3/2019 | |

OTHER PUBLICATIONS

Baldi et al., "Recombinant protein production by large-scale transient gene expression in mammalian cells: state of the art and future perspectives" 29 Biotechnology Letters 677-684 (2007).

Hug et al., "T-cadherin is a receptor for hexameric and high-molecular weight forms of Acrp30/adiponectin" 101 (28) Proceedings of the National Academy of Sciences USA 10308-10313 (2004).

Miao et al., "Transient expression of fluorescent fusion proteins in protoplasts of suspension cultured cells" 2(10) Nature Protocols 2348-2353 (2007).

Ziauddin et al., "Microarrays of cells expressing defined cDNAs," Nature, vol. 411, pp. 107-110, May 3, 2001.

Buonaguro, et al.; "Translating Tumor Antigens into Cancer Vaccines"; Clinical and Vaccine Immunology; vol. 18, No. 1, pp. 23-24 (Jan. 2011).

Carey, et al.; "A soluble divalent class I MHC/IgG1 fusion protein activates CD8+ T cells in vivo"; Clinical Immunology; vol. 116, pp. 65-76 (2005).

Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).

De Charette, et al.; "Turning tumour cells into antigen presenting cells: The next step to improve cancer immunotherapy?"; European Journal of Cancer; vol. 68, pp. 134-147 (2016).

GENEBANK:NP_001009066.1; 2 pages (2003).

HLA Nomenclature; "HLA Alleles Numbers"; 2 pages (Mar. 17, 2015).

Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).

Karin, et al.; "Reversal of Experimental Autoimmune Encephalomyelitis by a Soluble Peptide Variant of a Myelin Basic Protein Epitope: T Cell Receptor Antagonism and Reduction of Interferon ? and Tumor Necrosis Factor ? Production"; J. Exp. Med.; vol. 180, pp. 2227-2237 (Dec. 1994).

Lazar-Molnar, et al.; "Crystal structure of the complex between programmed death-1 (PD-1) and its ligand PD-L2"; PNAS; vol. 105, No. 30, pp. 10483-10488 (Jul. 29, 2008).

Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).

Medina, et al.; "PD-1 Pathway Inhibitors: Immuno-Onology Agents for Restoring Anititumor Immune Responses"; Pharmacotherapy; vol. 36, No. 3, pp. 317-334 (2016).

Motz, et al.; "Tumor Endothelium Fast Establishes a Selective Immune Barrier Promoting Tolerance in Tumors"; Nat. Med.; vol. 20, No. 6, pp. 607-615 (Jun. 2014).

Ochoa-Garay, et al.; "The Ability of Peptides to Induce Cytotoxic T Cells In Vitro Does Not Strongly Correlate with Their Affinity for the H-2Ld Molecule: Implications for Vaccine Design and Immunotherapy"; Molecular Immunology; vol. 34, No. 3, pp. 273-281 (1997).

Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).

Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).

Repana, et al.; "The Network of Cancer Genes (NCG): a comprehensive catalogue of known and candidate cancer genes from cancer sequencing screens"; Genome Biology; vol. 20, No. 1, 12 pages (2019).

Rocha-Zavaleta, et al.; "Interleukin-2 (IL-2) receptor-?? signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).

Schmittnaegel, et al.; "A New Class of Bifunctional Major Histocompatibility Class I Antibody Fusion Molecules to Redirect CD8 T Cells"; Molecular Cancer Therapeutics; vol. 15, No. 9, pp. 2130-2142 (Sep. 2016).

Schumacher, et al.; "Neoantigens in cancer immunotherapy"; Science; vol. 348, No. 6230, pp. 69-74 (Apr. 2, 2015).

Stamper, et al.; "Crystal structure of the B7-1/CTLA-4 complex that inhibits human immune responses"; Nature; vol. 410, pp. 608-611 (Mar. 29, 2001).

Tham, et al.; "Activation of antigen-specific T cells by artificial cell constructs having immobilized multimeric peptide-class I com-

(56) References Cited

OTHER PUBLICATIONS plexes and recombinant B7-Fc proteins"; Journal of Immunological Methods; vol. 249, pp. 111-119 (2001).
Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).
White, et al.; "Soluble Class I MHC with ?2-MicroglobulinCovalently Linked Peptides: Specific Binding to a T Cell Hybridoma"; J Immunol; vol. 162, pp. 2671-2676 (1999).
Zheng, et al.; "B7-CTLA4 interaction enhances both production of antitumor cytotoxic T lymphocytes and resistance to tumor challenge"; PNAS; vol. 95, pp. 6284-6289 (May 1998).
Lin, et al.; "The PD-1/PD-L1 complex resembles the antigen-binding Fv domains of antibodies and T cell receptors"; PNAS; vol. 105, No. 8, pp. 3011-3016 (Feb. 2008).
Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).
Ramani, et al.; "A secreted protein microarray platform for extracellular protein interaction discovery"; Analytical Biochemistry; vol. 420, pp. 127-138 (2012).
Reche, et al.; "Sequence Variability Analysis of Human Class I and Class II MHC Molecules: Functional and Structural Correlates of Amino Acid Polymorphisms"; Journal of Molecular Biology; vol. 331, No. 3, pp. 623-641 (Aug. 15, 2003).
Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).
Shah, et al.; "Bio-layer Interferometry for Measuring Kinetics of Protein-protein Interactions and Allosteric Ligand Effects"; Journal of Visualized Experiments; vol. 84, 11 pages (2014).
Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).
Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).
Stadinski, et al.; "Diabetogenic T cells recognize insulin bound to IAg7 in an unexpected, weakly binding register"; PNAS; vol. 107, No. 24, pp. 10978-10983 (Jun. 15, 2010).
Taube, et al.; "Lentivirus Display: Stable Expression of Human Antibodies on the Surface of Human Cells and Virus Particles"; PLoS One; vol. 3, No. 9, 12 pages (Sep. 2008).
Torres, et al.; "The immunoglobulin constant region contributes to affinity and specificity"; Trends in Immunology; vol. 29, No. 2, pp. 91-97 (Jan. 10, 2008).
Toukam, et al.; "Targeting Antibody Responses to the Membrane Proximal External Region of the Envelope Glycoprotein of Human Immunodeficiency Virus"; PLoS One; vol. 7, No. 5, 10 pages (May 2012).
Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).
Venkatakrishnan, et al.; "The Structural Biology of Hepatitis B Virus: Form and Function"; Annu. Rev. Virol.; vol. 3, No. 1, pp. 429-451 (Sep. 29, 2016).
Whitehead, et al.; "Optimization of affinity, specificity and function of designed influenza inhibitors using deep sequencing"; Nat. Biotechnol.; vol. 30, No. 6, pp. 543-548 (Apr. 29, 2013).
Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).

Wu, et al.; "Simultaneous targeting of multiple disease mediators by a dual-variable-domain immunoglobulin"; Nature Biotechnology; 25: p. 1290-1297 (2007).
Xu, et al.; "Cytokine release syndrome in cancer immunotherapy with chimeric antigen receptor engineered T cells"; Cancer Letters; 343(2): p. 172-178 (2014).
Azuma, et al.; "B7-H1 is a ubiquitous antiapoptotic receptor on cancer cells"; Immunobiology; vol. 111, No. 7, pp. 3635-3643 (Apr. 1, 2008).
Crawford, et al.; "Use of baculovirus MHC/ peptide display libraries to characterize T-cell receptor ligands"; Immunological Reviews; vol. 210, pp. 156-170 (2006).
Wang, et al.; "Using a baculovirus display library to identify MHC class I mimotopes"; PNAS; vol. 102, No. 7, pp. 2476-2481 (Feb. 15, 2005).
Cafri, et al.; "Development of novel genetic cancer vaccines based on membrane-attached ?2 microglobulin"; Ann. N.Y. Acad. Sci.; vol. 1283, pp. 87-90 (2013).
Hansen, et al.; "Phage display of peptide/major histocompatibility class I complexes"; Eur. J. Immunol.; vol. 31, pp. 32-38 (2001).
Kim, et al.; "Single chain MHC I trimer-based DNA vaccines for protection against Listeria monocytogenes infection"; Vaccine; vol. 30, pp. 2178-2186 (2012).
Margalit, et al.; "Induction of Antitumor Immunity by CTL Epitopes Genetically Linked to Membrane-Anchored ?2-Microglobulin"; The Journal of Immunology; vol. 176, pp. 217-224 (2006).
Doussal, et al.; "Phage display of peptide /major histocompatibility complex"; Journal of Immunological Methods; vol. 241, pp. 147-158 (2000).
Greten, et al.; "Peptide-?2-microglobulin-MHC fusion molecules bind antigen-specific T cells and can be used for multivalent MHC-Ig complexes"; Journal of Immunological Methods; vol. 271, pp. 125-135 (2002).
Obermann, et al.; "Peptide-?2-microglobulin-major histocompatibility complex expressing cells are potent antigen-presenting cells that can generate specific T cells"; Immunology; vol. 122, pp. 90-97 (2007).
McAllister, et al.; "Adaptation of Recombinant HEK-293 Cells to Growth in Serum Free Suspension"; Animal Cell Technology: Products from Cells, Cells as Products; 3 pages (1999).
Wen, et al.; "Construction and screening of an antigen-derived peptide library displayed on yeast cell surface for CD4+ T cell epitope identification"; Methods Mol. Biol.; vol. 1061, pp. 245-264 (2013).
Engelhard; "Structure of peptides associated with MHC class I molecules"; Current Opinion in Immunology; vol. 6, pp. 13-23 (1994).
Guo, et al.; "Different length peptides bind to HLA-Aw68 similarly at their ends but bulge out in the middle"; Nature; vol. 360, pp. 364-366 (Nov. 26, 1992).
Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).
Hugues, et al.; "Generation and use of alternative multimers of peptide/MHC complexes"; Journal of Immunological Methods; vol. 268, pp. 83-92 (2002).
Krautwurst, et al.; "Identification of Ligands for Olfactory Receptors by Functional Expression of a Receptor Library"; Cell; vol. 95, pp. 917-926 (Dec. 23, 1998).
Muller, et al.; "Random peptide libraries displayed on adeno-associated virus to select for targeted gene therapy vectors"; Nature Biotechnology; vol. 21, No. 9, pp. 1040-1046 (Sep. 2003).
Crisci, et al.; "Virus-like particles: The new frontier of vaccines for animal viral infections"; Veterinary Immunology and Immunopathology; vol. 148, pp. 211-225 (2012).
Kushnir, et al.; "Virus-like particles as a highly efficient vaccine platform: Diversity of targets and production systems and advances in clinical development"; Vaccine; vol. 31, pp. 58-83 (2012).
Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).

(56) References Cited

OTHER PUBLICATIONS

Aina, et al.; "Identification of novel targeting peptides for human ovarian cancer cells using 'one-bead one-compound' combinatorial libraries"; Mol. Cancer Ther.; vol. 4, No. 5, 8 pages (May 2005).
Arduin, et al.; "Highly reduced binding to high and low affinity mouse Fc gamma receptors by L234A/L235A and N297A Fc mutations engineered into mouse IgG2a"; Molecular Immunology; vol. 63, pp. 456-463 (2015).
Bowers, et al.; "Coupling mammalian cell surface display with somatic hypermutation for the discovery and maturation of human antibodies"; PNAS; vol. 108, No. 51, pp. 20455-20460 (Dec. 20, 2011).
Cebecauer, et al.; "Soluble MHC-Peptide Complexes Induce Rapid Death of CD8+ CTL"; The Journal of Immunology; vol. 174, pp. 6809-6819 (2005).
Center for Disease Control and Prevention; "How Many Cancers Are Linked with HPV Each Year?"; 4 pages (2016).
Chames, et al.; "Bispecific antibodies for cancer therapy; The light at the end of the tunnel?" mAbs; vol. 1, No. 6, pp. 539-547 (Nov.-Dec. 2009).
Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).
Czajkowsky, et al.; "Fc-fusion proteins: new developments and future perspectives"; EMBO Mol. Med.; vol. 4, pp. 1015-1028 (2012).
Das, et al.; "Generation of murine tumor cell lines deficient in MHC molecule surface expression using the CRISPR/Cas9 system"; PLoS One; vol. 12, No. 3, 19 pages (Mar. 16, 2017).
Desmond, et al.; "A systematic review of T-cell epitopes in hepatitis B virus: identification, genotypic variation and relevance to antiviral therapeutics"; Antiviral Therapy; vol. 13, pp. 161-175 (2008).
Dimasi, et al.; "The design and characterization of oligospecific antibodies for simultaneous targeting of multiple disease mediators"; Journal of Molecular Biology; 393(3): p. 672-692 (2009).
Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).
Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).
Goel, et al.; "Plasticity within the Antigen-Combining Site May Manifest as Molecufar Mimicry in the Humoral Immune Response"; The Journal of Immunology; vol. 173, pp. 7358-7367 (2004).
Gough, et al.; "The HLA Region and Autoimmune Disease: Associations and Mechanisms of Action"; Current Genomics; vol. 8, pp. 453-465 (2007).
Grupp, et al.; "Adoptive Cellular Therapy"; Curr Top Microbiol Immunol.; 344: p. 149-172 (2011).
Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).
Karaki, et al.; "Is There Still Room for Cancer Vaccines at the Era of Checkpoint Inhibitors"; Vaccines; vol. 4, No. 37, 24 pages (2016).
Khan, et al.; "Adjustable Locks and Flexible Keys: Plasticity of Epitope-Paratope Interactions in Germline Antibodies"; The Journal of Immunology; vol. 192, pp. 5398-5405 (2014).
Lenormand, et al.; "HLA-DQA2 and HLA-DQB2 Genes Are Specifically Expressed in Human Langerhans Cells and Encode a New HLA Class II Molecule"; The Journal of Immunology; vol. 199, No. 8, pp. 3903-3911 (Apr. 15, 2012).
Liu, et al.; "Attaining High Transient Titers in CHO Cells"; Genetic Engineering & Biotechnology News; vol. 35, No. 17, 3 pages (Oct. 1, 2015).
Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).
Mallone, et al.; "T Cell Recognition of Autoantigens in Human Type 1 Diabetes: Clinical Perspectives"; Clinical and Developmental Immunology; vol. 2011, 16 pages (2011).
Mizukoshi, et al.; "Identification of ?-fetoprotein-derived peptides recognized by cytotoxic T lymphocytes in HLA-A24+ patients with hepatocellular carcinoma"; Int. J. Cancer; vol. 118, pp. 1194-1204 (2006).
Mott, et al.; "The Solution Structure of the F42A Mutant of Human Interleukin 2"; J. Mol. Biol.; vol. 247, pp. 979-994 (1995).
Naidoo, et al.; "Toxicities of the anti-PD-1 and anti-PD-L1 immune checkpoint antibodies"; Annals of Oncology; vol. 26, pp. 2375-2391 (2015).
Nielsen, et al.; "MHC Class II epitope predictive algorithms"; Immunology; vol. 130, pp. 319-328 (2010).
Oates, et al.; "ImmTACs: Novel bi-specific agents for targeted cancer therapy"; OncoImmunology; vol. 2, No. 2, 3 pages (Feb. 2013).
Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).
Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, pp. 21181-21187 (1995).
Ponstingl, et al.; "The Rule of Antibody Structure: The Primary Structure of a Monoclonal IgG1 Immunoglobulin (Myeloma Protein Nie)"; Hoppe Seylers Z Physiol Chem.; vol. 357, No. 11, pp. 1571-1604 (Nov. 1976). [English translation of Abstract Only].
Poosarla, et al.; "Computational De Novo Design of Antibodies Binding to a Peptide With High Affinity"; Biotechnology & Bioengineering; vol. 114, No. 6, pp. 1331-1342 (Jun. 2017).
Wang, et al.; "Molecular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).
Chinese Office Action dated Apr. 16, 2021, in related Chinese Application No. 201811139644.3, 16 pages.
GENBANK:AEV43323.1; "Fc IgG1 heavy chain constant region, partial [*Homo sapiens*]"; 2 pages (Jul. 25, 2016).
Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).
Strohl; "Optimization of Fc-mediated effector functions of monoclonal antibodies"; Current Opinion in Biotechnology; vol. 20, pp. 685-691 (2009).

* cited by examiner

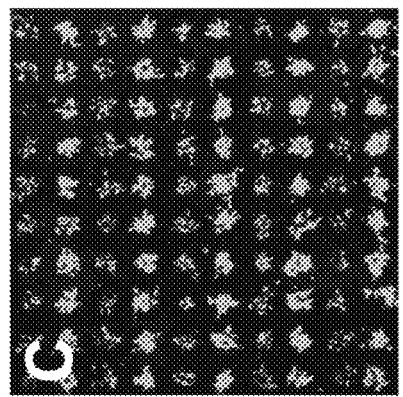
Fig. 4C
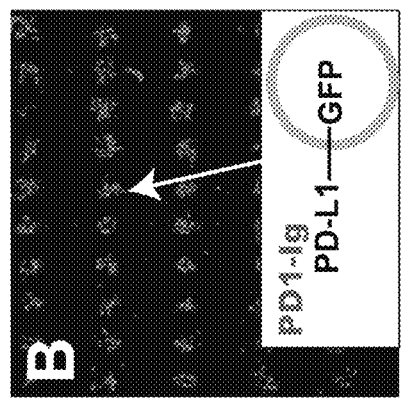
Fig. 4B
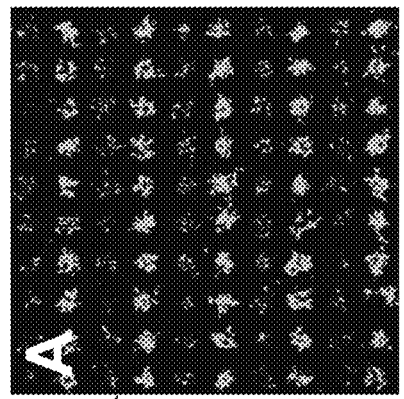
Fig. 4A
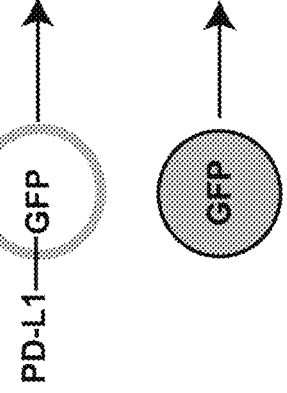

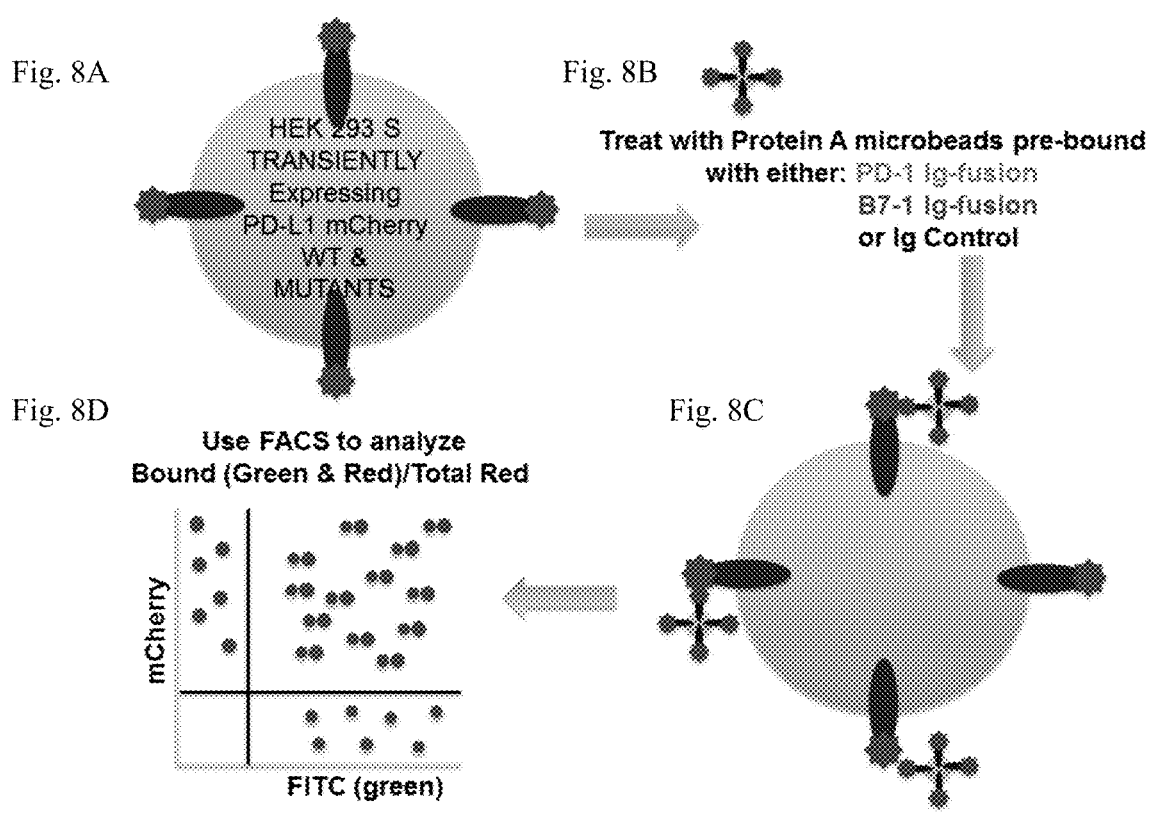

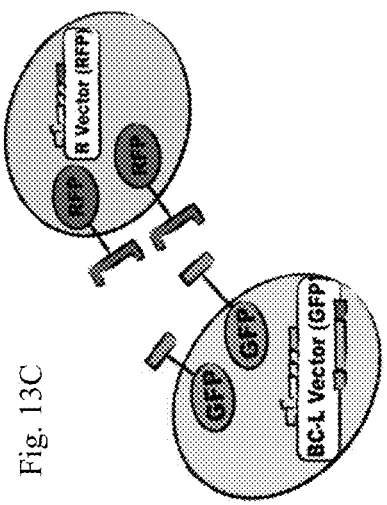
Fig. 13A
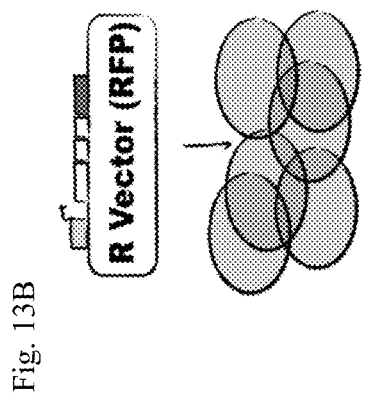
Fig. 13B
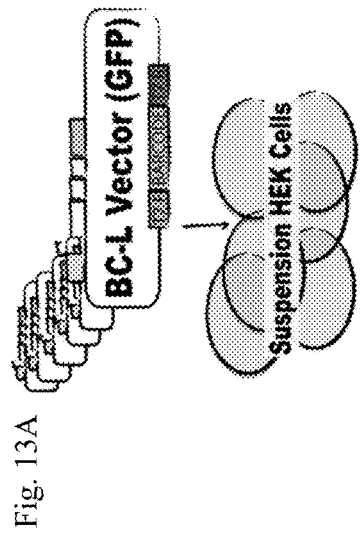
Fig. 13C
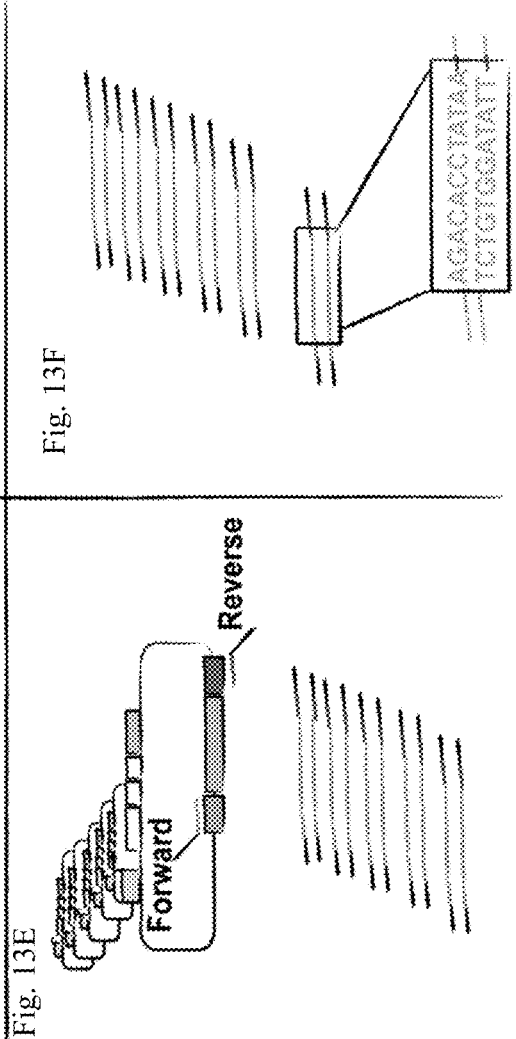
Fig. 13D
Fig. 13E
Fig. 13F
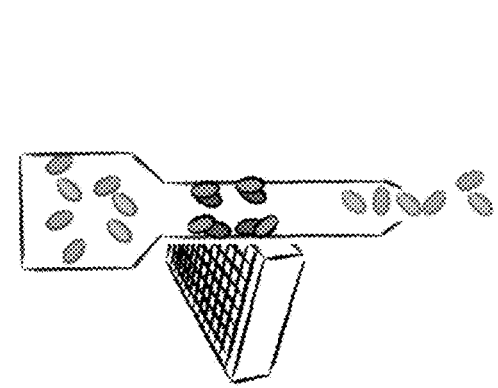

Fig. 15A
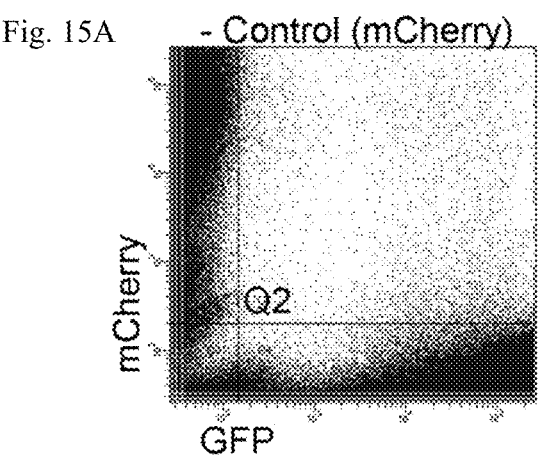
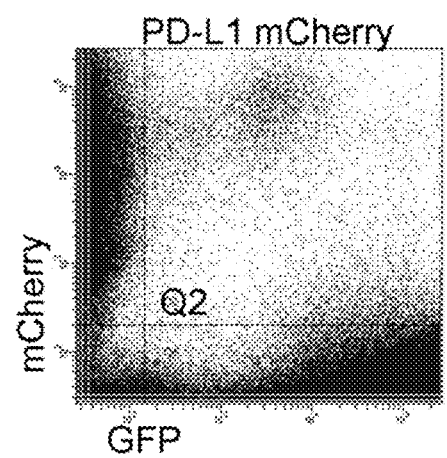
Fig. 15B
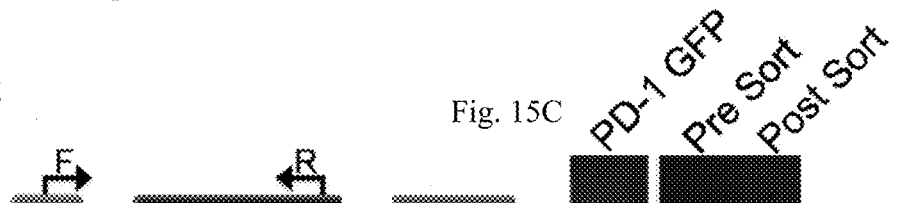
Fig. 15C
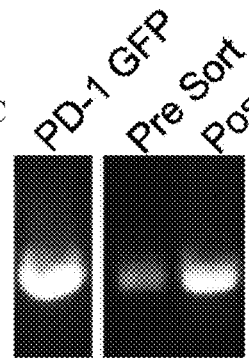

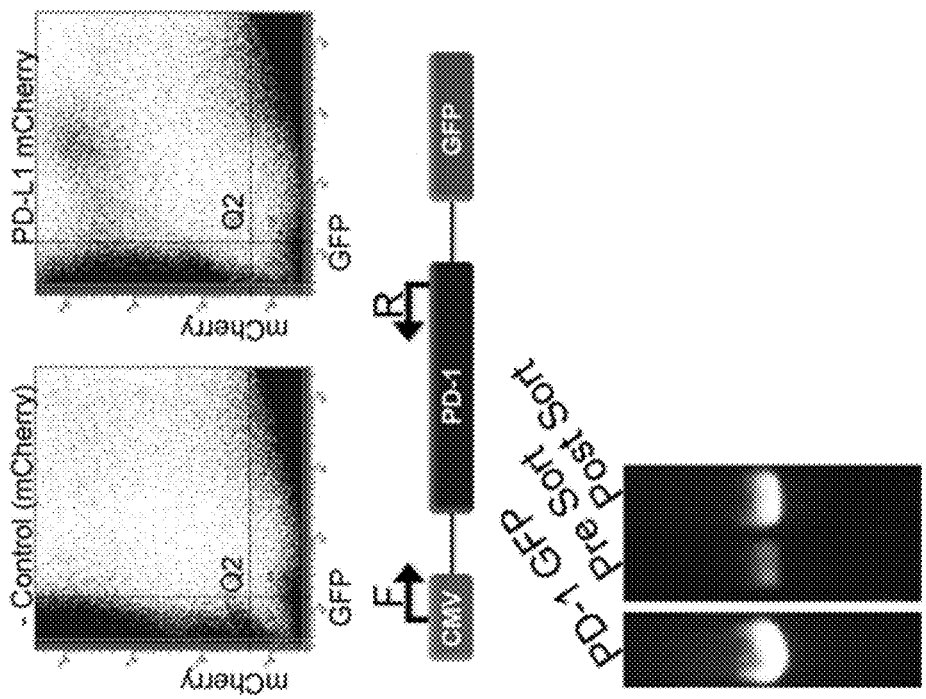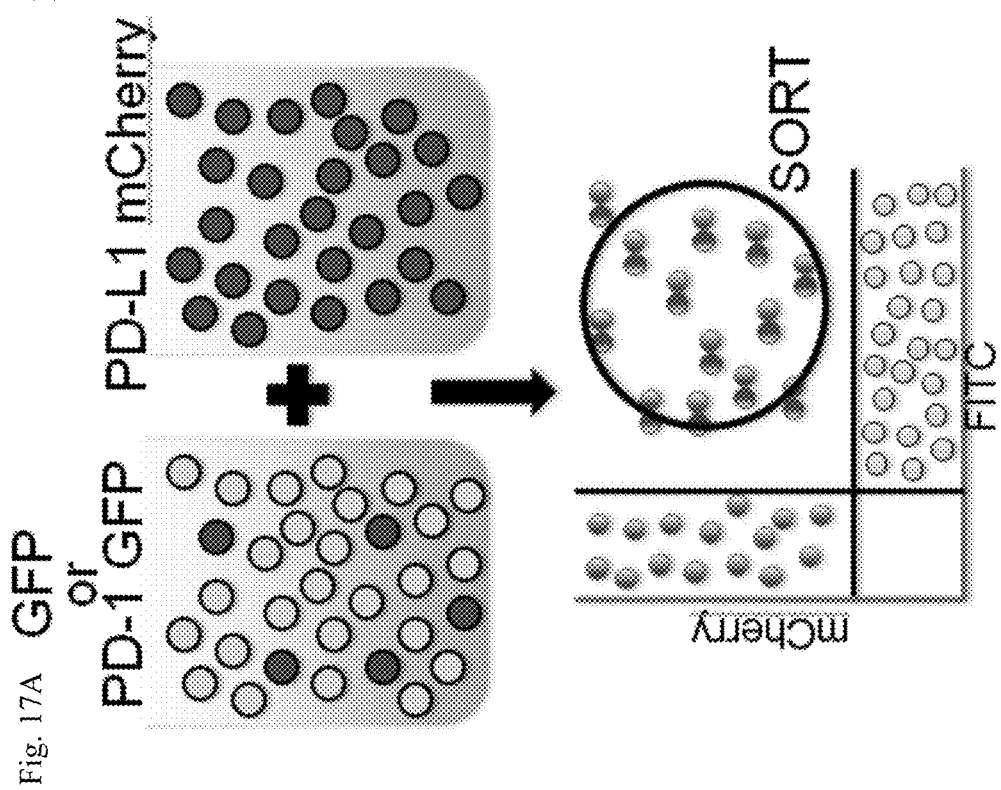
Fig. 17A
Fig. 17B
Fig. 17C
Fig. 17D

Fig. 23A

| Sample | $1.0\times10^6$ cells/mL | $0.5\times10^6$ cells/mL | $0.2\times10^6$ cells/mL | $1.0\times10^6$ cells/mL | $0.5\times10^6$ cells/mL | $0.2\times10^6$ cells/mL |
|---|---|---|---|---|---|---|
| Untransfected | A01 | B05 | C09 | E01 | F05 | G09 |
| GFP Alone | A02 | B06 | C10 | E02 | F06 | G10 |
| mCherry Alone | A03 | B07 | C11 | E03 | F07 | G11 |
| PD-1 GFP Alone | A04 | B08 | C12 | E04 | F08 | G12 |
| PD-L1 mCherry Alone | A05 | B09 | D01 | E05 | F09 | H01 |
| CD200R GFP Alone | A06 | B10 | D02 | E06 | F10 | H02 |
| CD200 mCherry Alone | A07 | B11 | D03 | E07 | F11 | H03 |
| "Cell-Cell" GFP & mCherry | A08 | B12 | D04 | E08 | F12 | H04 |
| "Cell-Cell" GFP & PD-L1 mCherry | A09 | C01 | D05 | E09 | G01 | H05 |
| "Cell-Cell" GFP & CD200 mCherry | A10 | C02 | D06 | E10 | G02 | H06 |
| "Cell-Cell" mCherry & PD-1 GFP | A11 | C03 | D07 | E11 | G03 | H07 |
| "Cell-Cell" mCherry & CD200R GFP | A12 | C04 | D08 | E12 | G04 | H08 |
| "Cell-Cell" CD200R GFP & PD-L1 mCherry | C01 | C05 | D09 | F01 | G05 | H09 |
| "Cell-Cell" PD-1 GFP & CD200 mCherry | B02 | C06 | D10 | F02 | G06 | H10 |
| "Cell-Cell" PD-1 GFP & PD-L1 mCherry | B03 | C07 | D11 | F03 | G07 | H11 |
| "Cell-Cell" CD200R GFP & CD200 mCherry | B04 | C08 | D12 | F04 | G08 | H12 |

```
SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Asp Tyr Lys Asp Asp Asp Asp Lys
1               5

<210> SEQ ID NO 2
<211> LENGTH: 19
<212> TYPE: DNA
<213> ORGANISM: Artificial Sequence
<220> FEATURE:
<223> OTHER INFORMATION: Synthetic sequence

<400> SEQUENCE: 2
gtcatgcaat cgatcgatc                                                  19

<210> SEQ ID NO 3
<211> LENGTH: 360
<212> TYPE: DNA
<213> ORGANISM: Artificial Sequence
<220> FEATURE:
<223> OTHER INFORMATION: Synthetic nucleic acid

<400> SEQUENCE: 3
ctacgggcgt ttactatcac ggctccaaag gacttgtacg tggtggagta tggcagcaac      60
gtcacgatgg agtgcagatt ccctgtagaa cgggagctgg acctgcttgc gttagtggtg     120
tactgggaaa aggaagatga gcaagtgatt cagtttgtgg caggagagga ggaccttaag     180
```

```
cctcagcaca gcaacttcag ggggagagcc tcgctgccaa aggaccagct tttgaaggga      240
aatgctgccc ttcagatcac agacgtcaag ctgcaggacg caggcgttta ctgctgcata      300
atcagctacg gtggtgcgga ctacaagcga atcacgctga aagtcaatgc cccataccgc      360

<210> SEQ ID NO 4
<211> LENGTH: 120
<212> TYPE: PRT
<213> ORGANISM: Artificial Sequence
<220> FEATURE:
<223> OTHER INFORMATION: Synthetic peptide

<400> SEQUENCE: 4

Leu Arg Ala Phe Thr Ile Thr Ala Pro Lys Asp Leu Tyr Val Val Glu
1               5                   10                  15

Tyr Gly Ser Asn Val Thr Met Glu Cys Arg Phe Pro Val Glu Arg Glu
            20                  25                  30

Leu Asp Leu Leu Ala Leu Val Val Tyr Trp Glu Lys Glu Asp Glu Gln
        35                  40                  45

Val Ile Gln Phe Val Ala Gly Glu Glu Asp Leu Lys Pro Gln His Ser
    50                  55                  60

Asn Phe Arg Gly Arg Ala Ser Leu Pro Lys Asp Gln Leu Leu Lys Gly
65                  70                  75                  80

Asn Ala Ala Leu Gln Ile Thr Asp Val Lys Leu Gln Asp Ala Gly Val
                85                  90                  95

Tyr Cys Cys Ile Ile Ser Tyr Gly Gly Ala Asp Tyr Lys Arg Ile Thr
            100                 105                 110

Leu Lys Val Asn Ala Pro Tyr Arg
        115                 120

<210> SEQ ID NO 5
<211> LENGTH: 12
<212> TYPE: DNA
<213> ORGANISM: Artificial Sequence
<220> FEATURE:
<223> OTHER INFORMATION: Synthetic sequence

<400> SEQUENCE: 5
agacacctat aa                                                           12

<210> SEQ ID NO 6
<211> LENGTH: 12
<212> TYPE: DNA
<213> ORGANISM: Artificial Sequence
<220> FEATURE:
<223> OTHER INFORMATION: Synthetic sequence

<400> SEQUENCE: 6
ttataggtgt ct                                                           12
```

METHODS FOR HIGH THROUGHPUT RECEPTOR:LIGAND IDENTIFICATION

CROSS-REFERENCE TO RELATED APPLICATIONS

This application is a continuation of U.S. patent application Ser. No. 14/649,176, filed Jun. 2, 2015, which is a U.S. national stage entry under 35 U.S.C. § 371 of PCT International Patent Application No. PCT/US2013/073275, filed Dec. 5, 2013, which claims benefit of U.S. Provisional Application No. 61/735,791, filed Dec. 11, 2012, and U.S. Provisional Application No. 61/833,588, filed Jun. 11, 2013, the contents of each of which are hereby incorporated by reference.

INCORPORATION BY REFERENCE OF SEQUENCE LISTING PROVIDED AS A TEXT FILE

A Sequence Listing is provided herewith as a text file, "96700-2621_ST25.txt" created on Jul. 25, 2018 and having a size of 2,933 bytes. The contents of the text file are incorporated by reference herein in their entirety.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Cell surface receptors and adhesion molecules are the gatekeepers of cellular function, including developmental, morphogenetic and environmental processes central to normal physiology and pathology. These molecules are prime therapeutic targets. The high-resolution structural characterization of these complexes defines the chemical and physical determinants underlying receptor:ligand specificity, affinity, oligomeric state, valency and overall architectural features that are important for the integration of these interactions and their associated signaling pathways into overall cellular physiology. All of these features are critical for understanding the fundamental mechanisms that drive complex cellular processes and provide unique opportunities for therapeutic intervention. Unfortunately, at present, a systematic structural characterization of these crucial complexes (i.e., structural genomics of the Secretome) is an unrealistic goal, as many, if not most, receptor:ligand pairs remain undefined and thus cannot be structurally characterized.

The present invention addresses this need by providing technologies for the efficient and systematic identification of the repertoire of receptor:ligand interactions relevant to human physiology, disease and medicine.

SUMMARY OF THE INVENTION

A cell microarray is provided comprising: (i) a first plurality of cells transformed so as to expres a first predetermined heterologous secreted protein, heterologous membrane protein or heterologous cell surface protein and a first fluorescent protein and (ii) at least a second plurality of cells transformed so as to express a second predetermined heterologous secreted protein or a second heterologous protein and a second fluorescent protein, wherein the first and second plurality of cells are adhered to a solid surface of the microarray, and wherein the first and second plurality of cells are in spatially distinct locations on the solid surface.

A cell microarray is provided comprising: (i) a first plurality of cells transformed so as to express (a) a first predetermined heterologous protein and (b) a first fluorescent protein and (ii) at least a second plurality of cells transformed so as to express (a) a second predetermined heterologous protein and (b) a second fluorescent protein, wherein the first and second plurality of cells are adhered to a solid surface of the microarray, and wherein the first and second plurality of cells are in spatially distinct locations on the solid surface.

A process is provided for making a cell microarray as described herein, comprising affixing a first plurality of expression constructs encoding the first heterologous protein and the fluorescent protein on a solid surface of a microarray and affixing at least a second plurality of expression constructs encoding the second heterologous protein and the second fluorescent protein on the solid surface of the microarray on the solid surface in a spatially distinct location different from the affixed first plurality of expression constructs, and contacting the expression constructs with a plurality of cells under conditions comprising the presence of a transfection agent, so as to permit the cells to adhere to the solid surface and for transfection to occur of at least a portion of the cells in each spatially distinct location with the respective expression constructs.

A method is also provided for determining if a candidate protein or peptide binds to a second protein or peptide, the method comprising expressing the second protein as a heterologous protein of the cell microarray described herein, and contacting the cell microarray with the candidate protein or peptide, wherein the candidate protein or peptide has affixed thereto a third fluorescent protein or peptide, washing the cell microarray contacted with the candidate protein or peptide so as to remove unbound candidate protein or peptide, and determining if there is any candidate protein or peptide bound to the cell microarray after washing, wherein the presence of candidate protein or peptide bound to the cell microarray after washing in a first spatial location corresponding to cells transformed with a first heterologous protein indicates that the candidate protein or peptide binds to that first heterologous protein, and wherein the absence of candidate protein or peptide bound to the cell microarray in the first spatial location after washing indicates that the candidate protein or peptide does not bind to that heterologous protein.

Also provided is a system comprising (i) a microarray solid surface and a suspension-adapted cell line transformed so as to express on a cell-surface thereof a candidate ligand protein or peptide and a first C-terminal cytoplasmic-expressing fluorescent protein and (ii) at least a) a second plurality of cells transformed so as to express a predetermined heterologous protein on the cell surface thereof and a second fluorescent protein, or b) a plurality of microbeads having affixed to the surface thereof the heterologous protein and having affixed a second fluorescent protein, wherein a) or b) is affixed to the microarray solid surface. A system is also provided as above, mutatis mutandis, wherein the candidate ligand protein or peptide is expressed on the second plurality of transformed cells or plurality of microbeads, and the heterologous protein is expressed on a cell-surface of a transformed suspension-adapted cell line.

A method for determining if a candidate ligand protein or peptide binds to a second protein or peptide, the method comprising expressing the candidate ligand protein or peptide and first fluorescent protein in the suspension-adapted cell line plurality of the instant system, and contacting the plurality with a) the second plurality of cells transformed so as to express the heterologous protein and a second fluorescent protein, or b) the plurality of microbeads having affixed to the surface thereof the heterologous protein and second fluorescent protein, and washing to remove unbound candidate ligand protein or peptide, and identifying by FACS analysis cells that show co-localization of both the first and second fluorescent protein, wherein cells showing co-localization of both the first and second fluorescent protein in a spatially distinct location indicates that the first protein or peptide is bound to the heterologous protein corresponding that spatially distinct location.

A system is provided comprising a first plurality of suspension-adapted cell line cells transformed with a vector so as to express on a cell-surface thereof a first heterologous protein and to express a first cytoplasmic-expressing fluorescent protein and wherein the vector comprises a unique predetermined 15-35 nucleotide sequence for the first heterologous protein, the unique sequence capable of being primed by one or more universal primer(s) and a second plurality of suspension-adapted cell line cells transformed with a second vector so as to express on a cell-surface thereof a second heterologous protein and to express a first cytoplasmic-expressing fluorescent protein and wherein the second vector comprises a different unique predetermined 15-35 nucleotide sequence for the second heterologous protein, and (i) one or more further pluralities of suspension-adapted cell line cells transformed so as to express on a cell-surface thereof a candidate ligand protein or peptide and to express a second fluorescent protein, which second suspension-adapted cell line comprises a stably-expressed peptide cell-surface epitope, or (ii) a plurality of magnetic microbeads having affixed to the surface thereof a candidate ligand protein or peptide and having affixed a second fluorescent protein.

A method is also provided for determining if a candidate ligand protein or peptide binds to a second predetermined protein comprising expressing the second predetermined protein as a heterologous protein of the instant system and contacting with the candidate ligand protein or peptide of the (i) one or more further pluralities of suspension-adapted cell line cells transformed so as to express on a cell-surface thereof a candidate ligand protein or peptide and to express a second fluorescent protein, which second suspension-adapted cell line comprises a stably-expressed peptide cell-surface epitope, or of (ii) the plurality of magnetic microbeads having affixed to the surface thereof a candidate ligand protein or peptide and having affixed a second fluorescent protein; separating by magnetic attraction any of the first plurality of suspension-adapted cell line
cells bound to one or more of the second plurality of cells or to the plurality of magnetic microbeads;
obtaining DNA from such separated cell-cell or cell-microbead conjugates and amplifying, using the universal primers, the unique sequence if present in the DNA;
sequencing copies of the unique sequence to confirm its presence;
comparing the unique sequence(s) so identified against a database correlating the unique predetermined 15-35 nucleotide sequence with specific heterologous protein or peptide,
and thereby identifying any heterologous protein or peptide bind so correlated,
thereby identifying a specific heterologous protein or peptide as binding to the candidate protein or peptide.

A system comprising (i) a first plurality of suspension-adapted cell line cells, wherein cells of the plurality are transformed with a vector so as to (a) express on a cell-surface thereof a heterologous protein and (b) express a first cytoplasmic-expressing fluorescent protein, and wherein the vector comprises a predetermined 15-35 nucleotide sequence unique for the heterologous protein expressed, such that the first plurality of suspension-adapted cell line cells expresses at least two different types of first heterologous protein, and (ii) a second plurality of suspension-adapted cell line cells transformed with a second vector so as to express on a cell-surface thereof a second heterologous protein and to express a second cytoplasmic-expressing fluorescent protein, wherein the second plurality of suspension-adapted cells expresses a single type of second heterologous protein. In an embodiment, any individual cell of the first plurality of cells expresses only one heterologous protein on the cell surface thereof. In an embodiment, none of the different types of first heterologous proteins of the first plurality have same sequence as second heterologous protein of the second plurality.

Also provided is a method for determining if a candidate ligand protein or peptide binds to second protein or peptide comprising expressing the candidate ligand protein or peptide as a first heterologous protein of the first plurality of cells in the system as described herein and expressing the second protein or peptide as a second heterologous protein in the systems as described herein under conditions permitting the first heterologous protein to bind to the second heterologous protein and, optionally, washing to remove any unbound first heterologous protein, then recovering cells with co-localization of both the first and second heterologous protein, obtaining nucleic acid from the recovered cells and sequencing the nucleic acid to identify the unique 15-35 nucleotide sequence contained therein so as to identify the candidate ligand protein or peptide corresponding to the unique 15-35 nucleotide that has bound the second protein or peptide.

Also provided is a method for determining the effect of a predetermined amino acid residue of a first protein on binding of the first protein to a second protein, the method comprising expressing the proteins mutated with one or more point mutations relative to the first protein as the plurality of different types of heterologous proteins in the first suspension-adapted cell line plurality of the systems described herein, and contacting the plurality with the second protein in the form of the second heterologous protein of the second plurality of cells of the systems described herein transformed so as to express the second protein and the second fluorescent protein, and recovering cells that show co-localization of both the first and second fluorescent protein, obtaining nucleic acid from the recovered cells and sequencing the nucleic acid to identify the unique 15-35 nucleotide sequence contained therein so as to identify the first protein that has bound the second protein or peptide, and comparing the level of protein that has bound the second protein or peptide to a predetermined reference level,
wherein a level of protein that has bound the second protein or peptide in excess of the predetermined reference level indicates that the residue or residues as mutated in the protein enhance first protein binding to the second protein, and wherein a level of protein that has bound the second protein or peptide below the predetermined reference level indicates that the residue or residues as mutated in the protein inhibit first protein binding to the second protein.

Also provided is a system comprising (i) a first plurality of suspension-adapted cell line cells transformed with a vector so as to express on a cell-surface thereof a first heterologous candidate ligand protein or peptide and to express a first cytoplasmic-expressing fluorescent protein and a second plurality of suspension-adapted cell line cells transformed with a second vector so as to express on a cell-surface thereof a second heterologous candidate ligand protein or peptide and to express a second cytoplasmic-expressing fluorescent protein, and (ii) a plurality of magnetic microbeads having affixed to the surface thereof a target protein, peptide or antibody.

A method is also provided for determining if one or more of two candidate ligand proteins or peptides bind(s) to a target protein, peptide or antibody comprising expressing a first candidate ligand protein or peptide as the first heterologous protein of the first plurality of cells in the instant system and expressing a second candidate ligand protein or peptide as the second heterologous protein in the instant system under conditions permitting the first heterologous protein and second heterologous protein to bind to the target protein, peptide or antibody and recovering any microbeads complexed with a first fluorescent protein-expressing cell and/or complexed with a second fluorescent protein-expressing cell, and identifying the candidate ligand protein in the complex, wherein recovery of microbeads attached to a complex of a first fluorescent protein-expressing cell indicates that the first candidate ligand protein or peptide binds the target protein or peptide, and wherein recovery of microbeads attached to a complex of a second fluorescent protein-expressing cell indicates that the second candidate ligand protein or peptide binds the target protein or peptide, and wherein no recovery of microbeads attached to a complex of a first fluorescent protein expressing cell or a second fluorescent protein expressing cell indicate, respectively, that the first candidate ligand protein does not bind the target protein or peptide, and that the second candidate ligand protein does not bind the target protein or peptide.

A system is provided comprising (i) a first plurality of suspension-adapted cell line cells transformed with a vector so as to express on a cell-surface thereof a first heterologous target protein or peptide and to express a first cytoplasmic-expressing fluorescent protein and one or more second pluralities of suspension-adapted cell line cells transformed with a second vector so as to express on a cell-surface thereof a second heterologous candidate ligand protein or peptide and to express a second cytoplasmic-expressing fluorescent protein, and (ii) a plurality of magnetic microbeads having affixed to the surface thereof an antibody directed to either the candidate ligand protein or peptide, or directed to the target protein or peptide. Also provided is a method for determining if a candidate ligand protein or peptide binds to a target protein or peptide comprising expressing the candidate ligand protein or peptide as the second heterologous protein of the second plurality of cells in the instant system and expressing the target protein or peptide as the first heterologous protein in the system of the instant system under conditions permitting the candidate ligand protein or peptide and the target protein or peptide to bind and recovering any microbeads complexed with both a first fluorescent protein-expressing cell and a second fluorescent protein-expressing cell, wherein recovery of microbeads attached to a complex of both a first fluorescent protein-expressing cell and a second fluorescent protein-expressing cell indicates that the candidate ligand protein or peptide binds the target protein or peptide, and wherein no recovery of microbeads attached to a complex of both a first fluorescent protein-expressing cell and a second fluorescent protein-expressing cell indicates, that the candidate ligand protein does not bind the target protein or peptide.

BRIEF DESCRIPTION OF THE DRAWINGS

FIGS. 4A-4C: Detection of T-cell ligand and receptor binding using the cell microarray platform. (4A) A high density cell microarray containing alternating rows of HEK cells expressing either cytoplasmic GFP or plasma membrane embedded PD-L1-GFP (shown schematically). (4B) Treatment of the array with purified PD-1 IgG premixed with Alexa 594 secondary antibody (RED) and imaged on an Axon 4000B microarray scanner. Only the cells presenting the PD-L1 ectodomain exhibit staining; the cells expressing cytoplasmic GFP show no staining and serve as the negative control. (4C) The merged image showing co-localization of the labeled PD-1-Ig-fusion protein and PD-L1 GFP, but not the cytoplasmic GFP construct. These results demonstrate the specificity of the microarray. The difference in GFP fluorescence intensity between PD-L1 and control (GFP alone) manifests from the method of expression.

FIGS. 8A-8D: Strategy for receptor:ligand discovery with high avidity microbeads. 8A) Suspension adapted HEK293 cells are transiently transfected with a cell surface of choice linked to a cytoplasmic mCHERRY (e.g., PD-L1; RED cells). 8B) 50 nm protein A-coated, GFP-tagged microbeads are decorated with either PD-1 Ig or B7-1 Ig-fusion proteins (GREEN beads). 8C) Incubation of the RED cells and GREEN microbeads results in RED:GREEN conjugates. 8D) Flow cytometry allows for detection and quantitation of the receptor:ligand interaction. Along the Y-axis are RED unbound transfected cells; along the X-axis are unbound GREEN microbeads; along the diagonal are the RED: GREEN cell:microbead conjugates that report of receptor: ligand interactions.

FIGS. 13A-13F: Strategy for parallel identification of cell surface protein-protein interactions. 13A) The barcoded library is generated through LIC cloning into a Barcoded Library vector (BC-L vector, which generates a GFP reporter and a 28 nucleotide unique core barcode, flanked by universal T7 forward and reverse primer sites). The library is pooled and transfected en masse into suspension adapted HEK293 cells. 13B) In a separate reaction, a single query receptor is transfected into HEK293 cells that are also marked with mCherry and a cell surface presented FLAG epitope to allow for magnetic capture/separation. 13C) The pooled library is mixed (1:1) with query expressing cells to allow for productive interactions between cognate receptors. 13D) Positive interactions (i.e., conjugates) are recovered from the expression pool by magnetic capture ("sorting") of query receptor cells. 13E) The plasmid DNA is extracted and PCR amplification of the Barcode is performed with the universal primers. 13F) Using massively parallel next-generation sequencing, the sequence of each PCR product is obtained. (5' AGACACCTATAA 3' (SEQ ID NO:5); 5' TTATAGGTGTCT 3' (SEQ ID NO:6)) The unique barcode signature uniquely identifies the ligands in complex with the query receptor. Notably, this protocol can be multiplexed by performing the above steps for large numbers of query proteins, individually capturing the resulting conjugates in a multi-well plate format (e.g., 24-well plate) and adding "well specific" identifiers (unique 8 nucleotide barcode) to the primers in step E. These amplicons can then be pooled into a single next-generation sequencing run and deconvoluted post sequencing to reduce the cost of each reaction.

FIGS. 15A-15C: Simulated signal-to-noise: Enrichment of a "rare" receptor from a pool by cell-cell binding coupled to FACS sorting. 15A) To simulate an expression library, $10^7$ HEK293 cells transiently expressing GFP were mixed with $0.02 \times 10^6$ cells expressing PD-1 GFP-fusion (0.2% of the GFP positive cells). This "library" was then challenged with $10^6$ HEK293 cells transiently expressing mCherry (negative control) or PD-L1 mCherry-fusion. The data shows flow cytometery analysis for $3 \times 10^6$ total events. Gates were set based on 10,000 event reads of the GFP "library", mCherry or PD-L1 mCherry-fusion alone. 15B) Schematic showing the location of the primers used to verify enrichment of PD-1 GFP-fusion. 15C) For the PD-L1 mCherry challenge (right panel in A, positive binding events (Q2) were sorted and 10,000 events were collected. For comparison, 10,000 cells were also collected from the cell mix prior to sorting (Pre Sort sample). The PD-1 GFP-fusion PCR control is in the left lane. A comparison of the pre and post sort PCR products verifies that the sorted positive binding events were enriched for PD-1 GFP.

FIG. 17A-17D: Cell-Cell "Rare Event" assay: 17A) The multiplexing approach permits pull out a specific binding interaction from a library, where the protein of interest will be relatively rare compared to the entirety of the library. For example, if one has a library of 100 genes and expresses them separately in mammalian cells and mixes those 100 expressing populations together in equal amounts, then any one gene expressed will represent 1/100 of the total library. 17B) This experiment demonstrates that even when a gene of interest, in this case PD-1, is 1/100 of the total population of GFP positive cells, one can still enrich for the PD-1/PD-L1 interaction using the technology described herein. As an initial test of the deep sequencing approach a set of previously characterized PD-L1 mutants was utilized. 17C) The idea was to use the mutant sequence as the "barcode" as each PD-L1 mutant sequence is inherently different. 17D) Several of these mutants showed decreased binding to PD-1, and it was possible to identify those same mutants using the multiplexed deep sequencing approach.

FIGS. 23A-23E: Extending the cell-cell binding assay to a 96-well plate format suitable for high-throughput protein-protein interaction screening. 23A) Duplicate sets of 16 control cell samples were setup at three different total cell concentrations and incubated for 2 hours at 4° C. in a 96-deep well block. Cell-cell mixes that contain cognate ligand:receptor pairs and should therefore demonstrate significant binding are highlighted in green (the bottom two rows of Table A). After incubation, an aliquot of cells was transferred to a 96-well U-bottom plate and analyzed using an Intellicyt HTFC continuous flow system connected to a BD Accuri cytometer. 23B) The well finder view from a representative 96-well plate run. Each peak represents the events collected from one well. Identifiers mark the end of each row of the 96-well plate. Note that the size of the peak is reflective of the concentration of cells in the well making the three different cell concentrations clearly distinguishable. 23C) All singlet cells from the entire 96-well plate were gated for GFP fluorescence, mCherry fluorescence or both (Double Positive "Hits"). 23D) Heat map showing the "Double Positive Hits" as a percentage of all singlet cell events. 23E) Graph shows double positives (Hits) as a percentage of total singlet cell events for all 16 control cell samples at each of the cell concentrations tested. Note that the percentage of cell-cell binding decreases with decreasing total cell concentration but the fold difference between negative and positive pairs improves slightly, from ~6-fold at $1 \times 10^6$ cells/mL to ~10-fold at $0.2 \times 10^6$ cells/mL. Data represents the average of two independent experiments with errors bars denoting the standard deviation.

DETAILED DESCRIPTION OF THE INVENTION

Figure 1:
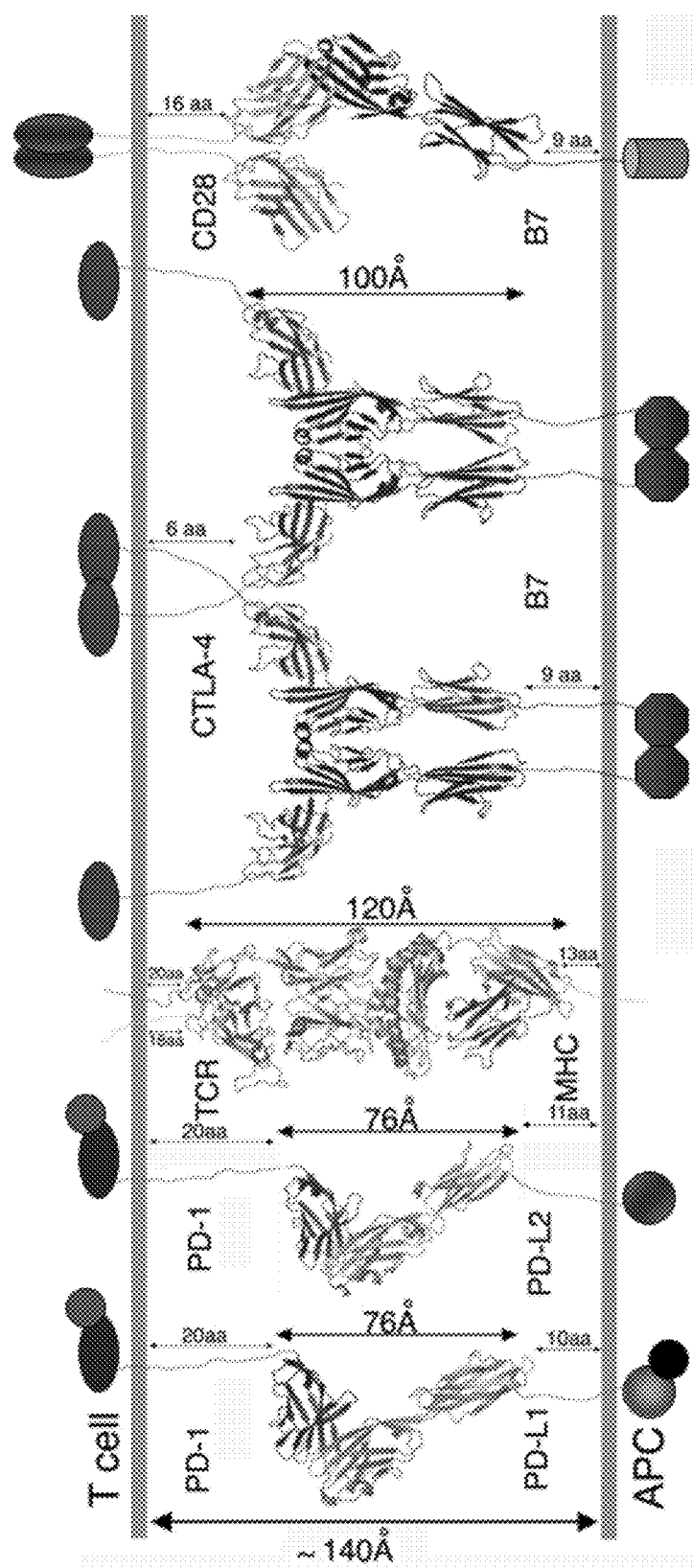
FIG. 1. Crystallographic view of the immunological synapse formed between T cells and antigen presenting cells. Composite model of the TCR:MHC and costimulatory receptor:ligand complexes in the central region of the immunological synapse. The TCR:MHC (PDB Code 1G6R), PD-1:PD-L1 (3BIK), PD-1:PD-L2 (3BP5) and CTLA-4:B7-1 (118L) complexes are representations of existing crystal structures; the model of the monovalent CD28:B7-1 complex is based on the CD28 monomer (1YJD) and the CTLA-4:B7-1 structure. The approximate dimensions (i.e. lengths) of the complexes are shown, as well as the number of residues connecting the structured Ig domains to the membrane. Also noted is the approximately 140 A° distance between the plasma membranes in the immunological synapse. Shown schematically (i.e., geometric symbols) are cytoplasmic signaling and scaffolding proteins that adopt the localization and organization imposed by the interactions between the receptor:ligand ectodomains. This Figure highlights the importance of receptor:ligand structures in defining basic features (e.g., oligomeric sate, valency, ligand specificity) and overall organizational principles that are critical determinants of function for cell surface receptors and ligands [45].

A cell microarray is provided comprising:
(i) a first plurality of cells transformed so as to express a first predetermined heterologous secreted protein, heterologous membrane protein or heterologous cell surface protein and a first fluorescent protein and (ii) at least a second plurality of cells transformed so as to express a second predetermined heterologous secreted protein or a second heterologous protein and a second fluorescent protein,
wherein the first and second plurality of cells are adhered to a solid surface of the microarray, and wherein the first and second plurality of cells are in spatially distinct locations on the solid surface.

A cell microarray is provided comprising:
(i) a first plurality of cells transformed so as to express (a) a first predetermined heterologous protein and (b) a first fluorescent protein and (ii) at least a second plurality of cells transformed so as to express (a) a second predetermined protein and (b) a second fluorescent protein,
wherein the first and second plurality of cells are adhered to a solid surface of the microarray, and wherein the first and second plurality of cells are in spatially distinct locations on the solid surface.

In an embodiment, the first or second predetermined protein is a classically secreted protein. In an embodiment, the first or second predetermined is a non-classically secreted protein. Non-classical secretion includes proteins such as FGF2, which has a well defined non-classical secretion pathway, as well as cytoplasmic proteins that are released due to cell lysis/death.

In an embodiment, the cell microarray further comprises a fusion protein comprising (i) a candidate protein or peptide ligand for one of the heterologous proteins and (ii) a third fluorescent protein bound to one of the heterologous proteins, or further comprising a compound comprising a peptide or protein ligand for one of the heterologous proteins, the compound having a third fluorescent protein bound thereto by a non-peptide bond, wherein the compound is bound to one of the heterologous proteins of the cell microarray.

In an embodiment, the cell microarray further comprises a third plurality of cells as a control, the third plurality of cells optionally transformed so as to express the first fluorescent protein, but not transformed with the first or second predetermined heterologous protein.

In an embodiment, each plurality of cells is a plurality of mammalian cells.

In an embodiment, the mammalian cells are isolated human cells.

In an embodiment, the mammalian cells are Human Embryonic Kidney (HEK) cell line cells.

In an embodiment, the mammalian cells are HEK293 cell line cells.

In an embodiment, the microarray comprises at least ten different pluralities of cells, each plurality transformed so as to express a predetermined heterologous protein and a first fluorescent protein, which heterologous protein is different from the heterologous protein expressed by each of the other pluralities of transformed cells in the microarray.

In an embodiment, the microarray comprises at least a hundred different pluralities of cells, each plurality transformed so as to express a predetermined heterologous protein and a first fluorescent protein, which heterologous protein is different from the heterologous protein expressed by each of the other pluralities of transformed cells in the microarray.

In an embodiment, the first and/or fluorescent protein is a green fluorescent protein or a yellow fluorescent protein.

In an embodiment, the third fluorescent protein is a red fluorescent protein.

In an embodiment, each plurality of cells is only transformed so as to express a first predetermined heterologous protein and a first fluorescent protein, and is not transformed to express any other heterologous protein.

In an embodiment, the first predetermined heterologous protein is a subunit of a multi-subunit heterologous protein, and the plurality of cells is also transformed to express one or more remaining members of the multi-subunit heterologous protein.

In an embodiment, the first predetermined heterologous protein is a attached through its C-terminal to the first fluorescent protein when expressed.

In an embodiment, the first predetermined heterologous protein is attached to a transmembrane anchor peptide when expressed.

In an embodiment, the cell microarray is fabricated by affixing a first plurality of expression constructs encoding the first heterologous protein and fluorescent protein on the solid surface of the microarray and affixing at least a second plurality of expression constructs encoding the second heterologous protein and fluorescent protein on the solid surface of the microarray on the solid surface in a spatially distinct location different from the affixed first plurality of expression constructs, and contacting the expression constructs with a plurality of cells under conditions comprising the presence of a transfection agent, so as to permit transfection of at least a portion of the cells in each spatially distinct location with the respective expression constructs.

In an embodiment, the expression constructs comprise a pEGFP-N1 expression construct. In an embodiment, the expression constructs comprise a CMV promoter.

In an embodiment, the cells are insect cells. In an embodiment, the cells are *Drosophila* S2 cells.

In an embodiment, the first or second predetermined heterologous protein is an immunoglobulin superfamily protein, a TNF receptor protein, a cytokine, a chemokine, a type 1 transmembrane receptor protein, a type 2 transmembrane receptor protein, an ion channel protein or a membrane transporter protein.

In an embodiment, the first or second predetermined heterologous protein as described herein is 1) of the entire secretome of human (i.e., ~8000 secreted and integral membrane proteins, including GPCRCs); 2) a non-classically secreted proteins of human/mouse; 3) a cytoplasmic protein that exhibits extracellular function via binding to a cell surface or secreted protein; or 4) a pathogen secreted or integral membrane protein.

In an embodiment, the first or second predetermined heterologous protein is, a toll-like receptor, a TNF receptor, a GPCR, a growth factor receptor, a nectin, an interleukin, or an interleukin receptor.

In an embodiment, the first or second predetermined heterologous protein is mammalian.

In an embodiment, the first or second predetermined heterologous protein is expressed in a plasma-membrane localized position. In an embodiment, the first and/or second heterologous protein is a secreted protein, a transmembrane protein or a cell surface protein. In an embodiment, the cell microarray comprises one of 100, 200, 300, 400 or 500 or more different pluralities of cells transformed to express a heterologous protein, wherein each plurality expresses a heterologous protein that is different from each other of the heterologous proteins expressed by the other pluralities of transformed cells. In an embodiment, the cell microarray comprises 750 or more different pluralities of cells transformed to express a heterologous protein, wherein each plurality expresses a heterologous protein that is different from each other of the heterologous proteins expressed by the other pluralities of transformed cells. In an embodiment, the cell microarray comprises 1000 or more different pluralities of cells transformed to express a heterologous protein, wherein each plurality expresses a heterologous protein that is different from each other of the heterologous proteins expressed by the other pluralities of transformed cells.

In an embodiment, the heterologous protein is a secreted protein and is expressed fused to a transmembrane helix.

In an embodiment, the first fluorescent protein and the second fluorescent protein are the same type, and the third fluorescent protein is of a different type.

In an embodiment, each plurality of cells is divided into spots of multiple cells, each multiple of cells less than the whole number of cells in the plurality, and wherein each spot is arranged so as to be closer to another spot of the same plurality of cells than to a spot of another of the pluralities.

A process is provided for making a cell microarray as described herein, comprising affixing a first plurality of expression constructs encoding the first heterologous protein and the first fluorescent protein on a solid surface of a microarray and affixing at least a second plurality of expression constructs encoding the second heterologous protein and the second fluorescent protein on the solid surface of the microarray in a spatially distinct location different from the affixed first plurality of expression constructs, and contacting the expression constructs with a plurality of cells under conditions comprising the presence of a transfection agent, so as to permit the cells to adhere to the solid surface and for transfection to occur of at least a portion of the cells in each spatially distinct location with the respective expression constructs.

In an embodiment, the expression construct can encode a single transcript for a fusion protein encompassing the heterologous protein and the fluorescent protein as a single covalently fused polypeptide. In an embodiment, the expression construct can encode the heterologous protein and the fluorescent protein as two distinct polypeptide (e.g. an IRES construct). In an embodiment, ligation independent cloning (LIC) is used to prepare the expression constructs. In an embodiment, traditional restriction site cloning is used.

A method is also provided for determining if a candidate protein or peptide binds to a second protein or peptide, the method comprising expressing the second protein as a heterologous protein of the cell microarray described herein, and contacting the cell microarray with the candidate protein or peptide, wherein the candidate protein or peptide has affixed thereto a third fluorescent protein or peptide, washing the cell microarray contacted with the candidate protein or peptide so as to remove unbound candidate protein or peptide, and determining if there is any candidate protein or peptide bound to the cell microarray after washing, wherein the presence of candidate protein or peptide bound to the cell microarray after washing in a first spatial location corresponding to cells transformed with a first heterologous protein indicates that the candidate protein or peptide binds to that first heterologous protein, and wherein the absence of candidate protein or peptide bound to the cell microarray in the first spatial location after washing indicates that the candidate protein or peptide does not bind to that heterologous protein.

In an embodiment, determining if there is any candidate protein or peptide bound to the cell microarray after washing is effected by measuring fluorescence of the third fluorescent protein and determining its location on the cell microarray, wherein co-localization of the third fluorescent proteins with the first or second fluorescent protein in a spatially distinct location indicates that the first protein or peptide is bound to the heterologous protein corresponding that spatially distinct location.

Also provided is a system comprising (i) a microarray solid surface and a suspension-adapted cell line transformed so as to express on a cell-surface thereof a candidate ligand protein or peptide and a first C-terminal cytoplasmic-expressing fluorescent protein and (ii) at least a) a second plurality of cells transformed so as to express a predetermined heterologous protein on the cell surface thereof and a second fluorescent protein, or b) a plurality of microbeads having affixed to the surface thereof the heterologous protein and having affixed a second fluorescent protein, wherein a) or b) is affixed to the microarray solid surface. A system is also provided as above, mutatis mutandis, wherein the candidate ligand protein or peptide is expressed on the second plurality of transformed cells or plurality of microbeads, and the heterologous protein is expressed on a cell-surface of a transformed suspension-adapted cell line.

Cells on the microarray can be probed with 1) a fluorescently-labeled probe protein; 2) a probe protein presented on a fluorescent microbead; and/or 3) a cell expressing the probe molecule on its surface.

In an embodiment, the system further comprises c) one or more further pluralities of cells transformed so as to express a different predetermined heterologous protein on the cell surface thereof and a second fluorescent protein, or d) one or more further pluralities of microbeads having affixed to the surface thereof the different predetermined heterologous protein and having affixed a second fluorescent protein, wherein c) or d) is affixed to the microarray solid surface in a spatially distinct location from the pluralities a) and/or b).

In an embodiment, the heterologous protein is affixed to the microbead via a Protein A molecule.

In an embodiment, the suspension-adapted cell line, transformed so as to express on a cell-surface thereof the candidate ligand protein or peptide, has been transiently transfected with a nucleic acid construct encoding the candidate ligand protein or peptide. In an embodiment, the heterologous protein is affixed to the microbead by being bound by an antibody attached to the microbead. In an embodiment, the first and second fluorescent proteins are different colors. In an embodiment, the one fluorescent protein is green and the other fluorescent protein is red. Non-limiting examples include green fluorescent protein and mCherry™.

In an embodiment, the plurality of cells is a plurality of mammalian cells. In an embodiment, the mammalian cells are isolated human cells. In an embodiment, the mammalian cells are Human Embryonic Kidney (HEK) cell line cells. In an embodiment, the mammalian cells are HEK293 cell line cells.

In an embodiment, the predetermined heterologous protein is a subunit of a multi-subunit heterologous protein, and the plurality of cells is also transformed to express the one or more remaining members of the multi-subunit heterologous protein. In an embodiment, the predetermined heterologous protein is a secreted protein, a membrane protein or a cell surface protein In an embodiment, the predetermined heterologous protein is attached through its C-terminal, when expressed, to the fluorescent protein. In an embodiment, the predetermined heterologous protein is a secreted protein and, when expressed, is attached to a transmembrane anchor peptide or protein. In an embodiment, the expression constructs comprise a pEGFP-N1 expression construct and/or a CMV promoter. In an embodiment, the heterologous protein is an immunoglobulin superfamily protein, a TNF receptor protein, a cytokine, a chemokine, a type 1 transmembrane receptor protein, a type 2 transmembrane receptor protein, an ion channel protein or a membrane transporter protein. In an embodiment, the heterologous protein is a toll-like receptor, a TNF receptor, a GPCR, a growth factor receptor, a nectin, an interleukin, or an interleukin receptor. In an embodiment, the heterologous protein is mammalian. In an embodiment, the heterologous protein is expressed in a plasma-membrane localized position.

A method for determining if a candidate ligand protein or peptide binds to a second protein or peptide, the method comprising expressing the candidate ligand protein or peptide and a first fluorescent protein in the suspension-adapted cell line plurality of the instant system, and contacting the plurality with a) the second plurality of cells transformed so as to express the heterologous protein and a second fluorescent protein, or b) the plurality of microbeads having affixed to the surface thereof the heterologous protein and second fluorescent protein, and washing to remove unbound candidate ligand protein or peptide, and identifying by FACS analysis cells that show co-localization of both the first and second fluorescent protein, wherein cells showing co-localization of both the first and second fluorescent protein in a spatially distinct location indicates that the first protein or peptide is bound to the heterologous protein corresponding that spatially distinct location.

In an embodiment, the co-localization of both the first and second fluorescent protein is determined by FACS analysis.

In the specific embodiment of a hemophilic interaction, the candidate ligand protein or peptide and the second protein or peptide have the same sequence.

A system is provided comprising a first plurality of suspension-adapted cell line cells transformed with a vector so as to express on a cell-surface thereof a first heterologous candidate ligand protein or peptide and to express a first cytoplasmic-expressing fluorescent protein and wherein the vector comprises a unique predetermined 15-35 nucleotide sequence for the first heterologous candidate ligand protein or peptide, the unique sequence capable of being primed by one or more universal primer(s), and a second plurality of suspension-adapted cell line cells transformed with a second vector so as to express on a cell-surface thereof a second heterologous candidate ligand protein or peptide and to express a first cytoplasmic-expressing fluorescent protein and wherein the second vector comprises a different unique predetermined 15-35 nucleotide sequence for the second heterologous candidate ligand protein or peptide, and (i) one or more further pluralities of suspension-adapted cell line cells transformed so as to express on a cell-surface thereof a receptor protein or peptide and to express a second fluorescent protein, which second suspension-adapted cell line comprises a stably-expressed peptide cell-surface epitope, or (ii) a plurality of magnetic microbeads having affixed to the surface thereof a receptor protein and having affixed a second fluorescent protein.

In an embodiment, the receptor protein can be classically recognized receptor. In an embodiment, the receptor protein may not be a classically recognized receptor but is simply a receiving protein for the ligand.

A system is provided comprising a first plurality of suspension-adapted cell line cells transformed with a vector so as to express on a cell-surface thereof a first heterologous protein and to express a first cytoplasmic-expressing fluorescent protein and wherein the vector comprises a unique predetermined 15-35 nucleotide sequence for the first heterologous protein, the unique sequence capable of being primed by one or more universal primer(s), and a second plurality of suspension-adapted cell line cells transformed with a second vector so as to express on a cell-surface thereof a second heterologous protein and to express a first cytoplasmic-expressing fluorescent protein and wherein the second vector comprises a different unique predetermined 15-35 nucleotide sequence for the second heterologous protein, and (i) one or more further pluralities of suspension-adapted cell line cells transformed so as to express on a cell-surface thereof a candidate ligand protein or peptide and to express a second fluorescent protein, which second suspension-adapted cell line comprises a stably-expressed peptide cell-surface epitope, or (ii) a plurality of magnetic microbeads having affixed to the surface thereof a candidate ligand protein or peptide and having affixed a second fluorescent protein.

In an embodiment, the universal primers comprise T7 forward and reverse universal primer.

In an embodiment, the peptide cell-surface epitope is a FLAG epitope (DYKDDDDK) (SEQ ID NO:1). In an embodiment, the system further comprises an anti-FLAG epitope antibody comprising a magnetic molecular entity, which antibody is bound to the FLAG epitope.

In an embodiment, the magnetic molecular entity is a superparamagnetic iron-impregnated bead. In an embodiment, the unique predetermined 20-35 nucleotide sequence is 28 nucleotides in length.

A method is also provided for determining if a candidate ligand protein or peptide binds to a second predetermined protein comprising expressing the second predetermined protein as a heterologous protein of the instant system and contacting with the candidate ligand protein or peptide of the (i) one or more further pluralities of suspension-adapted cell line cells transformed so as to express on a cell-surface thereof a candidate ligand protein or peptide and to express a second fluorescent protein, which second suspension-adapted cell line comprises a stably-expressed peptide cell-surface epitope, or of (ii) the plurality of magnetic microbeads having affixed to the surface thereof a candidate ligand protein or peptide and having affixed a second fluorescent protein; separating by magnetic attraction any of the first plurality of suspension-adapted cell line cells bound to one or more of the second plurality of cells or to the plurality of magnetic microbeads;

obtaining DNA from such separated cell-cell or cell-microbead conjugates and amplifying, using the universal primers, the unique sequence if present in the DNA;

sequencing copies of the unique sequence to confirm its presence;

comparing the unique sequence(s) so identified against a database correlating the unique predetermined 15-35 nucleotide sequence with specific heterologous protein or peptide, and thereby identifying any heterologous protein or peptide bind so correlated, thereby identifying a specific heterologous protein or peptide as binding to the candidate protein or peptide.

In an embodiment, the candidate ligand protein or peptide is affixed to the microbead via a Protein A molecule. In an embodiment, the candidate ligand protein or peptide is affixed to the microbead by being bound by an antibody attached to the microbead. In an embodiment, the first and second fluorescent proteins are different colors. In an embodiment, the one fluorescent protein is green and the other fluorescent protein is red. Non-limiting examples of such fluorescent proteins are provided hereinabove. In an embodiment, the plurality of cells is a plural In an embodiment, the mammalian cells are Human Embryonic Kidney (HEK) cell line cells. In an embodiment, the mammalian cells are HEK293 cell line cells. In an embodiment, the predetermined heterologous protein is a subunit of a multi-subunit heterologous protein, and the plurality of cells is also transformed to express the one or more remaining members of the multi-subunit heterologous protein. In an embodiment, the predetermined heterologous protein is attached through its C-terminal, when expressed, to the fluorescent protein. In an embodiment, the predetermined heterologous secreted protein is when expressed, attached to a transmembrane anchor peptide. In an embodiment, the heterologous protein is an immunoglobulin superfamily protein, a TNF receptor protein, a cytokine, a chemokine, a type 1 transmembrane receptor protein, a type 2 transmembrane receptor protein, an ion channel protein or a membrane transporter protein. In an embodiment, the heterologous protein is, a toll-like receptor, a TNF receptor, a GPCR, a growth factor receptor, a nectin, an interleukin, or an interleukin receptor. In an embodiment, the heterologous protein is mammalian. In an embodiment, the heterologous protein is expressed in a plasma-membrane localized position.

A system comprising (i) a first plurality of suspension-adapted cell line cells, wherein cells of the plurality are transformed with a vector so as to (a) express on a cell-surface thereof a heterologous protein and (b) express a first cytoplasmic-expressing fluorescent protein, and wherein the vector comprises a predetermined 15-35 nucleotide sequence unique for the heterologous protein expressed, such that the first plurality of suspension-adapted cell line cells expresses at least two different types of first heterologous protein, and (ii) a second plurality of suspension-adapted cell line cells transformed with a second vector so as to express on a cell-surface thereof a second heterologous protein and to express a second cytoplasmic-expressing fluorescent protein, wherein the second plurality of suspension-adapted cells expresses a single type of second heterologous protein. In an embodiment, any individual cell of the first plurality of cells expresses only one heterologous protein on the cell surface thereof. In an embodiment, none of the different types of first heterologous proteins of the first plurality have same sequence as second heterologous protein of the second plurality.

In an embodiment, the second heterologous protein is a membrane receptor. In an embodiment, each of the heterologous proteins expressed in the first plurality of suspension-adapted cell line cells is a secreted peptide, polypeptide or protein. In an embodiment, different types of first heterologous proteins of the plurality are each mutants of a predetermined wildtype protein. In an embodiment, the second heterologous protein is a wildtype protein. In an embodiment, each type of heterologous protein of the first plurality of different proteins differs from each other type of heterologous protein of the plurality by 1, 2, 3, 4 or 5 amino acid residue point mutations. In an embodiment, each type of protein of the plurality of different proteins differs from each other type of heterologous protein of the plurality by 1 amino acid residue point mutation.

In an embodiment, the unique sequence is capable of being primed by one or more universal primer(s). In an embodiment, the unique sequence is 15-35 nucleotides. In an embodiment, the first or second fluorescent protein is green. In an embodiment, the other fluorescent protein is red.

Also provided is a method for determining if a candidate ligand protein or peptide binds to second protein or peptide comprising expressing the candidate ligand protein or peptide as a first heterologous protein of the first plurality of cells in the system as described herein and expressing the second protein or peptide as a second heterologous protein in the systems as described herein under conditions permitting the first heterologous protein to bind to the second heterologous protein and, optionally, washing to remove any unbound first heterologous protein, then recovering cells with co-localization of both the first and second heterologous protein, obtaining nucleic acid from the recovered cells and sequencing the nucleic acid to identify the unique 15-35 nucleotide sequence contained therein so as to identify the candidate ligand protein or peptide corresponding to the unique 15-35 nucleotide that has bound the second protein or peptide.

Also provided is a method for determining the effect of a predetermined amino acid residue of a first protein on binding of the first protein to a second protein, the method comprising expressing the proteins mutated with one or more point mutations relative to the first protein as the plurality of different types of heterologous proteins in the first suspension-adapted cell line plurality of the systems described herein, and contacting the plurality with the second protein in the form of the second heterologous protein of the second plurality of cells of the systems described herein transformed so as to express the second protein and the second fluorescent protein, and recovering cells that show co-localization of both the first and second fluorescent protein, obtaining nucleic acid from the recovered cells and sequencing the nucleic acid to identify the unique 15-35 nucleotide sequence contained therein so as to identify the first protein that has bound the second protein or peptide, and comparing the level of protein that has bound the second protein or peptide to a predetermined reference level, wherein a level of protein that has bound the second protein or peptide in excess of the predetermined reference level indicates that the residue or residues as mutated in the protein enhance first protein binding to the second protein, and wherein a level of protein that has bound the second protein or peptide below the predetermined reference level indicates that the residue or residues as mutated in the protein inhibit first protein binding to the second protein.

In an embodiment, the predetermined level is a control. In an embodiment, the predetermined level is obtained by assaying the level of un-mutated first protein binding to the second protein. In an embodiment of the methods, cells that show co-localization of both the first and second fluorescent protein are recovered through FACS analysis.

Also provided is a system comprising (i) a first plurality of suspension-adapted cell line cells transformed with a vector so as to express on a cell-surface thereof a first heterologous candidate ligand protein or peptide and to express a first cytoplasmic-expressing fluorescent protein and a second plurality of suspension-adapted cell line cells transformed with a second vector so as to express on a cell-surface thereof a second heterologous candidate ligand protein or peptide and to express a second cytoplasmic-expressing fluorescent protein, and (ii) a plurality of magnetic microbeads having affixed to the surface thereof a target protein, peptide or antibody.

A method is also provided for determining if one or more of two candidate ligand proteins or peptides bind(s) to a target protein, peptide or antibody comprising expressing a first candidate ligand protein or peptide as the first heterologous protein of the first plurality of cells in the instant system and expressing a second candidate ligand protein or peptide as the second heterologous protein in the instant system under conditions permitting the first heterologous protein and second heterologous protein to bind to the target protein, peptide or antibody and recovering any microbeads complexed with a first fluorescent protein-expressing cell and/or complexed with a second fluorescent protein-expressing cell, and identifying the candidate ligand protein in the complex, wherein recovery of microbeads attached to a complex of a first fluorescent protein-expressing cell indicates that the first candidate ligand protein or peptide binds the target protein or peptide, and wherein recovery of microbeads attached to a complex of a second fluorescent protein-expressing cell indicates that the second candidate ligand protein or peptide binds the target protein or peptide, and wherein no recovery of microbeads attached to a complex of a first fluorescent protein expressing cell or a second fluorescent protein expressing cell indicate, respectively, that the first candidate ligand protein does not bind the target protein or peptide, and that the second candidate ligand protein does not bind the target protein or peptide.

A system is provided comprising (i) a first plurality of suspension-adapted cell line cells transformed with a vector so as to express on a cell-surface thereof a first heterologous target protein or peptide and to express a first cytoplasmic-expressing fluorescent protein and one or more second pluralities of suspension-adapted cell line cells transformed with a second vector so as to express on a cell-surface thereof a second heterologous candidate ligand protein or peptide and to express a second cytoplasmic-expressing fluorescent protein, and (ii) a plurality of magnetic microbeads having affixed to the surface thereof an antibody directed to either the candidate ligand protein or peptide, or directed to the target protein or peptide. Also provided is a method for determining if a candidate ligand protein or peptide binds to a target protein or peptide comprising expressing the candidate ligand protein or peptide as the second heterologous protein of the second plurality of cells in the instant system and expressing the target protein or peptide as the first heterologous protein in the system of the instant system under conditions permitting the candidate ligand protein or peptide and the target protein or peptide to bind and recovering any microbeads complexed with both a first fluorescent protein-expressing cell and a second fluorescent protein-expressing cell, wherein recovery of microbeads attached to a complex of both a first fluorescent protein-expressing cell and a second fluorescent protein-expressing cell indicates that the candidate ligand protein or peptide binds the target protein or peptide, and wherein no recovery of microbeads attached to a complex of both a first fluorescent protein-expressing cell and a second fluorescent protein-expressing cell indicates, that the candidate ligand protein does not bind the target protein or peptide.

In an embodiment of the methods, the cells that show co-localization of both the first and second fluorescent protein are magnetically sorted. Magnetic entities, such as beads can be attached to the second plurality of cells are magnetic separation invoked when a cell show co-localization of both the first and second fluorescent protein is identified. Accordingly, the methods and systems described herein may comprise magnetic entities, such as magnetic microbeads, attached to cells of the second plurality of cells and may comprise attaching the magnetic entities, such as magnetic microbeads, attached to cells of the second plurality of cells.

In an embodiment, the heterologous protein or peptide is heterologous to the cell it is expressed on in regard to the protein's source (e.g. another cell type or another species). In an embodiment, the heterologous protein or peptide is heterologous to the cell it is expressed on in regard to its location, for example, the protein is not expressed at that location (e.g. the cell surface) under normal physiological conditions (e.g. in vivo).

In an embodiment of the methods, PCR is performed on the unique 15-35 nucleotide sequences. In an embodiment, deep sequencing is performed on the pooled PCR products to identify the unique 15-35 nucleotide sequences. In an embodiment of the methods, the methods comprise determining if the unique 15-35 nucleotide sequences are enriched post-sorting (or post-recovering) versus pre-sorting (or pre-recovering).

In an embodiment of the methods and systems described herein, the unique sequence is 20-35 nucleotides. In an embodiment of the methods and systems described herein, the unique sequence is 20-30 nucleotides. In an embodiment of the methods and systems described herein, the unique sequence is 25-30 nucleotides. In an embodiment of the methods and systems described herein, the unique sequence is 20 nucleotides in length. In an embodiment of the methods and systems described herein, the unique sequence is 28 nucleotides in length.

In an embodiment of the methods described herein, the co-localizing cells, or recovered cells, are lysed and sequencing is performed on the contents of the supernatant thereof.

In a further embodiment of methods described herein, the method is performed in a multi-well dish with amplicons in each well being different from those of the remaining wells. In an embodiment, different wells of the multi-well dish comprise different receptor proteins.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

The need for continued structural characterization of receptor:ligand complexes: A wide range of biomolecules, including members of the immunoglobulin (Ig), TNF/TNFR, GPCR, chemokine and receptor kinase superfamilies, are central to the goal of systematic structural characterization of the Secretome. Below the CD28 receptor family is described (i.e., CD28, CTLA-4, ICOS and PD-1), a subset of the immunoglobulin superfamily (IgSF), that provides the principal signals for optimal T cell function [41-43]. These signaling receptors share structural features and recognize related cell surface ligands (e.g., B7-1, B7-2, ICOS-L, PD-L1 and PD-L2) with similar modes of interaction (FIG. 1) [44, 45]. For example, the engagement of CD28 by B7-1 and B7-2 leads to T cell activation, while engagement of the same B7 ligands by CTLA-4, provides inhibitory signals. The inducible co-stimulatory receptor (ICOS) provides additional important positive signals (i.e., co-stimulatory) upon binding ICOS-L, and engagement of PD-1 with either of its two B7-like ligands, PD-L1 and PD-L2, initiates further inhibitory pathways (i.e., co-inhibitory). The structures of these molecules and complexes, including several from this laboratory [28, 35, 46-48], have been instrumental in defining the fundamental mechanistic features (e.g., oligomeric state, valency, ligand specificity, etc.) and overall organizational principles required for co-stimulatory and co-inhibitory signaling as summarized in FIG. 1.

Figure 2:
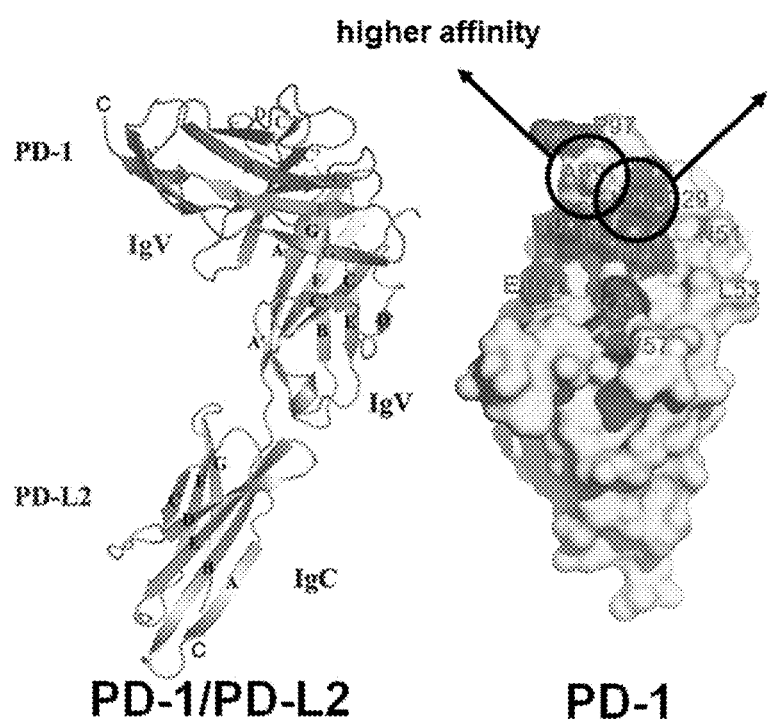
FIG. 2: Exploitation of Receptor:Ligand Structures Left: The structure of the murine PD-1:PD-L2 complex. Right: Location of point mutants resulting in PD-1 receptors with enhanced affinities and altered specificity.

Beyond defining basic biophysical and organizational features, these structures provide the basis for generating novel biochemical reagents and unique mechanistically informative model systems. For example, guided by the structure disclosed herein of the PD-1:PD-L2 complex [35], a mutant murine PD-1 receptor was generated that binds murine PD-L2 with wild type affinity, but which exhibits no interaction with PD-L1. Based on these findings, herein is disclosed generation of Ig-fusion proteins and knock-in mouse models that provide unprecedented opportunities to dissect the mechanistic role of the two ligand-associated signaling pathways in normal physiology and disease (FIG. 2). Also, based on the structure of this complex, a single point mutant of the human PD-1 receptor was generated with 50- and 30-fold higher affinities for human PD-L1 and PD-L2, respectively (unpublished data). This reagent represents a novel high affinity species that may offer unique therapeutic opportunities (see below). These examples highlight the extreme value of such receptor:ligand structures and the manner in which they can be leveraged for biological insights and new therapeutic opportunities.

New, critical receptor:ligand interactions remain to be defined. Of particular relevance to this application, even within the very heavily studied CD28 family of receptors, additional important interactions have only very recently been discovered. B7-1 has been demonstrated to bind PD-L1, resulting in bi-directional inhibitory signals, while ICOS-L has been demonstrated to bind both CD28 and CTLA4, with the CD28:ICOS-L interaction being essential for human T cell activation [49, 50]. These intersecting and competing interactions result in a highly complex network of signaling pathways. These examples highlight the value of systematically defining the entire repertoire of receptor:ligand interactions, as the discovery of even a single new receptor:ligand pair can significantly impact the mechanistic understanding of the signaling pathways relevant to T cell function, human physiology and disease.

Therapeutic relevance of receptor:ligand complexes. Importantly, many cell surface molecules and their associated binding partners are outstanding targets for the deliberate modulation of signaling pathways to treat a wide range of human disease. Function blocking antibodies targeting cell surface immune receptors and ligands are a major class of protein therapeutics for the manipulation of immune responses to treat infectious diseases, autoimmune diseases, and malignancies. A prime example includes Yervoy™ (Bristol Myers Squibb), a function blocking mAb against the CTLA-4 inhibitory receptor, which results in a global immune stimulation and which received FDA approval for the treatment of late-stage melanoma in March 2011 [51]. These immune receptors are not only targets, but are themselves powerful therapeutics. For example, a soluble version of CTLA-4, marketed as Orencia™ (BMS), competes with CD28 for binding the B7 ligands, resulting in inhibition of the CD28-associated stimulatory pathway. The blockade of CD28 stimulation results in global immune suppression making Orencia a leading treatment for autoimmune diseases including rheumatoid arthritis [52]. Of particular note is Belatacept™ (BMS), a soluble CTLA-4 variant of Orencia that possesses two point mutations. Belatacept received FDA approval in November 2011 for prevention of acute kidney transplant rejection showing equivalent efficacy to existing treatments and, as a result of the mutations, greatly reduced side effects and toxicity. Notably, Belatacept possesses only a two-fold increase in avidity for the B7 ligands, but exhibits a ten-fold enhancement in its biological potency [26, 53]. Such findings strongly support a continued role for structural and biochemical analysis of the primary co-stimulatory molecules and their cognate complexes in order to gain molecular insight that supports the development of novel therapeutic agents. These principles can be generalized to the entire Secretome.

The realization of the proposed high-throughput technologies will provide powerful research tools for use, in for example, interactions associated with the human Secretome, defining the range of extracellular host:pathogen interactions associated with viral, bacterial, fungal and parasitic diseases (for example [54]), identifying host:pathogen interactions. Additionally, recent evidence suggests that a number of "seemingly" cytoplasmic proteins also possess extracellular functions [55-59]. Non-classical secretion mechanisms (i.e., signal sequence-independent secretion) continue to be described and are the subject of considerable investigation [60, 61]. Notably, the cell surface receptors of many of these non-classically secreted proteins have not been identified.

The considerable value of defining the interactions associated with the mammalian Secretome has long been recognized and has elicited considerable attention from the small biotech, large Pharma and academic communities. Efforts arising from academic labs have been performed on very modest scales [62, 63]; the most prominent/expansive examples include the contributions of Genetech and Five Prime Therapeutics, Inc. Genentech exploited their considerable resources to generate a library of >1000 Ig-fusion proteins for direct binding analysis using surface plasmon resonance technology. These efforts resulted in the discovery of new ligands for Ig Superfamily members, BTLA and TIGIT [64, 65]. Given that each individual target (e.g., TIGIT) needed to be individually screened against each member of the library, this approach lacked the features required for the realization of true high-throughput. Genentech recently described a protein array in which ~700 secreted proteins were individually pinned onto a solid support; this array was subsequently screened with multivalent reagents individually presenting ~90 human Ig-fusion proteins [66]. This platform supported the discovery of new and surprising receptor:ligand interactions, including the unexpected interaction between B7-1 and NGFR.

In contrast to these "arrayed" approaches, Five Prime Therapeutics, Inc. took a more "brute force" approach in which 3400 constructs of secreted proteins and ectodomains of transmembrane proteins were individually expressed in 293T cells [67]. These proteins were examined in 30 distinct HTP assays that probed metabolic, transcriptional and growth responses relevant to immune and cardiovascular function, as well as cancer proliferation, in a wide range of cell lines. These efforts resulted in the demonstration that the previously uncharacterized protein IL-34 was a ligand for the (seemingly) well characterized colony-stimulating factor 1 receptor. This study is a prime example of the need to de-orphanize molecules (e.g., IL-34), and highlights the fact that even well-characterized cell surface molecules may have unsuspected interactions.

These high-throughput approaches for identifying receptor:ligand interactions are among the most exciting recent developments in the biological sciences, as they hold the potential to discover new fundamental biological mechanisms and to yield new therapeutic strategies. However, for several reasons, these studies may not achieve the wide spread impact that might be desired. First, the ability to generate the enormous number of secreted proteins/Ig-fusions required for these assays is outside the capabilities of even the most ambitious academic, laboratories, including those supported by the Protein Structure Initiative. Furthermore, all of these approaches fail in cases where the proteins cannot be purified, exhibit instability during storage and subsequent manipulation, or exhibit unfavorable solution behavior (e.g., aggregation, which commonly afflicts Ig-fusion proteins). In the case of the Five Prime Therapeutics screen, proteins with biological functions (or cognate binding proteins) not covered by the selected cell-based screens will not yield an interaction. Of particular note, all of these approaches are incompatible with some of the most important classes of integral membrane proteins, including GPCRs, transporters and channels, as these proteins are generally not compatible with high-throughput purification of functionally active material and cannot tolerate the physical process of arraying. Finally, and perhaps most importantly, the results reported from these commercial efforts represent only those interactions deemed acceptable for release to the general public; numerous "non-scientific" factors influence these decisions and it is a near certainty that a substantial proportion of these important data will never make it into the public domain.

Herein are disclosed three technologies for affordable, efficient and high-throughput identification of interactions involving, for example, the mammalian Secretome for high-resolution structure discovery, biochemical analysis and therapeutic development. The disclosed technologies offer numerous advantages over existing methods: 1) expression in cell microarray format allows for the systematic expression of all classes of proteins (including multi-span integral membrane proteins such as GPCRs and transporters, as well as multicomponent receptors such as integrins); 2) cell microarray expression is highly tractable, as only DNA (i.e., expression vectors) are required, and not the purified proteins themselves; 3) the technologies are all based on the detection of direct physical interactions, and thus do not require any knowledge of biological function; 4) the flow cytometry-based method allows both the bait and the prey to be expressed on the surfaces of independent and distinguishable cells, thus removing all requirements for purified protein; and 5) the implementation of magnetic separations coupled with deep sequencing and a barcoded library of secreted protein-expressing cells offers massively parallel interrogation of many (all) ligands against the entire panel of potential receptors.

Figure 3:
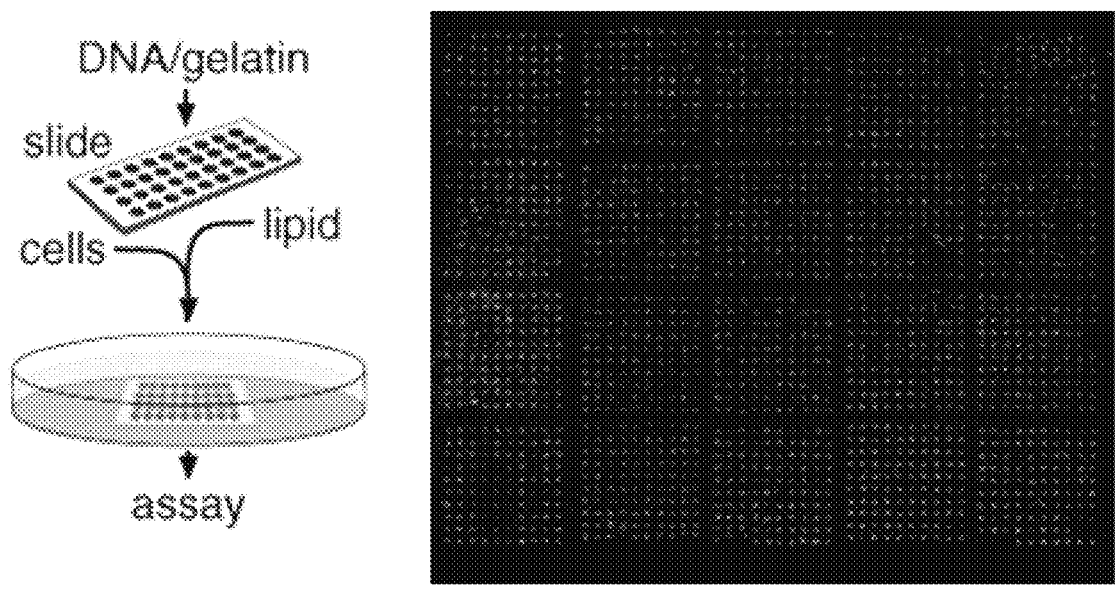
FIG. 3: Cell Microarray Platform. Left: Schematic for generating cell microarrays. Right: For illustration, a GFP expression construct (i.e., plasmid) was "pinned" onto a glass surface to create an expression array. HEK293 cells were plated over the printed cDNAs, which subsequently became transfected, resulting in a living cell array. This 2000-spot grid was constructed using a custom-built microarray printer. Each spot is a cluster of 50-80 cells.

Development of cell microarrays for high-throughput identification of cell surface protein-protein interactions: Cell microarray technology is adapted to systematically screen a pan-genomic library of cell surface receptors (i.e., the Secretome) against single query ligands. This approach presents large numbers of receptors in the context of live host cells in a precisely arrayed format. To efficiently screen the libraries of potential receptor constructs, cellular microarray technology [68, 69] has been successfully adapted. Each expression construct (e.g., plasmid based on the pEGFP-N1 backbone and other fluorescent variants, which drive expression via the CMV promoter) is individually "pinned" onto a glass surface to create an expression array of library molecules. Mammalian cells, when plated over the printed cDNAs in the presence of transfection reagent (e.g., lipid-based reagent), become transfected, resulting in a living cell array, with each individual cluster expressing a distinct member of the library (FIG. 3). (Cells growing between the printed cDNAs are not transfected and remain "black".) These expression arrays are then challenged with purified fluorescently-tagged query proteins. Positive interactions are scored as a function of fluorescence after washing to remove unbound ligand. As each construct is "pinned" at a known position in the microarray, a positive "hit" can immediately be correlated with its interacting partner.

Figure 5:
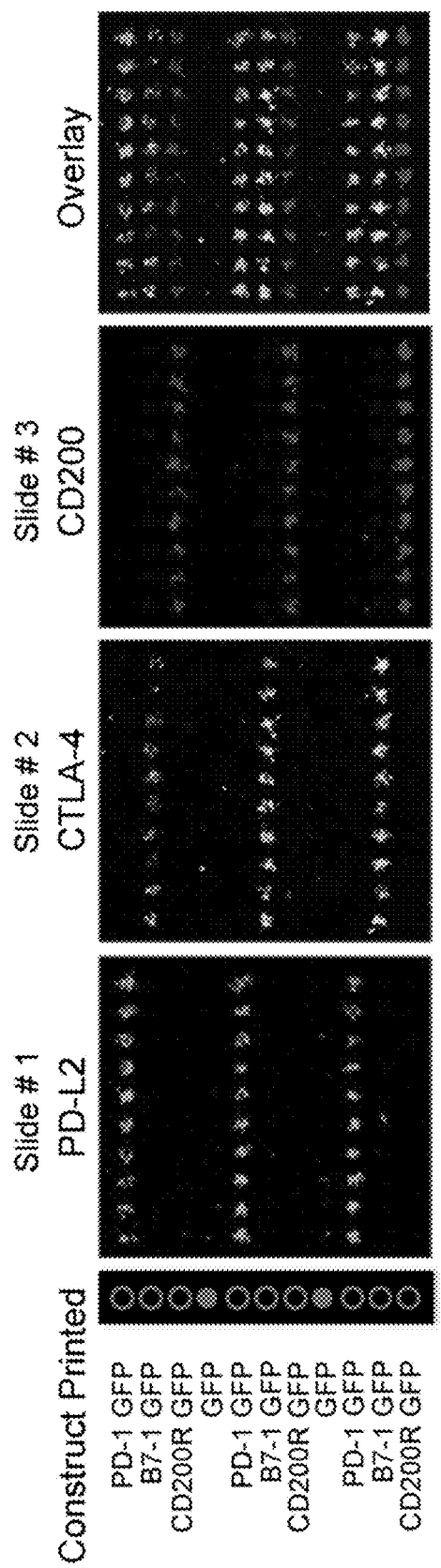
FIG. 5: Three cell microarrays showing specific binding between different members of the Ig superfamily. Slides were printed with alternating rows of plasmid DNA encoding GFP fusion constructs of PD-1, B7-1 and CD200R, or GFP alone. Three printed slides were placed in a 10 cm square petri dish, treated with transfection reagent and then plated with HEK cells. 3 days post transfection the slides were washed and subsequently treated with Ig-fusions of PD-L2 (Slide 1), CTLA-4 (Slide 2) or CD200 (Slide 3); Ig-fusions were pre-incubated with Cy7 secondary antibody for detection. All printed rows successfully transfected and were GFP positive (data not shown). The images show the fluorescence signal from the Cy7 channel only. For each array, significant binding of the Ig-fusion is detected for only those rows where its cognate receptor or ligand is present. For example: PD-L2, a ligand of the receptor PD-1, only binds in those rows where PD-1 GFP was printed. The individual slides were pseudo-colored for clarity and the overlay reveals the specific pattern of binding.

The cell microarray platform was validated using the PD-1:PD-L1 interaction (Kd ~5.5 µM). A live cell microarray was generated consisting of alternating rows of cells expressing either a GFP fusion of PD-L1 or GFP alone (FIG. 4A). As illustrated in the schema (FIG. 4, far left), the GFP control is expressed in the cytoplasm (solid green circle), while the GFP fused to PD-L1 (green ring) is membrane localized (the lower absolute GFP fluorescence observed for the PD-L1-GFP is due to the higher expression level of the cytoplasmic GFP construct). By challenging these arrays with a RED Alexa 594-bound bivalent Ig-fusion (i.e., Fc-fusion) construct of the PD-1 ectodomain, those spots specifically expressing the cognate PD-L1 ligand were correctly identified (FIG. 4B/C). These experiments clearly demonstrate the cell microarray technology for identification of receptor:ligand complexes. FIG. 5 shows cell microarray technology for a range of different protein interactions (PD-1:PD-L2, CTLA-4:B7-1 and CD200R:CD200); these results further validate the wide spread applicability of the cell microarray platform and highlight the signal-to-noise and specificity of this approach.

Figure 6:
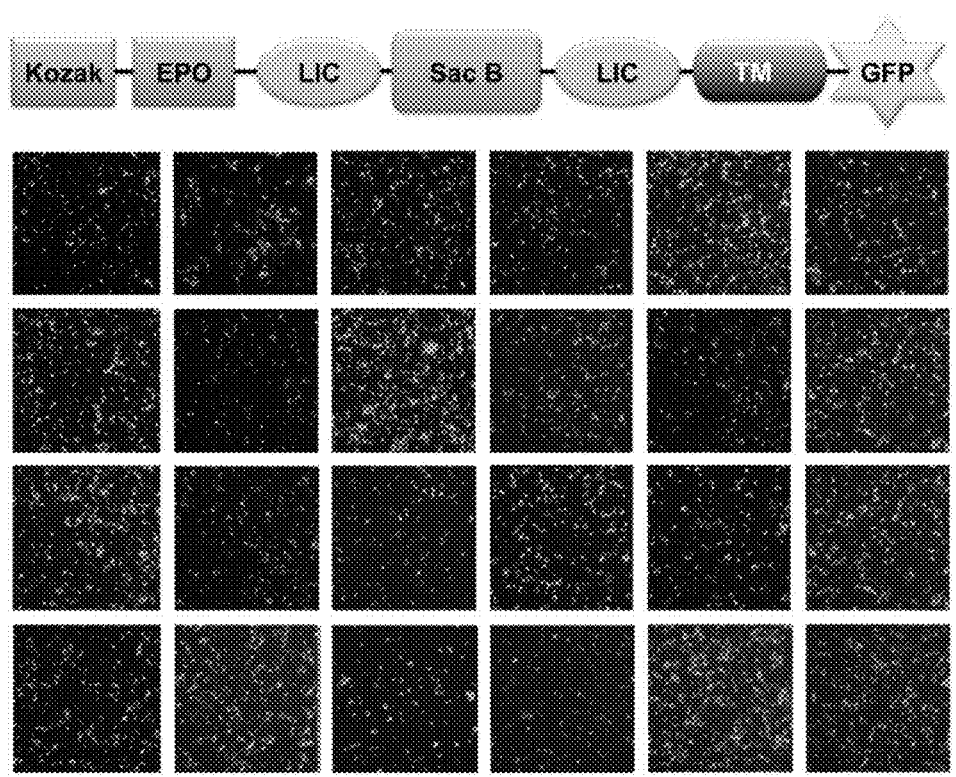
FIG. 6: Generation of a Ig superfamily mammalian expression library. The schematic diagram (top) shows the ligation independent vector that was engineered specifically for the rapid and efficient cloning of type I secreted proteins. 283 members of the Ig superfamily have been cloned and tested expression by transient transfection of HEK293 cells. Using fluorescence microscopy, 240 (~85% success) of the clones expressed above background and displayed the correct membrane localization. Shown are GFP fluorescence images for a representative set of 24 of the 240 expressing library members. Pre-validation of each expression construct highlights those proteins that require additional "rescue efforts" and is critical for a fully characterized and robust platform.

The 14 members of the nectin/nectin-like family belonging to the Ig Superfamily (IgSF) are similarly investigated. At least 10 of these proteins exhibit homophilic interactions and there are at least 20 heterophilic interactions between members of the nectin family [70-72]. Also the ~500 ectodomains and secreted proteins that comprise the entire human IgSF are run through this system. In these experiments, expression vectors for each member of the IgSF are printed to generate the microarray (i.e., each spot represents a single member of the IgSF), which is probed with Ig fusion constructs of specific IgSF members. As the majority of IgSF members bind other members of the IgSF, this affords exciting opportunities to define new receptor:ligand interactions within the IgSF. Based on their considerable mechanistic and therapeutic importance in cancer biology and autoimmune disease, identifying ligands for the IgSF members B7-H4[73-80], VISTA[81], B7-H3[74, 79, 82-85], LAG-3[86-90] and the 10 members of the butyrophilin family[91-94] is also warranted. Other members of the IgSF, including other members of the extended B7, Carcinoembryonic antigen-related cell adhesion molecule (CEACAM) [95] and leukocyte receptor complex[96] families, are candidate targets. The expression reagents for a significant fraction of the IgSF have been successfully generated and validated (FIG. 6).

All members of the TNF and TNFR superfamilies can be part of the platform; all of these proteins are important mechanistic and therapeutic targets and are type-II membrane proteins (i.e., TNF superfamily members). The technology can be applied to the entire Secretome, including GPCRs, Toll-like receptors, growth factor receptors, interleukins, interleukin receptors, ion channels, etc.

Cloning: Access to the large number of required cloning templates is available. For example, the NYSGRC has in hand the entire human mammalian genome collection (MGC) cDNA set from OpenBiosystems and these cloning templates are freely available. In a preferred embodiment, highly efficient Ligation Independent Cloning (LIC)[97] is used for the generation of the expression libraries; the inserted genes of interest will be followed by a transmembrane anchor and will be covalently fused at its C-terminus (type-I membrane proteins) to a cytoplasmically localized GFP expression reporter (FIGS. 4 and 6). Recently, the implementation of LIC cloning has supported the generation of >15,000 sequence-verified constructs over the past 18 months for large-scale structural (nysgrc.org) and functional genomics (enzymefunction.org) programs. The method is aided by automated liquid handling robots, for example, a Biomek FxP liquid handler and a Perkin-Elmer EP3 robot, for the high-throughput molecular biology needed to rapidly generate the above library. All of the required expression vectors are readily generated (FIG. 6).

Figure 12A:
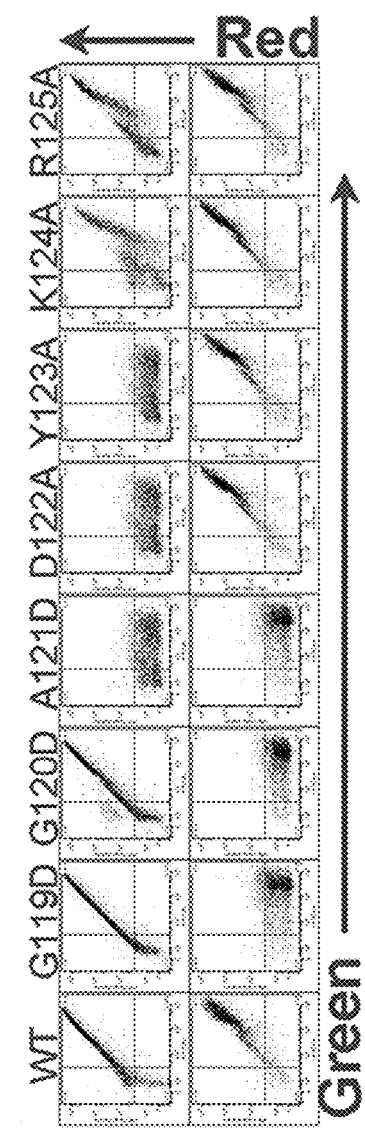
FIGS. 12A-12B: Use of the microbead and cell-cell FACS assays to identify PD-L1 mutants with highly selective function. 12A) A set of >100 PD-L1 mCherry mutant constructs were transiently transfected into HEK293 cells. These lines were then challenged with microbeads pre-saturated with an Ig-fusion of PD-1 (Microbead data in orange) or, in a separate set of experiments, with cells transiently expressing PD-1 GFP (Cell-Cell data in blue). In each experiment, the percent binding, determined by FACS analysis, was normalized to wild-type binding. The data show a direct comparison of the average binding observed using either the microbead or cell-cell method. For clarity, only a subset of the data is shown. A similar set of experiments was also carried out challenging the PD-L1 mutants with B7-1, the other known ligand of PD-L1 (data not shown). 12B) Screening the PD-L1 mutants produced several mutants that show impaired binding to either PD-1, B7-1 or both. To further verify these results seven of the PD-L1 mutants were expressed as Ig-fusions. The purified PD-L1 mutants were pre-incubated with Alexa 594 secondary Ab (Red) for detection and added to either PD-1 GFP or B7-1 GFP (Green) expressing HEK293 cells. The FACS data show the GFP fluorescence (X-axis) versus the Alexa 594 fluorescence (Y-axis). The extent of binding observed using purified protein mirrors that observed in both of the screening methods, although the data appears to correlate more closely with the results obtained with the cell-cell binding method.
Figure 12B:
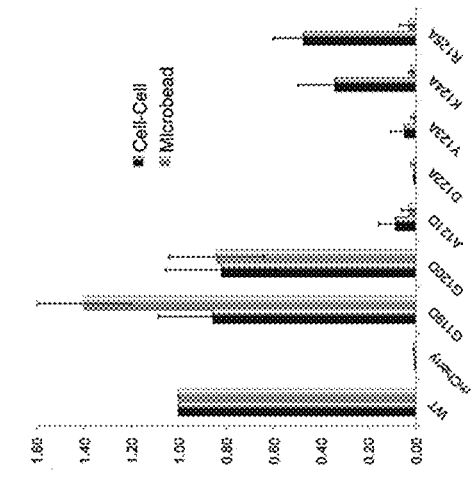

Generation of quality of Ig-fusion constructs of query proteins: High-throughput transient transfection and lentivirus-driven platforms have been established for the generation of secreted proteins and in particular for Ig-fusion proteins. FIG. 12 shows a number of mutant PD-L1 Ig-fusion constructs that have recently been generated. This platform is based on the Daedelus system [98] and has the capacity to generate 48 lentiviruses per week. Furthermore, myriad secreted proteins and ectodomains have been effectively generated used as soluble Ig-fusion proteins for mechanistic studies [21-23] and therapeutic applications [24-27]. This enormous literature demonstrates that covalent fusion to non-native domains does not have a deleterious effect and is compatible with a wide range of secreted proteins and ectodomains.

Expression of functional plasma membrane-localized GFP-fusions in the cell microarray: Natural integral membrane proteins will utilize native transmembrane elements to avoid the issue of differentiating between Type I and Type II integral membrane proteins in the context of cell microarray screening. Importantly, numerous examples of biologically relevant fluorescent protein-fusions (e.g., GFP-fusions) have been reported, including members of the Ig, TNF/TNFR[1-3], GPCR[4-6], integrin[7] and transporter[8] superfamilies. For cell microarrays, secreted proteins can be effectively engineered into integral membrane proteins through the addition of a transmembrane helix that anchors them to the cell surface for subsequent probing. Based on the existence of numerous proteins from numerous families, which have both biologically important membrane-anchored and secreted forms due to alternative splicing and/or shedding (i.e., proteolysis)[9-19], tethering is not an issue. Furthermore, multiple secreted proteins (e.g., IL-2 and GM-CSF) have been deliberately engineered as single span intrinsic membrane proteins to afford novel therapeutic strategies (e.g., vaccine design)[20].

Figure 7A:
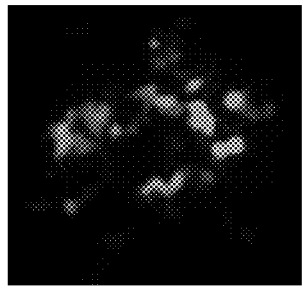
FIGS. 7A-C: Cotransfection in cell microarray format. Left) 7A) HEK293 cells transfected with cytoplasmic GFP. Middle) 7B) HEK293 cells transfected with cytoplasmic mCHERRY. Right) 7C0 HEK293 cells cotransfected with cytoplasmic GFP and mCherry. Cotransfections with GREEN and RED fluorophores results in YELLOW fluorescence. This provides proof-of principle for the expression of multiple polypeptides, as is required for realization of functional multicomponent receptors in cell microarray format.
Figure 7B:
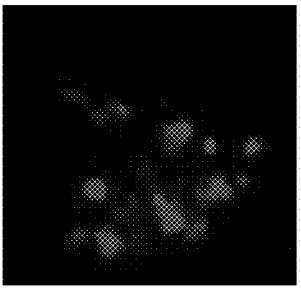
Figure 7C:
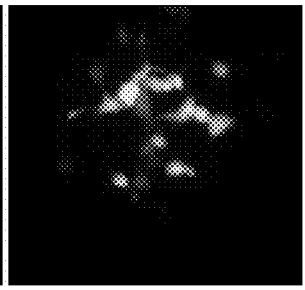

Some receptors require multiple components in order to exhibit binding activity to their cognate ligands (e.g., T cell receptor, integrins). As appropriate, these more complicated receptors are addressed by co-expressing multiple components at a single position of the cell microarray (FIG. 7).

Cell line selected for microarray presentation: Cell microarray technology has been firmly established with HEK293 cells. For distinguishing those query proteins that bind to cell surface proteins that are endogenously expressed by the HEK293 cells, binding to the untransfected control cells present in all microarrays (i.e., those cells not receiving an expression vector coding for a plasma membrane localized protein) serves as a convenient control. However, in most cases the saturating levels of over-expression driven by the strong CMV promoter will dominate the low endogenous levels of cell surface expression. Moreover, appropriate statistical methods can identify statistically signal binding events. To aid in these statistical analyses, all expression vectors can be printed in duplicate in the cell microarray. Importantly, a wide range of alternative cell lines can also be utilized as "rescue host lines" in the microarray. For example Drosophila S2 cells have been utilized by Sabatini for genome-scale loss-of-function studies in microarray format [99, 100].

Figure 9:
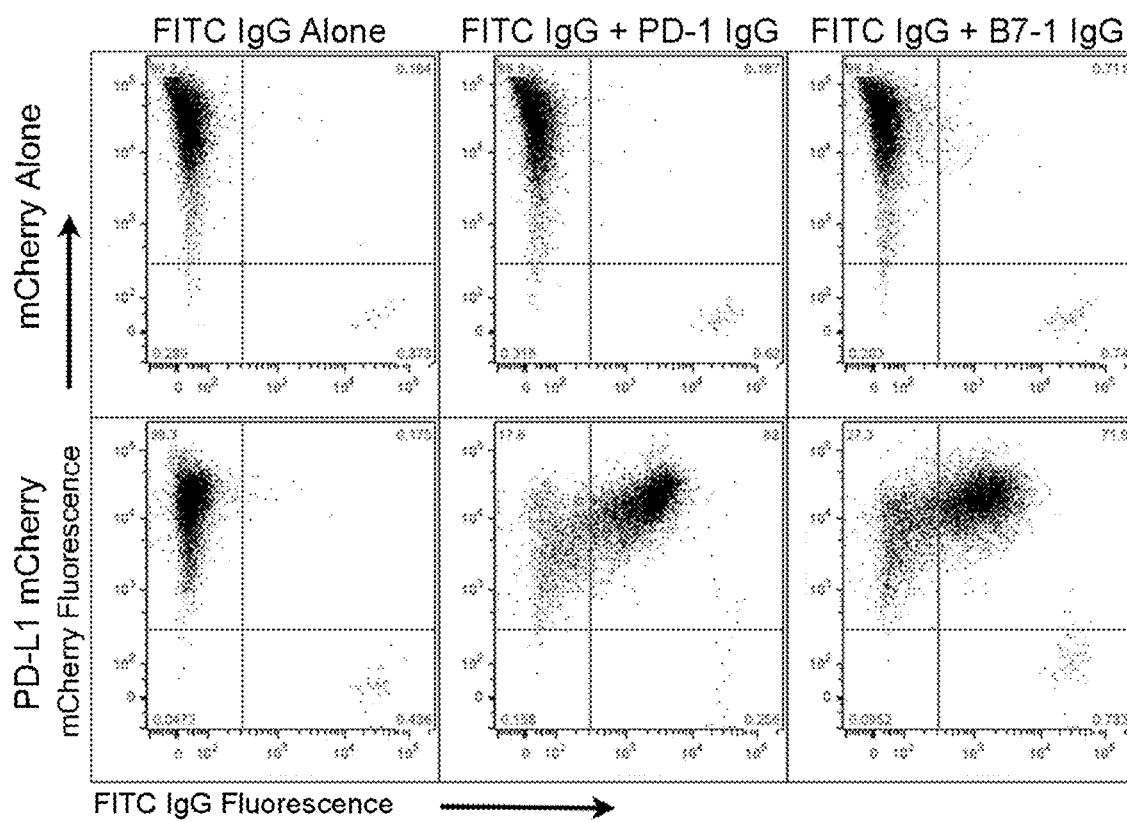
FIG. 9: Microbead-based demonstration of PD-L1:PD-1 and PD-L1:B7-1 interactions. Protein A microbeads were saturated with IgG premixed in a 1:4 ratio of FITC-IgG to Ig-fusion (i.e. PD-1 or B7-1) pelleted and subsequently resuspended in PBS. Conjugated microbeads were incubated with HEK cells expressing either mCherry alone or a PD-L1 mCherry fusion, and the extent of binding determined by flow cytometry. These data clearly demonstrate binding of both PD-1 conjugated and B7-1 conjugated microbeads to only PD-L1 expressing HEK cells and supports the strategy that increasing the avidity of the ligand improves the dynamic range of potential receptor-ligand interactions that can be measured experimentally.

Avidity and dynamic range: Bivalent Ig-fusions have been effective for the identification of interactions with moderate affinities (i.e., PD-1:PD-L1; Kd=5.5 µM). Challenging PD-L1 expressing cells with higher valency B7-1 decorated-microbeads allowed for robust recruitment and specific identification of receptor:ligand binding in flow cytometry-based experiments (FIG. 9). This comparison supports the notion that increasing the avidity of the ligand expands the dynamic range of potential receptor:ligand interactions that can be measured experimentally, improves the ability to detect binding to printed cell microarrays. For lower affinities, probing the microarrays with high avidity multivalent microbeads decorated with, for example, Ig-fusion proteins, is useful.

Higher avidity with transiently transfected cells: Experiments described above involve probing living cell arrays with purified query ligands, ultimately pushing the burden of the experiment towards query protein production and labeling. To enhance the ease, utility and throughput of the platform, suspension-adapted mammalian cell lines with decreased adherence properties (i.e., HEK293 Freestyle (Invitrogen) [101]) can be used that express the query protein on its surface, immobilized by a single transmembrane helix fused with a cytoplasmic C-terminal mCherry reporter protein (or other suitable fluorescent protein). The mCherry (red) suspension cells are then be used to challenge the immobilized green "receptor" cells on the array. Co-localized cell spots containing both GFP (e.g., microarray localized receptors) and mCherry (e.g., suspension query ligands) would result in a positive score. Expressing the query ligand in a cellular context removes the burden of query ligand purification and labeling; it has the added advantage of maintaining the query protein ligand in an environment closer to the native state, which is critical for proteins such as GPCRs, etc. To address non-specific binding, and background, the following is noted. Each "spot" in a cell microarray represents a cluster of cells overexpressing defined gene products among a monolayer of untransfected cells. The observed background results from non-specific interactions with the monolayer of untransfected cells across the microarray, coupled with the general inability to vigorously wash the microarray prior to fluorescence detection. Enhancement of monolayer adherence to withstand the rigors of washing, or the spatially-restricted deposition of cells to specifically defined areas with clear boundaries, can alleviate these issues. To improve localized adherence of spotted cells in the context of the microarray, a HEK293 cell line that stably expresses a functional cell surface resident single chain-Avidin (scAvidin) has been successfully engineered by using a non-classical secretion system to direct and anchor scAvidin in the outer leaflet of the plasma membrane (data not shown)[102]. This stable cell line specifically binds non-cell permeable Alexa 594 labeled biotin and this strategy can be used to either anchor cells to the array globally, if more rigorous washing steps are desired, or can be used to specifically tether cells to defined areas via site specific printing of biotin conjugates. Both scenarios will reduce the background signal.

Statistical analysis of cell microarrays: While highly significant interactions are readily discernible by eye (e.g., FIGS. 4 and 6), appropriate statistical criteria are preferably applied to identify weaker interactions that are statistically significant.

Automated flow cytometric technologies for high throughput identification of cell surface protein-protein interactions. A powerful alternative method for determining specific receptor:ligand interactions using flow cytometry is also disclosed. This platform allows for the facile examination of affinity probes with a wide range of avidities (i.e., bivalent Ig-fusions, high avidity microbeads and very high avidity transiently transfected cells). The use of Ig-fusion proteins is conceptually similar to the experiments described above. The utility of microbeads and transiently transfected cells for the discovery of new receptor:ligand interactions is more fully described hereinbelow.

The microbead-based approach is demonstrated with the same PD-1:PD-L1 interaction described above, and expanded by including the PD-L1:B7-1 interaction. FIG. 8 shows the overall strategy of the microbead experiment. FIG. 9 shows the highly specific interactions between microbeads loaded with either PD-1 or B7-1 Ig-fusion proteins, and HEK293 cells expressing plasma membrane localized PD-L1:mCherry fusion proteins. These experiments show that multiple proteins (e.g, PD-1 and B7-1) are amenable to microbead presentation and demonstrate the high signal-to-noise that can be expected (i.e., there is very low background binding detected with cells expressing only cytoplasmic GFP). These proof-of-principle experiments highlight the utility and power of microbead-based presentation coupled with flow cytometric analysis for defining receptor:ligand interactions. Using the same PD-L1 interactions described for the cell-microbead approach, the cell-cell flow cytometry approach is further illustrated. While microbead presentation affords enhanced avidity relative to Ig-fusion proteins, the expression of the query protein on the plasma membrane of eukaryotic cells is provides greater receptor density, significantly higher avidity and expanded dynamic range for detecting weaker receptor:ligand interactions.

Figure 10:
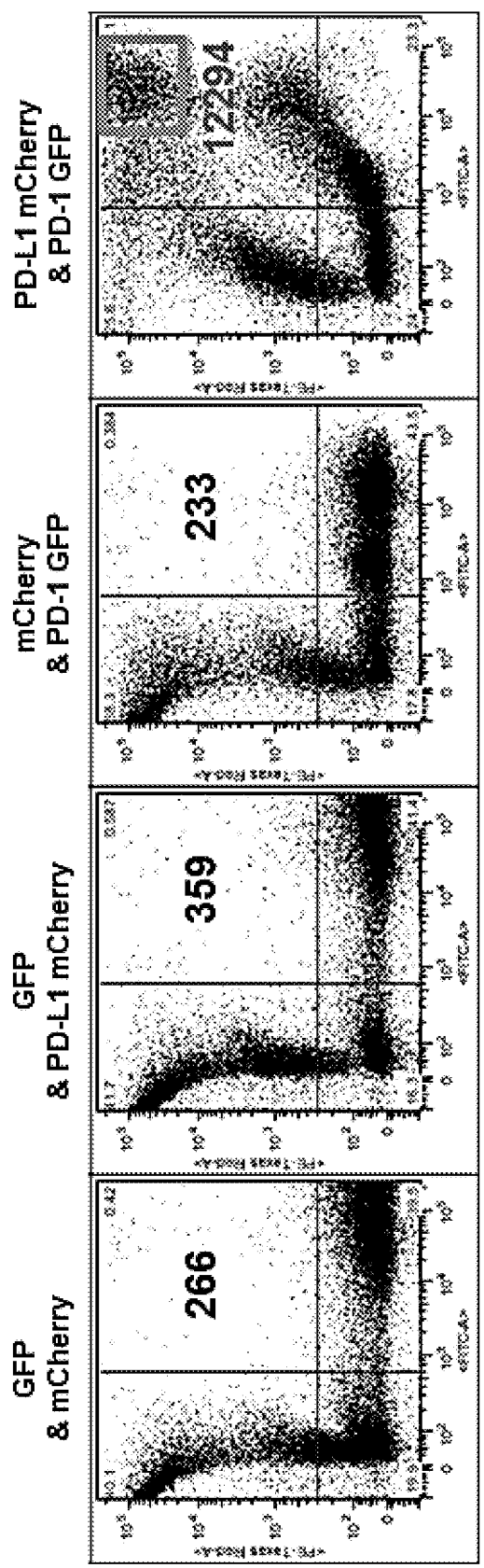
FIG. 10: Detection of specific engineered cell-cell interactions by Flow cytometry. HEK 293 cells were transfected with GFP, mCherry, PD-L1 mCherry or PD-1 GFP. Cells were resuspended in ice cold DMEM with 2% BSA and cell lines were mixed together at a 1:1 stoichiometric ratio. Individual populations and mixed binary pairs were incubated at 4° C. for two hours. A significant (~60-fold) increase in the number of red & green fluorescent events (i.e., conjugates) is only observed when both ligand and receptor are present.
Figure 11:
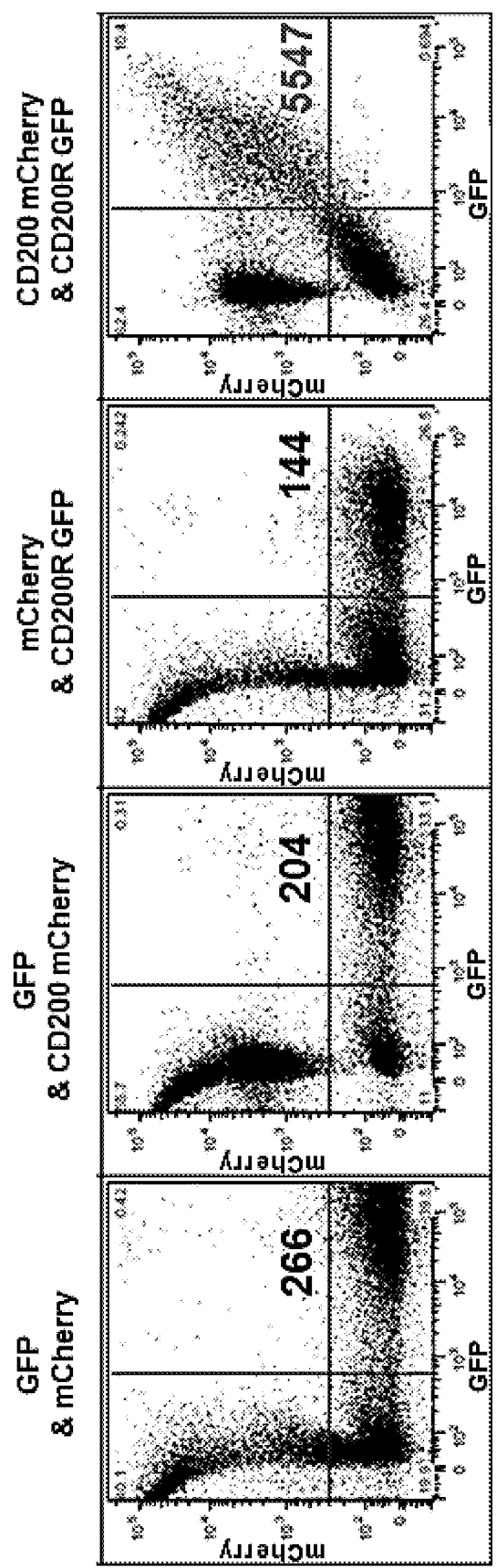
FIG. 11: Detection of CD200:CD200-Receptor Interaction by Flow Cytometry. HEK293 cells were transfected with GFP, mCherry, CD200 mCherry or CD200-Receptor GFP. Cells were processed and analyzed as in FIG. 10. A significant increase in the number of red:green fluorescent events (i.e., conjugates) is only observed when cells individually expressing both ligand and receptor are present.

The following were individually expressed in suspension-adapted HEK293 cells: 1) full-length PD-L1 as an mCherry fusion, 2) full-length PD-1 as a GFP fusion, 3) cytoplasmic mCherry and 4) cytoplasmic GFP. Flow cytometric analysis of the individual and mixed populations clearly demonstrated a significant increase (~60-fold) in signal representing specific cell-cell interactions only when cells expressing PD-1 and cells expressing PD-L1 were both present (FIG. 10). As an additional negative control PD-1 was also expressed as an mCherry fusion and as expected PD-1 does not interact with itself (data not shown). As with the microbead analysis, the cell-cell approach also demonstrated interactions between PD-L1-mCherry and B7-1-GFP from transiently transfected HEK293 cells (data not shown). This approach appears to be of general utility as it also clearly revealed the expected interaction between CD200 and CD200-Receptor (CD200R) (FIG. 11), which are unrelated to the PD-1, PD-L1, B7-1 protein families.

These flow cytometry approaches can be applied to other known T-cell costimulatory receptor:ligand pairs, including the homophilic and heterophilic interactions within the nectin family described above (FIG. 5). Both microbeads and transiently transfected HEK293 cells can be employed to challenge the method using known immune receptors to probe binding across the entire Ig superfamily, the TNF/TNFR superfamilies and ultimately extend these experiments to the probe entire Secretome.

Dissection of biochemical function: The microbead-cell and cell-cell interactions can be used to dissect complex biochemical function by screening large numbers of mutant molecules. These capabilities have been demonstrated by generating PD-L1 point mutants that exhibit a wide range of affinities for PD-1 and B7-1, and of particular importance PD-L1 point mutants that exclusively bind to either PD-1 or B7-1. These studies used the generation of HEK293 cell lines individually transiently transfected with large numbers (i.e., >100) of PD-L1 mutant-mCherry fusions. These cells were probed by flow cytometry for their ability to bind either GFP-loaded microbeads decorated with wild type PD-1 Ig-fusion or wild type B7-1 Ig-fusion proteins, or HEK293 cells transiently transfected with plasma membrane-localized wild type PD-1-GFP or B7-1-GFP fusions. Of particular note was the observation that several mutants that lacked binding in the microbead assay showed significant binding in the context of the cell-cell format (e.g, K124A and K125A) (FIG. 12). This difference is directly attributable to the enhanced valency/avidity associated with cell surface expression and underscores the value of multiple platforms with a range of avidities. These studies resulted in the generation of mutant PD-L1 Ig-fusion proteins that specifically bound either PD-1 (G119A, G120A) or B7-1 (D122A, Y123A) (FIG. 12), and provided a mapping of the distinct but overlapping PD-L1 surfaces responsible for PD-1 and B7-1 recognition (data not shown); these unique reagents permit distinct contributions of the PD-L1:PD-1 and PD-L1:B7-1 interactions to mammalian immunity to be defined. These results highlight the selectivity, utility and complementarity of the microbead-cell and cell-cell interaction platforms. Furthermore, the on-going quantitative determination of Kds for these PD-L1 mutant interactions (e.g., surface plasmon resonance) will aid in benchmarking the sensitivity of these microbead-cell and cell-cell platforms, as well as the cell microarray platform, with regard to binding affinity.

Enhanced throughput. The above performed studies were performed using a BD FacsAria III, which supports a modest throughput of ~1 sample per minute in a "one-off" fashion, requiring constant user attention. These methods can be employed on other systems, such as a 96/384-well plate format to support high-throughput screening utilizing, for example, an Intellicyt™ HTFC system. The Intellicyt™ supports a throughput of 3 minutes per 96 well plate/12 minutes per 384 in a hands-free mode. This flow cytometry-based method, when performed using a multi-well based cytometer and fully automated tissue culture robotics, provides high throughput needed for large-scale receptor de-orphaning experiments. Other examples of systems usable with the methods include Perkin Elmer Cell::Explorer; a fully automated tissue culture-based liquid handler, a Janus workstation, Liconic shaking incubator, Envision plate reader—all accessible via a six-axis robotic arm contained within a BSL-2 biosafety hood to ensure sterility, for example. Fully implemented automated tissue culture capabilities, including cell growth, media exchange, transfection, etc. aid efficiency. The platform in multi-well format can, optionally, be benchmarked against the proven interaction pairs (PD-1:PD-L1, PD-1:PD-L2, PD-L1:B7-1, CTLA-4:B7, CD200R:CD200; FIGS. 4,6,10,11), as well as the entire panel of PD-L1 mutants (FIG. 12). This can be extended to all members of the Ig Superfamily as described above and ultimately to the entire Secretome. It is important to note that while many labs have shown that cell-cell based interactions can readily be examined by FACS analysis (FIGS. 10 and 11), these efforts are all of a low throughput nature and not easily ported to an exhaustive screen conferring the advantages as described here.

Adaptation of magnetic capture technologies and next-generation sequencing for highly multiplexed identification of cell surface protein-protein interactions: Another platform described herein employs magnetic capture techniques to rapidly enrich for cell-microbead (or cell-cell) conjugates formed as a consequence of specific receptor:ligand interactions[103] and massively parallel next-generation sequencing (e.g., Illumina/454[104-106]) to deconvolute the resulting pools (e.g., [107-110]). This platform leverages a tagged expression vector for each member of the expression library, containing a unique nucleotide barcode (in the examples, 28 nucleotides, but other ranges may be used) that can be that can be amplified with "universal primers" and readily identified by deep sequencing (FIG. 13) [107-110]. The library of barcoded vectors can be pooled and transfected en masse into suspension-adapted HEK293 cells. The pooled expression library is mixed with the query protein (in the context of microbead or cell surface presentation) to form conjugates, which are recovered by multi-well magnetic separation (performing, for example, 24 parallel separations in less than 30 minutes). Although the query proteins are present in the pooled library, the magnetic query protein (in the context of microbead or cell surface presentation) is in great excess thus eliminating competition from pooled library components. The barcodes from the enriched pool members are amplified and subjected to next-generation deep sequencing (e.g., up to 10,000,000 reads of 75 nucleotides each) to identify barcodes enriched by the capture process. These enriched barcodes directly identify potential receptor:ligand interactions for subsequent validation by in vitro biochemical approaches (SPR, ITC, SEC, FACS). The strategy allows for the rapid identification of binding partners for a single query protein, but can readily be multiplexed to vastly increase throughput and reduce costs. For example, using tissue culture automation, each of the 500 members of the IgSF can be individually used as the query, with the captured conjugates from each query collected in a separate well of a multi-well plate. This physical separation of candidate interactors for each query protein, allows for "composite" primers to be used in the amplification step (i.e., each well receives a unique primer set in which the two "universal T7 priming sequences" are flanked by an additional 8 unique, well specific nucleotides). The use of composite primers allows for the specific identification of those library members (28 nucleotide core barcode) that are enriched due to interaction with the query protein corresponding to a particular well (additional well-specific nucleotide barcode, e.g. 8 nucleotides) (FIG. 13). After separate amplification of each well with these composite primers, the amplicons are pooled and deconvoluted with a single deep sequencing run. This identifies the interacting members of the library on the basis of the unique nucleotide barcode assigned to each member of the IgSF. These interactors are identified as binding partners for specific query proteins by the unique (e.g. 8 nucleotide) barcode that is specific for each well.

Figure 14A:
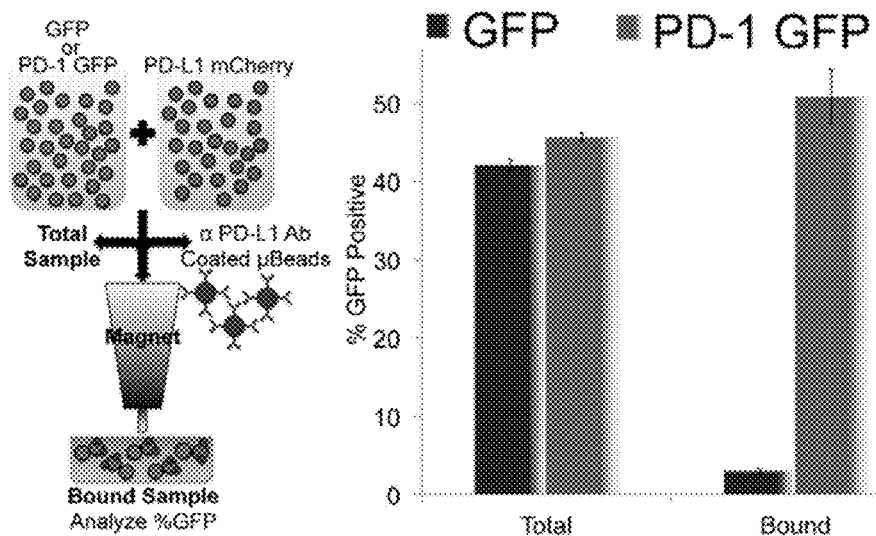
FIGS. 14A-14B: Magnetic microbeads can be used to capture and isolate specific cell-cell binding events. 14A) HEK293 cells transiently expressing PD-L1 mCherry-fusion were mixed with cells transiently expressing GFP or PD-1 GFP-fusion at a 1:1 ratio ($4 \times 10^6$ cells total). Magnetic protein A-coated microbeads (Miltenyi) decorated with a PD-L1 antibody were added and a sample was removed (Total); this represents the composition of the starting mixture). The mixture was applied to a magnetic cell separation column and the Bound cells were washed and eluted. The "Total" and "Bound" samples were analyzed by FACS to determine the percent of GFP positive cells. The PD-L1 expressing cells, captured by the magnetic beads, isolated significantly more cells expressing PD-1 GFP-fusion than cells expressing GFP alone, demonstrating clear and specific enrichment of the cognate receptor:ligand conjugates. 14B) To demonstrate the ability to isolate "rare" events, as would be encountered in high-throughput screens, $10^6$ PD-L1 mCherry cells were mixed with $0.1 \times 10^6$ cells expressing either PD-1 GFP-fusion or GFP, and $5 \times 10^6$ untransfected cells (to mimic a pseudo library). In this experiment, GFP positive cells represent ~1.5% of the total cells. After 2 hours, anti PD-L1 coated microbeads were added, "Total" samples were taken and the Bound fraction isolated as described in A. The data show significant enrichment of the PD-1 GFP-fusion expressing cells by the magnetically captured PD-L1 expressing cells.

Magnetic capture/enrichment: The use of the Miltenyi system for cell enrichment in the context of cell-microbead conjugates is straightforward [103]. The use of 50 nm magnetic beads for cell enrichment is preferred but not limiting. FIG. 14 demonstrates use of magnetic microbeads to separate/enrich specific cell-cell conjugates that form as the consequence of cognate receptor:ligand interactions. To generalize this approach for high-throughput capture of cell-cell conjugates by magnetic separations, query proteins are expressed in a cell line stably expressing a transmembrane-anchored tag (e.g. FLAG) on the surface to allow capture by anti-FLAG bearing magnetic beads. This strategy prevents the microbead-bound capture reagent (e.g., anti-FLAG) from interfering with the specific receptor:ligand complex. As such, it is possible to examine a range of library pool:query cell stoichiometries and vary the amount of magnetic beads utilized, as these variables will affect the yield and stringency of the selection. Importantly, magnetic microbead capture allows for extensive washing steps and results in reduced background. The strength of the very highly multivalent interactions associated with cell-cell conjugate formation is fully compatible with the relative gentle magnetic separation technology. This approach is not dependent on the measurement of fluorescent signals for determining "bound" and "unbound" events, and removes the complications of gating, laser settings etc.

Figure 14B:
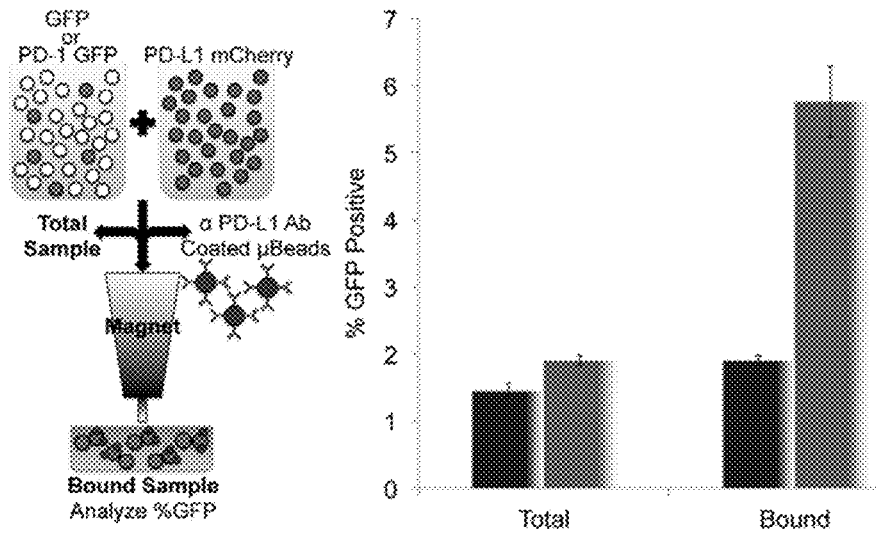
Figure 16:
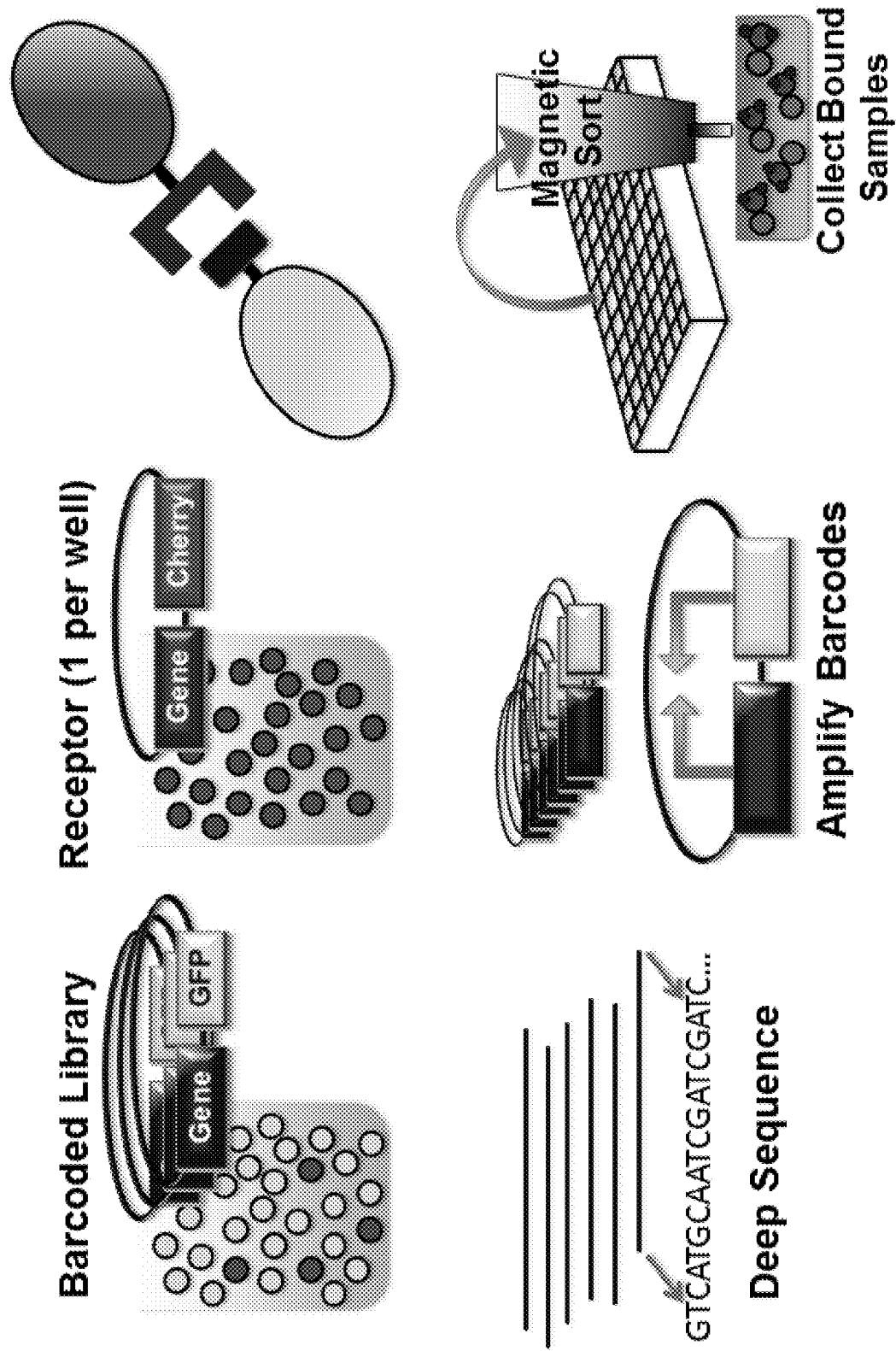
FIG. 16: Multiplexing of the Cell-Cell FACS assay: A secreted protein mammalian expression library was generated with each expression construct uniquely barcoded (variable ~20 base pair sequence on the expression plasmid, downstream of 3' end). These constructs are expressed with a GFP fluorescent protein marker. "Challenger" secreted protein expression constructs, non barcoded, are also generated, for example, with an mCherry fluorescent protein marker. The library constructs and "Challenger" constructs are expressed separately in mammalian cells. Cell populations of "library" and "challenger" are mixed together. Cell-cell interactions are then sorted from non interacting cells. The sorting can be performed by fluorescence (i.e. sorting all double positive events, mCherry+GFP) or magnetically using magnetic beads to capture all the "challenger" cells along with any bound library partners. Cell samples are taken pre and post sorting, lysed and the supernatant used for PCR amplification of the expression plasmids. Pooled PCR samples are sent for Deep Sequencing, which provides a quantitative assessment of the how many copies of a particular barcode (GTCATGCAATCGATCGATC (SEQ ID NO: 2)) are present. In our experiments an enrichment of a specific barcode over background would be indicative of a specific protein-protein interaction. We can then use the specific barcode sequence to identify what that protein is from the library.
Figures 18A, 18B:
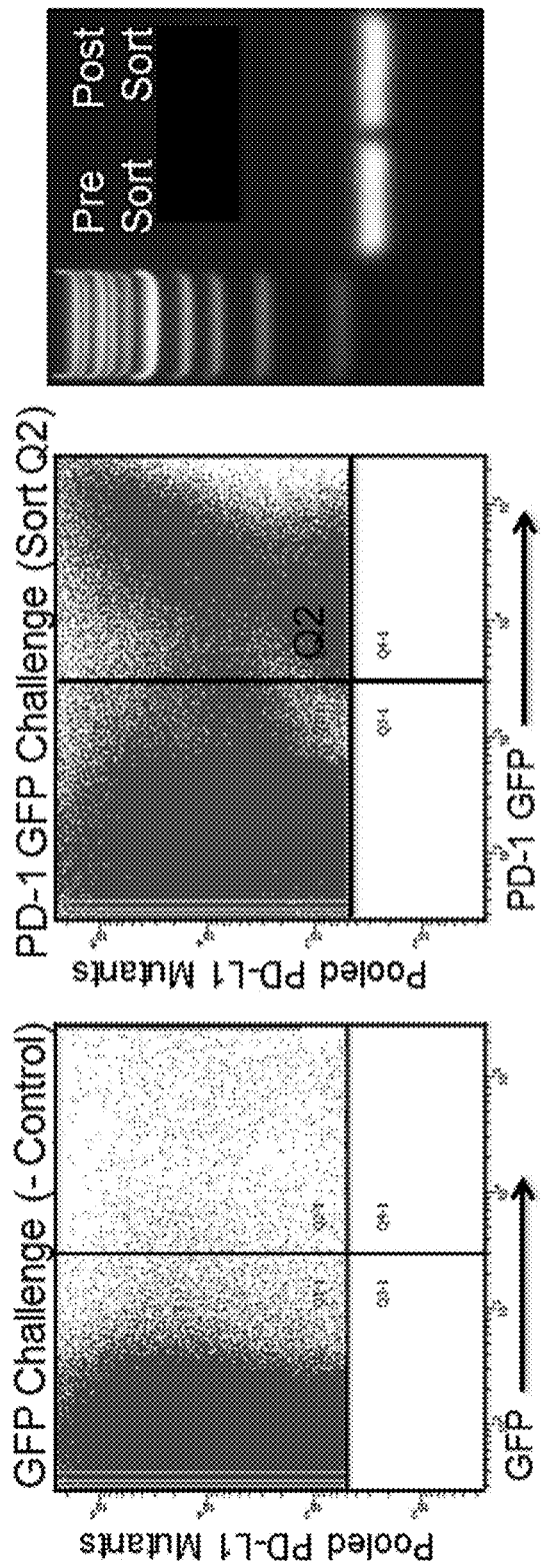
FIGS. 18A-18B: PD-L1 Mutants: A Test Case—18A) The sequence shown is for part of the mouse PD-L1 gene (DNA sequence (SEQ ID NO: 3), amino acid sequence (SEQ ID NO; 4)). Amino acids highlighted show the locations of the unique point mutations. Green are residues that, when mutated show NO EFFECT ON BINDING to PD-1. Red residues are those that when mutated show STRONG LOSS OF BINDING to PD-1 and yellow residues show more MODEST LOSS OF BINDING to PD-1. The DNA sequence highlighted in blue shows the location of the primers used to PCR amplify the pooled PD-L1 library both pre and post sorting. 18B) The FACS panels show a negative control mock sort using GFP to challenge the PD-L1 mutant library and the experimental PD-1 challenge sort. For the experiment, 20,000 cells were collected prior to sorting (Pre Sort) and from the sorted population Q2 (Post Sort), and PCR amplified using the primers highlighted above. The agarose gel image on the lower right shows the PCR products obtained from the pre- and post-sort samples. These samples were then sent for deep sequencing analysis.
Figure 19:
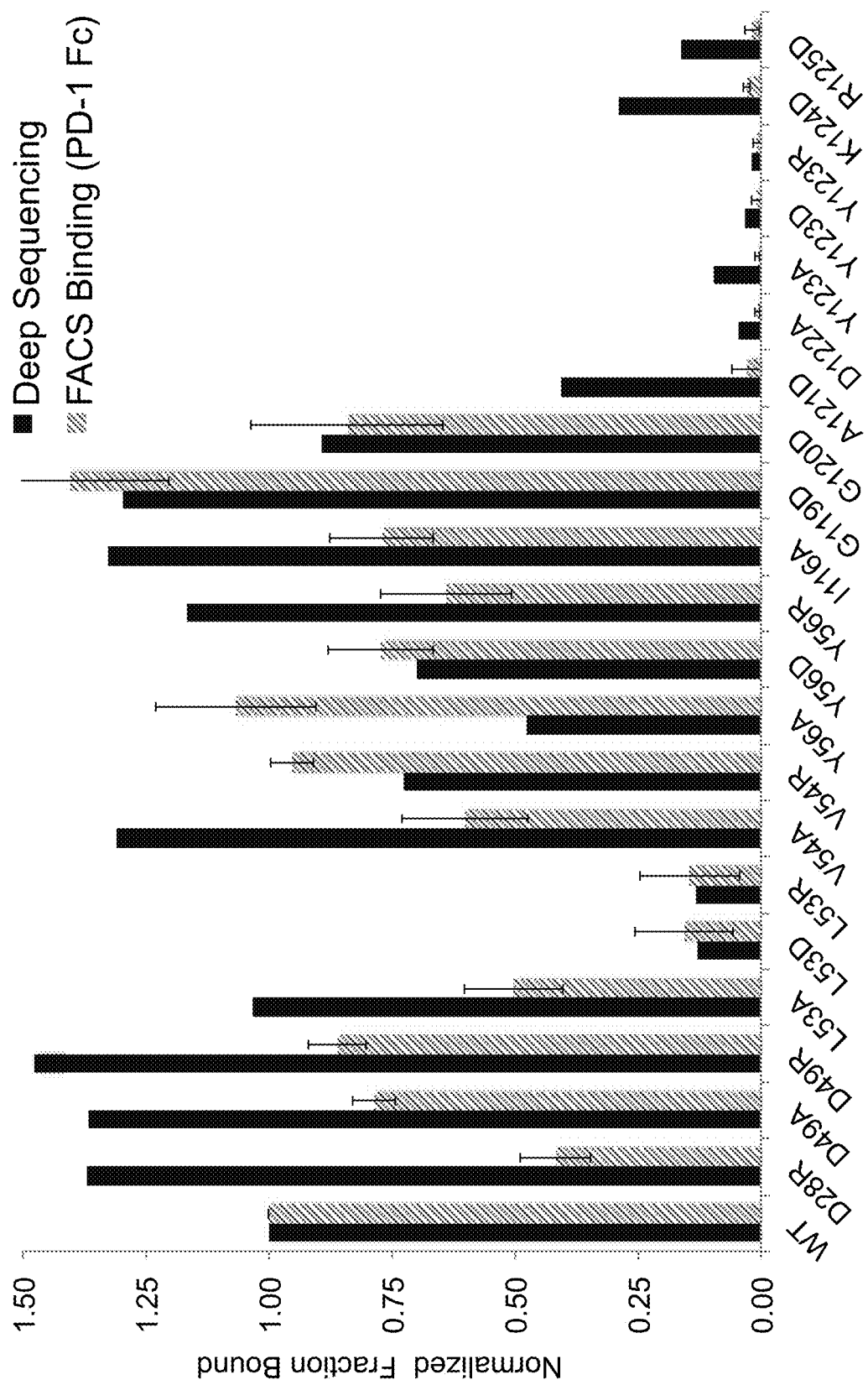
FIG. 19: The deep sequencing results were analyzed to determine how many times each unique PD-L1 sequence was identified (total # of occurrences). The enrichment ratio was then calculated in the occurrence between the pre- and post-sort samples. For example, if in the pre-sort sample 10 wild-type PD-L1 sequences were counted and in the post sort sample 100 were counted, a 10-fold enrichment of wild-type PD-L1 was observed (100 divided by 10). If a specific PD-L1 mutant does not bind PD-1, for example D122A, then we might still count 10 D122A sequences in the pre sort sample but only count 5 sequences in the post sort sample. This gives an enrichment ratio of 0.5 (5 divided by 10). In order to compare the data to that obtained using our traditional FACS binding method (light blue bars) all the data was normalized to wild-type PD-L1 binding. The data clearly demonstrates that those mutants previously identified as poor PD-1 binders were similarly identified using the multiplexed deep sequence approach.
Figure 20:
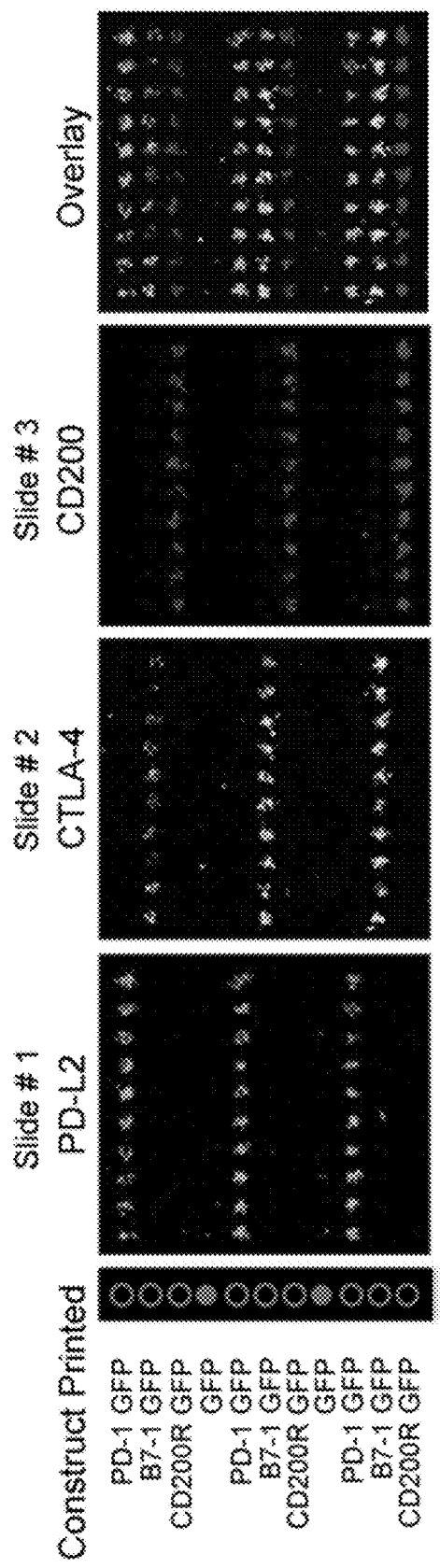
FIG. 20: Detection of T-cell Ligand—Receptor binding using the cell microarray platform described herein has been used to examine several IgSF receptor/ligand pairs. Binding is specific.
Figure 21:
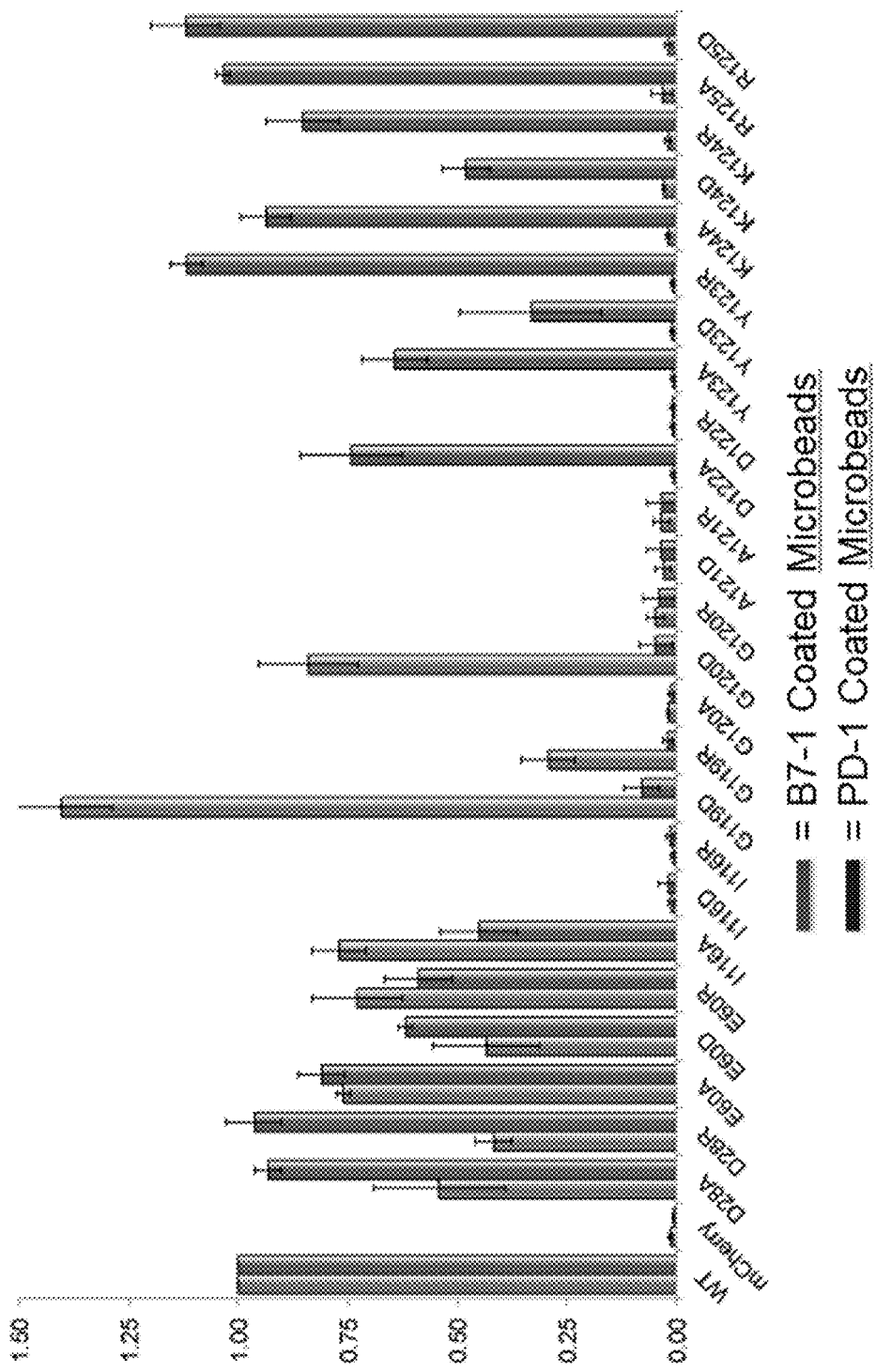
FIG. 21: Use of the microbead platform to identify PD-L1 mutants with selective function.
Figure 22:
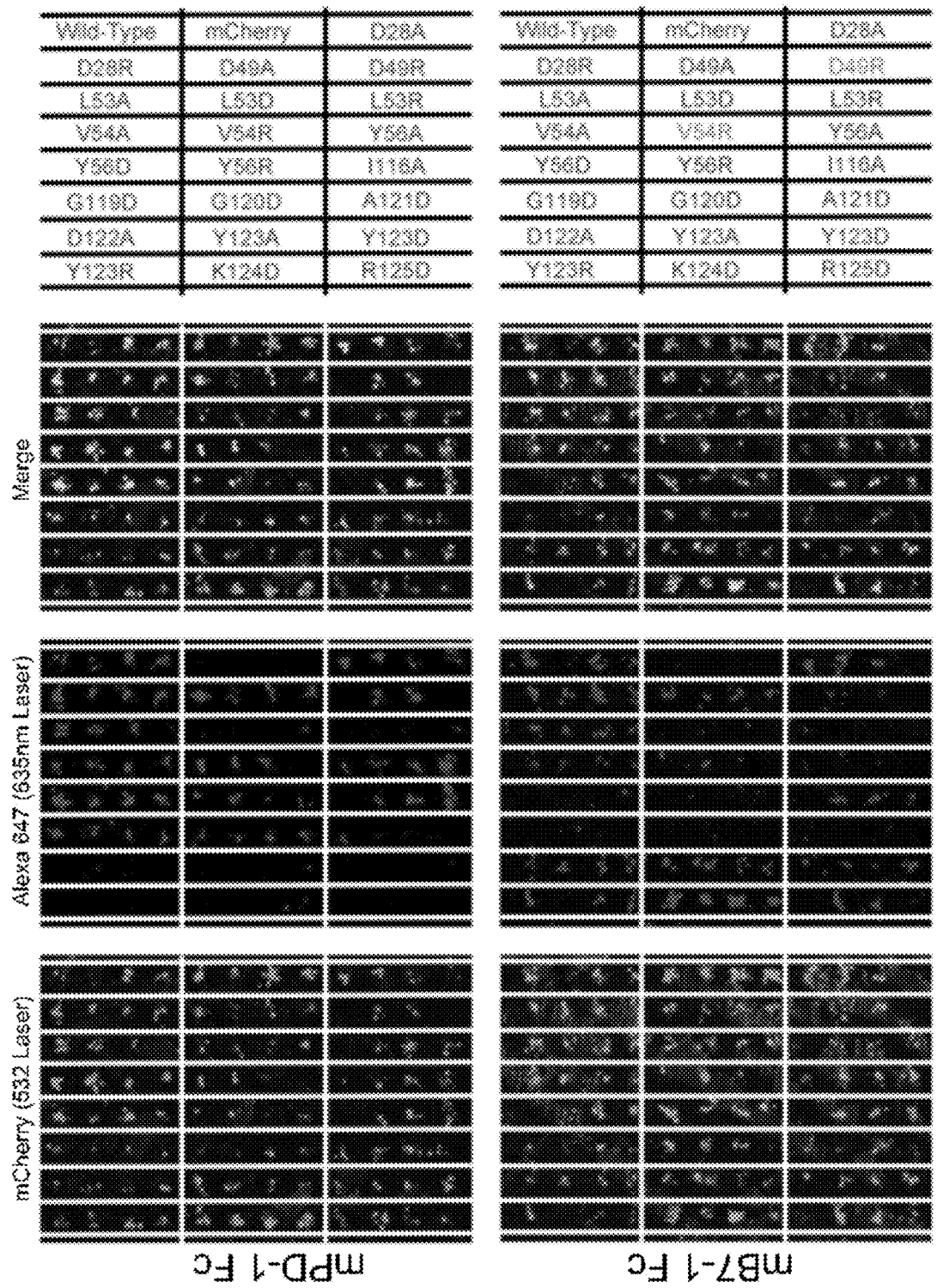
FIG. 22: Glass slides were printed with plasmid DNA encoding, wild-type PD-L1, mCherry alone, or a series of PD-L1 mutants. The locations of each printed construct are shown on the diagram to the far right. The fluorescent signal from the mCherry (Cy3) laser reports the expression level of each printed construct. The Alexa 647 (Cy5) laser shows binding of either PD-1 (top panel) or B7-1 (lower panel) Fc fusion protein to the PD-L1 expressing cells. Therefore spots that are not fluorescent in the Cy5 channel do not show binding. The grids to the right are color coded to indicate the binding observed using the microbead binding experiment. Those constructs in green showed binding similar to wild-type. Yellow mutants showed reduced binding and red mutants showed little to no binding. An identical pattern of binding is observed on the microarrays.
Figure 23B:
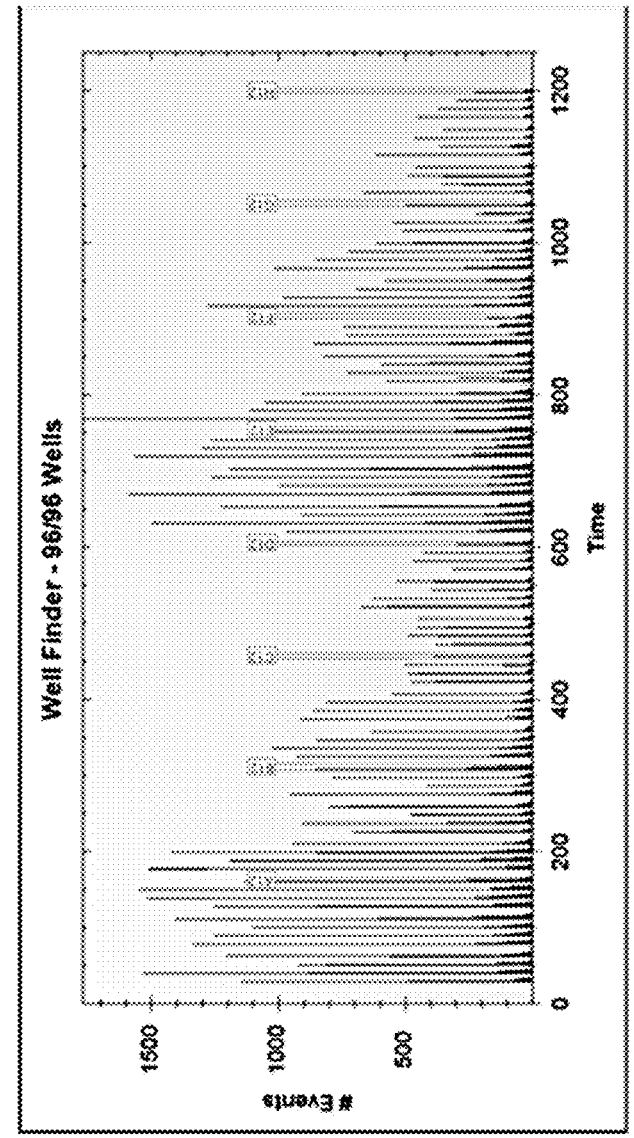
Figure 23C:
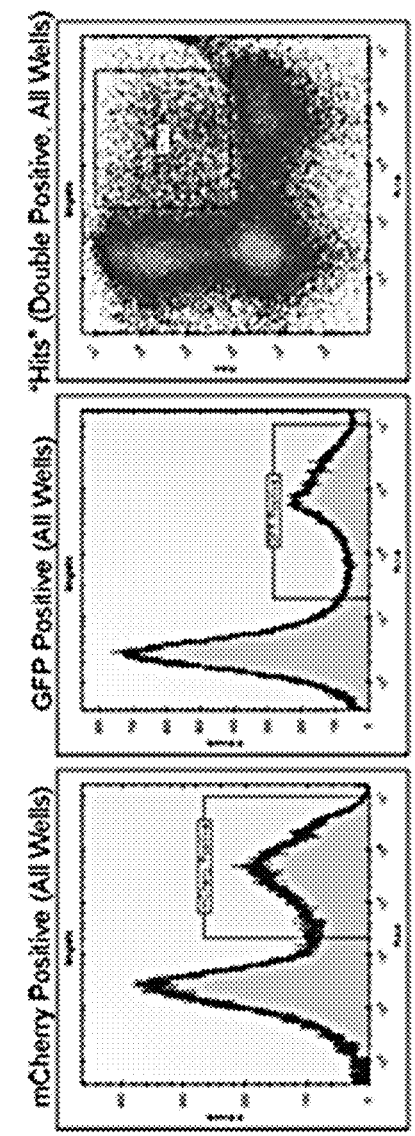
Figure 23D:
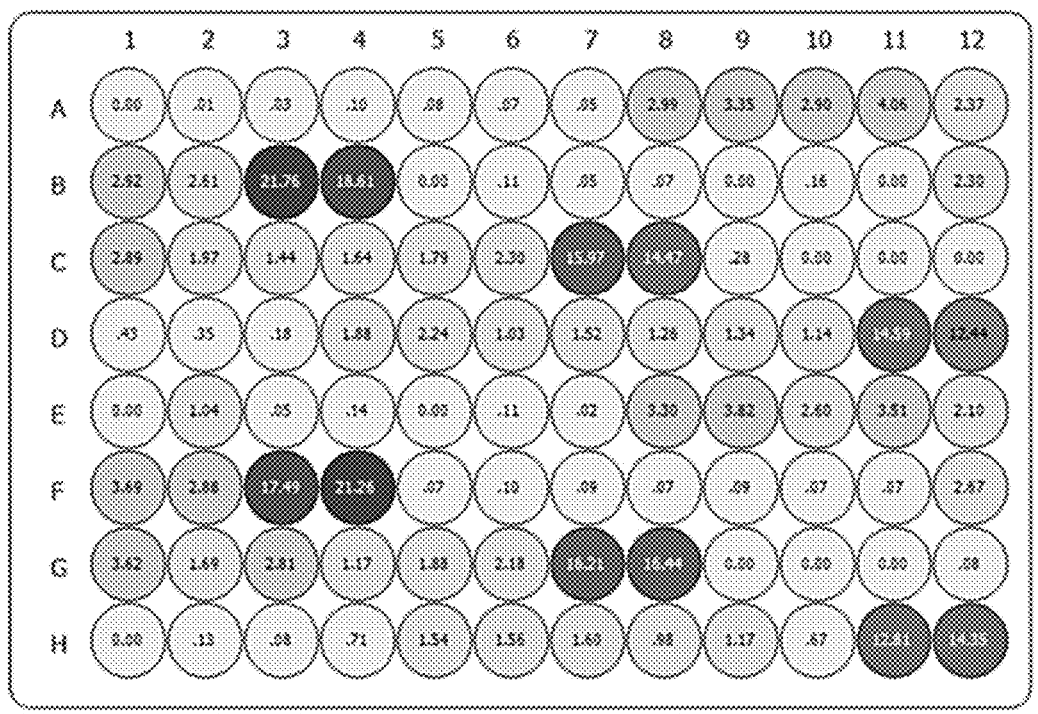
Figure 23E:
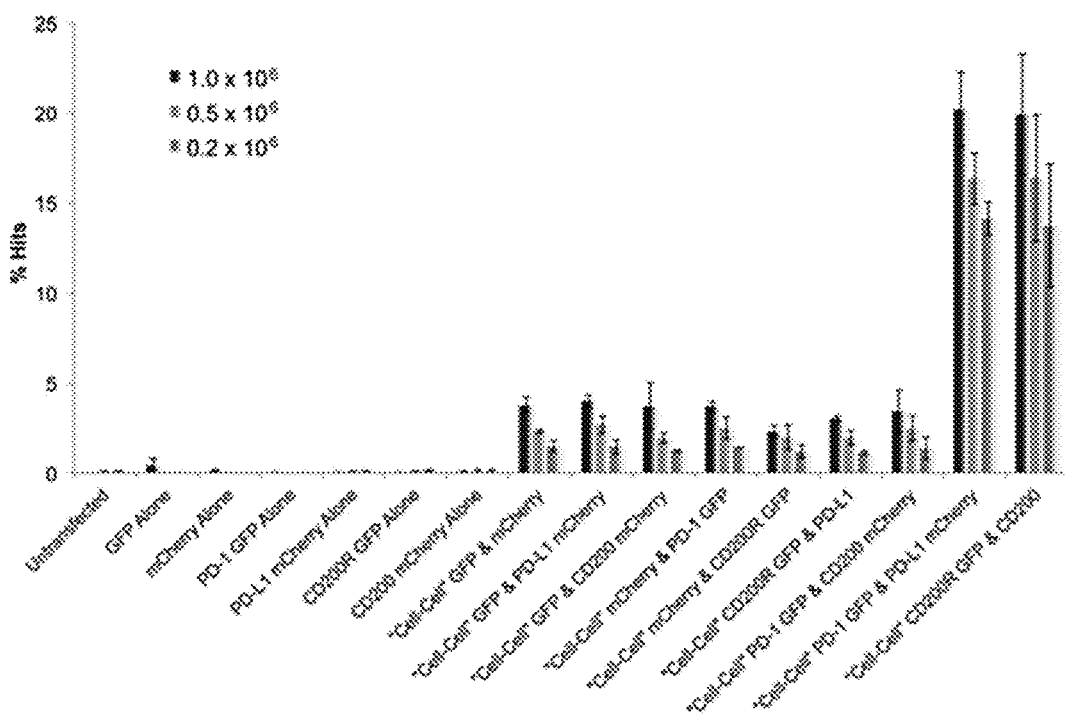
Figure 24A:
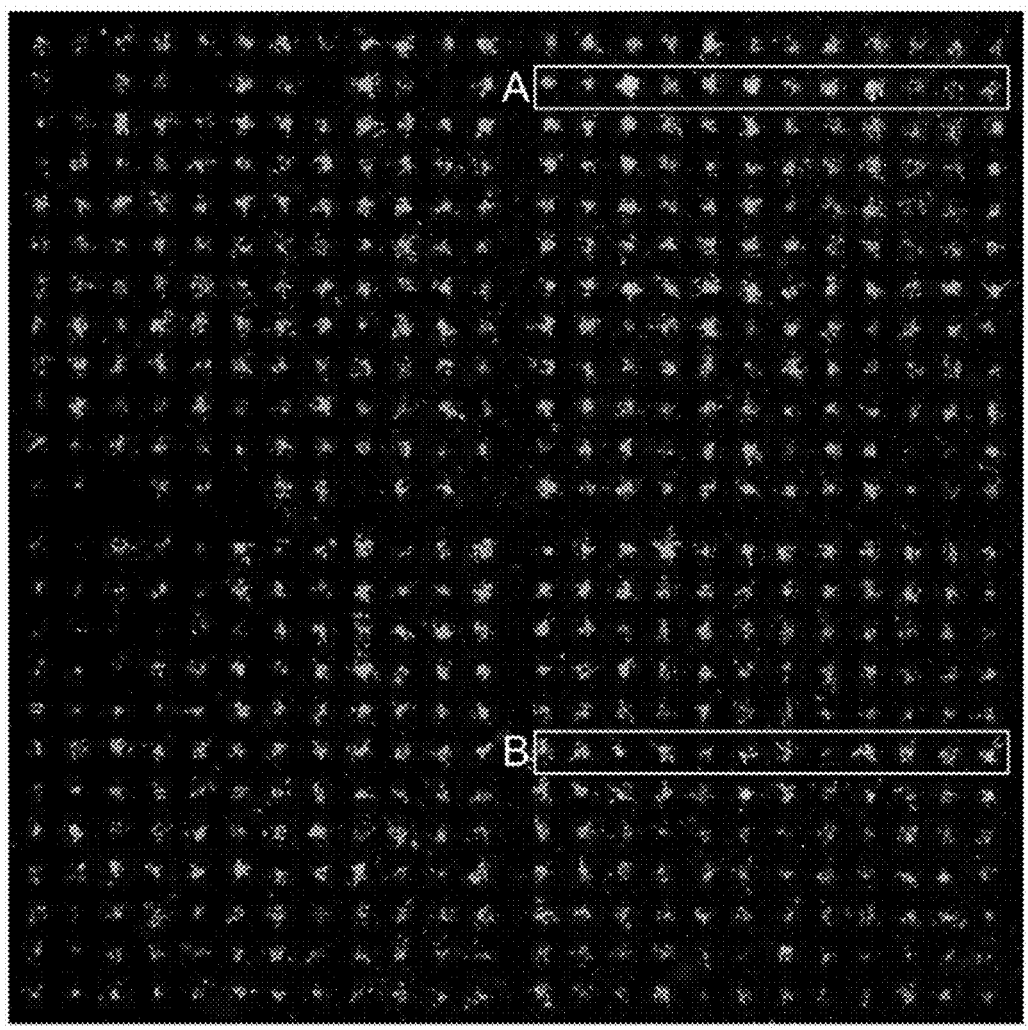
FIGS. 24A-24B: Cell microarray expressing members of the IgG superfamily. 24A) Poly-1-lysine coated glass slides were printed with expression constructs for 144 human genes in the IgG superfamily. Each construct was printed in 4 replicates across a row resulting in a total array of 4×144 spots. After transfection the expression of each construct printed can be observed directly via mCherry fluorescence (pseudocolored green, single channel not shown). This cell array was subsequently treated with recombinant PD-L1-Fc pre-incubated with Alexa 647 labeled anti-human IgG, washed and fixed with 4% formaldehyde (pseudocolored red, single channel not shown). Data shows the overlaid green and red pseudocolored images where binding is observed as a yellow/orange color that results from the merging of the green and red fluorescence signals. The rows labeled A and B contain the two known binding targets of PD-L1, PD-1 (A) and B7-1 (B). 24B) 10× magnification of the rows highlighted in A showing the positive signal observed for PD-L1 binding to PD-1 and B7-1 compared to the signal observed from the surrounding spots.
Figure 24B:
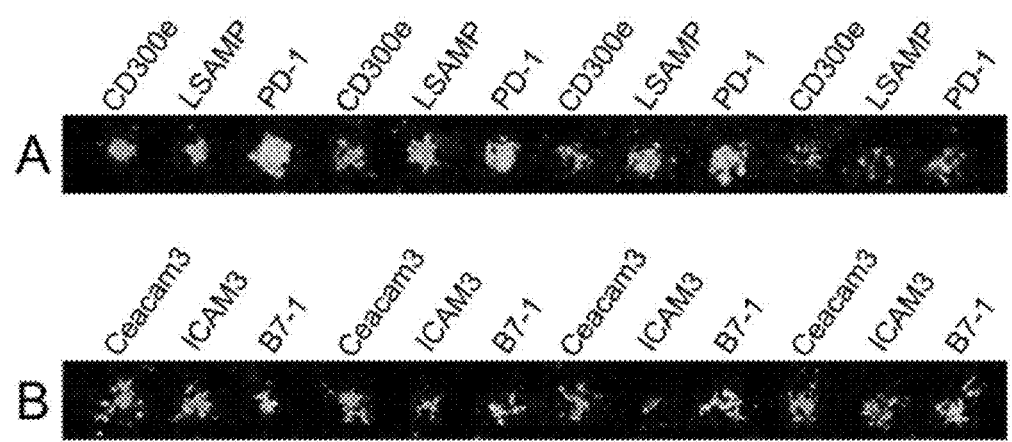

Signal-to-noise: Non-specific binding can occur between the query-expressing cell line and "off-targets" (i.e., cells not expressing a cognate ligand). FIG. 14B demonstrates the ability of the magnetic capture technology to specifically enrich for "rare events" (i.e., 1.5% of total possible interactions). FIG. 15 provides proof that the barcode approach is capable of detecting even more rare events. For typical binary cell-cell assays where the population is composed of a 1:1 mixture of cells expressing cognate receptor:ligand pairs (e.g., PD-1:PD-L1 and CD200:CD200R), 10-30% of events are typically scored as positive binding interactions (see FIGS. 10 and 11). For negative controls (e.g., GFP and mCherry), typically ~0.2-0.5% of events are scored as bound, where "bound" is defined as the number events that are both GFP and mCherry positive (i.e., FIG. 15A, Quadrant 2).

To specifically assess the challenges associated with identifying cognate interactions in the context of the expression library, background was simulated by mixing $10^7$ HEK293 cells transiently expressing GFP with $0.02 \times 10^6$ cells expressing PD-1 GFP-fusion (0.2% of the GFP positive cells, which would represent a single member of the IgSF if all transfected with equal efficiency). This library was challenged with $10^6$ mCherry (negative control) or PD-L1 mCherry-fusion transiently expressing HEK293 cells. FIG. 15 demonstrates the clear enrichment of GFP:mCherry conjugates due to the specific PD-1:PD-L1 interaction (Quadrant 2). Importantly, the PCR-based validation of the enrichment of the PD-1 expressing cells is completely analogous to the barcoding strategy implemented to deconvolute the pooled amplicons (i.e., the PD-1 coding sequence acts as an intrinsic barcode). Importantly, the levels of enrichment achieved in FIGS. 14 and 15 are fully within the detection limits of the next-generation deep sequencing approaches being employed[113].

The PD-L1:PD-1 and PD-L1:B7-1 interactions can be examined with the unique barcode approach described in FIG. 13, as can the 500 genes belonging to the human IgSF incorporated into each of the two expression vectors (i.e., 500 receptors, 500 ligands) and subjected to interaction screening. This system enables the concurrent query of many ligands against the entire panel of potential receptors, allowing for the simultaneous, efficient and cost effective interrogation of large query lists. This approach can cover the entire Secretome.

Further aspects of the invention, and validation thereof, are demonstrated in FIGS. 16-24.

REFERENCES

1. Cheung, T. C., et al., *T cell intrinsic heterodimeric complexes between HVEM and BTLA determine receptivity to the surrounding microenvironment*. J Immunol, 2009. 183(11): p. 7286-96.
2. Cheung, T. C., et al., *Unconventional ligand activation of herpesvirus entry mediator signals cell survival*. Proc Natl Acad Sci USA, 2009. 106(15): p. 6244-9.
3. Olszewski, M. B., et al., *TNF trafficking to human mast cell granules: mature chain-dependent endocytosis*. J Immunol, 2007. 178(9): p. 5701-9.
4. Giebing, G., et al., *Arrestin-independent internalization and recycling of the urotensin receptor contribute to long-lasting urotensin II-mediated vasoconstriction*. Circ Res, 2005. 97(7): p. 707-15.
5. Tarasova, N. I., et al., *Visualization of G protein-coupled receptor trafficking with the aid of the green fluorescent protein. Endocytosis and recycling of cholecystokinin receptor type A*. J Biol Chem, 1997. 272(23): p. 14817-24.
6. Bohme, I. and A. G. Beck-Sickinger, *Illuminating the life of GPCRs*. Cell Commun Signal, 2009. 7: p. 16.
7. Carman, C. V. and T. A. Springer, *Integrin avidity regulation: are changes in affinity and conformation underemphasized?* Curr Opin Cell Biol, 2003. 15(5): p. 547-56.
8. Chiu, C. S., et al., *Number, density, and surface/cytoplasmic distribution of GABA transporters at presynaptic structures of knock-in mice carrying GABA transporter subtype 1-green fluorescent protein fusions*. J Neurosci, 2002. 22(23): p. 10251-66.
9. Geng, H., et al., *Soluble form of T cell Ig mucin 3 is an inhibitory molecule in T cell-mediated immune response*. J Immunol, 2006. 176(3): p. 1411-20.
10. Sakimoto, T., A. Yamada, and M. Sawa, *Release of soluble tumor necrosis factor receptor 1 from corneal epithelium by TNF-alpha-converting enzyme-dependent ectodomain shedding*. Invest Ophthalmol Vis Sci, 2009. 50(10): p. 4618-21.
11. Sanderson, M. P., et al., *Generation of novel, secreted epidermal growth factor receptor (EGFR/ErbB1) isoforms via metalloprotease-dependent ectodomain shedding and exosome secretion*. J Cell Biochem, 2008. 103 (6): p. 1783-97.
12. Chalaris, A., et al., *The soluble Interleukin 6 receptor: generation and role in inflammation and cancer*. Eur J Cell Biol, 2011. 90(6-7): p. 484-94.
13. Shibata, M. A., et al., *The endogenous soluble VEGF receptor-2 isoform suppresses lymph node metastasis in a mouse immunocompetent mammary cancer model*. BMC Med, 2010. 8: p. 69.
14. Pavlakovic, H., et al., *Soluble VEGFR-2: an antilymphangiogenic variant of VEGF receptors*. Ann N Y Acad Sci, 2010. 1207 Suppl 1: p. E7-15.
15. Khankin, E. V., et al., *Soluble erythropoietin receptor contributes to erythropoietin resistance in end-stage renal disease*. PLoS One, 2010. 5(2): p. e9246.
16. Jones, D. C., et al., *Alternative mRNA splicing creates transcripts encoding soluble proteins from most LILR genes*. Eur J Immunol, 2009. 39(11): p. 3195-206.

17. Chen, Z., et al., *Identification of an expressed truncated form of CD200, CD200tr, which is a physiologic antagonist of CD200-induced suppression.* Transplantation, 2008. 86(8): p. 1116-24.
18. Eshel, D., et al., *Characterization of natural human antagonistic soluble CD40 isoforms produced through alternative splicing.* Mol Immunol, 2008. 46(2): p. 250-7.
19. Levine, S. J., *Molecular mechanisms of soluble cytokine receptor generation.* J Biol Chem, 2008. 283(21): p. 14177-81.
20. Yang, Y., et al., *A novel method to incorporate bioactive cytokines as adjuvants on the surface of virus particles.* J Interferon Cytokine Res, 2009. 29(1): p. 9-22.
21. Cao, E., et al., *T cell immunoglobulin mucin-3 crystal structure reveals a galectin-9-independent ligand-binding surface.* Immunity, 2007. 26(3): p. 311-21.
22. Bitonti, A. J., et al., *Pulmonary delivery of an erythropoietin Fc fusion protein in non-human primates through an immunoglobulin transport pathway.* Proc Natl Acad Sci USA, 2004. 101(26): p. 9763-8.
23. Ozkaynak, E., et al., *Programmed death-1 targeting can promote allograft survival.* J Immunol, 2002. 169(11): p. 6546-53.
24. Yang, T., et al., *A variant of TNFR2-Fc fusion protein exhibits improved efficacy in treating experimental rheumatoid arthritis.* PLoS Comput Biol, 2010. 6(2): p. e1000669.
25. Moreland, L., G. Bate, and P. Kirkpatrick, *Abatacept.* Nat Rev Drug Discov, 2006. 5(3): p. 185-6.
26. Vincenti, F., A. Dritselis, and P. Kirkpatrick, *Belatacept.* Nat Rev Drug Discov, 2011. 10(9): p. 655-6.
27. Moreland, L. W., *Soluble tumor necrosis factor receptor (p75) fusion protein (ENBREL) as a therapy for rheumatoid arthritis.* Rheum Dis Clin North Am, 1998. 24(3): p. 579-91.
28. Zhang, X., et al., *Structural and functional analysis of the costimulatory receptor programmed death-1.* Immunity, 2004. 20(3): p. 337-47.
29. Bhatia, S., et al., *Different cell surface oligomeric states of B7-1 and B7-2: implications for signaling.* Proc Natl Acad Sci USA, 2005. 102(43): p. 15569-74.
30. Cao, E., et al., *NTB-A receptor crystal structure: insights into homophilic interactions in the signaling lymphocytic activation molecule receptor family.* Immunity, 2006. 25(4): p. 559-70.
31. Chattopadhyay, K., et al., *Structural basis of inducible costimulator ligand costimulatory function: determination of the cell surface oligomeric state and functional mapping of the receptor binding site of the protein.* J Immunol, 2006. 177(6): p. 3920-9.
32. Chattopadhyay, K., et al., *Assembly and structural properties of glucocorticoid-induced TNF receptor ligand: Implications for function.* Proc Natl Acad Sci USA, 2007. 104(49): p. 19452-7.
33. Yan, Q., et al., *Structure of CD84 provides insight into SLAM family function.* Proc Natl Acad Sci USA, 2007. 104(25): p. 10583-8.
34. Chattopadhyay, K., et al., *Evolution of GITRL immune function: murine GITRL exhibits unique structural and biochemical properties within the TNF superfamily.* Proc Natl Acad Sci USA, 2008. 105(2): p. 635-40.
35. Lazar-Molnar, E., et al., *Crystal structure of the complex between programmed death-1 (PD-1) and its ligand PD-L2.* Proc Natl Acad Sci USA, 2008. 105(30): p. 10483-8.
36. Zhan, C., et al., *Biochemical and structural characterization of the human TL1A ectodomain.* Biochemistry, 2009. 48(32): p. 7636-45.
37. Bhatia, S., et al., *Dynamic equilibrium of B7-1 dimers and monomers differentially affects immunological synapse formation and T cell activation in response to TCR/CD28 stimulation.* J Immunol, 2010. 184(4): p. 1821-8.
38. Zhan, C., et al., *Decoy strategies: the structure of TL1A:DcR3 complex.* Structure, 2011. 19(2): p. 162-71.
39. Samanta, D., et al., *Structure of Nectin-2 reveals determinants of homophilic and heterophilic interactions that control cell-cell adhesion.* Proc Natl Acad Sci USA, 2012. 109(37): p. 14836-40.
40. Eads, J. C., et al., *Structure determination and characterization of Saccharomyces cerevisiae profilin.* Biochemistry, 1998. 37(32): p. 11171-81.
41. Bour-Jordan, H., et al., *Intrinsic and extrinsic control of peripheral T-cell tolerance by costimulatory molecules of the CD28/B7 family.* Immunol Rev, 2011. 241(1): p. 180-205.
42. Nurieva, R. I., X. Liu, and C. Dong, *Yin-Yang of costimulation: crucial controls of immune tolerance and function.* Immunol Rev, 2009. 229(1): p. 88-100.
43. Wang, S. and L. Chen, *T lymphocyte co-signaling pathways of the B7-CD28 family.* Cell Mol Immunol, 2004. 1(1): p. 37-42.
44. Zang, X. and J. P. Allison, *The B7 family and cancer therapy: costimulation and coinhibition.* Clin Cancer Res, 2007. 13(18 Pt 1): p. 5271-9.
45. Chattopadhyay, K., et al., *Sequence, structure, function, immunity: structural genomics of costimulation.* Immunol Rev, 2009. 229(1): p. 356-86.
46. Ostrov, D. A., et al., *Structure of murine CTLA-4 and its role in modulating T cell responsiveness.* Science, 2000. 290(5492): p. 816-9.
47. Schwartz, J. C., et al., *Structural basis for co-stimulation by the human CTLA-4/B7-2 complex.* Nature, 2001. 410 (6828): p. 604-8.
48. Zhang, X., et al., *Crystal structure of the receptor-binding domain of human B7-2: insights into organization and signaling.* Proc Natl Acad Sci USA, 2003. 100(5): p. 2586-91.
49. Butte, M. J., et al., *Programmed death-1 ligand 1 interacts specifically with the B7-1 costimulatory molecule to inhibit T cell responses.* Immunity, 2007. 27(1): p. 111-22.
50. Yao, S., et al., *B7-h2 is a costimulatory ligand for CD28 in human.* Immunity, 2011. 34(5): p. 729-40.
51. Mansh, M., *Ipilimumab and cancer immunotherapy: a new hope for advanced stage melanoma.* Yale J Biol Med, 2011. 84(4): p. 381-9.
52. Bluestone, J. A., E. W. St Clair, and L. A. Turka, *CTLA4Ig: bridging the basic immunology with clinical application.* Immunity, 2006. 24(3): p. 233-8.
53. Larsen, C. P., et al., *Rational development of LEA29Y (belatacept), a high-affinity variant of CTLA4-Ig with potent immunosuppressive properties.* Am J Transplant, 2005. 5(3): p. 443-53.
54. Lum, G. and X. J. Min, *FunSecKB: the Fungal Secretome KnowledgeBase.* Database (Oxford), 2011. 2011: p. bar001.
55. Mishra, S. K., H. R. Siddique, and M. Saleem, *S100A4 calcium-binding protein is key player in tumor progression and metastasis: preclinical and clinical evidence.* Cancer Metastasis Rev, 2011.

56. Nickel, W., *The unconventional secretory machinery of fibroblast growth factor 2*. Traffic, 2011. 12(7): p. 799-805.
57. Kadono, N., et al., *The impact of extracellular syntaxin4 on HaCaT keratinocyte behavior*. Biochem Biophys Res Commun, 2012. 417(4): p. 1200-5.
58. Rawat, P., et al., *The multifunctional glycolytic protein glyceraldehyde-3-phosphate dehydrogenase (GAPDH) is a novel macrophage lactoferrin receptor*. Biochem Cell Biol, 2012. 90(3): p. 329-38.
59. Kumar, S., et al., *Characterization of glyceraldehyde-3-phosphate dehydrogenase as a novel transferrin receptor*. Int J Biochem Cell Biol, 2012. 44(1): p. 189-99.
60. Nickel, W., *Pathways of unconventional protein secretion*. Curr Opin Biotechnol, 2010. 21(5): p. 621-6.
61. Prudovsky, I., et al., *Secretion without Golgi*. J Cell Biochem, 2008. 103(5): p. 1327-43.
62. Bushell, K. M., et al., *Large-scale screening for novel low-affinity extracellular protein interactions*. Genome Res, 2008. 18(4): p. 622-30.
63. Jiang, L. and A. N. Barclay, *Identification of leucocyte surface protein interactions by high-throughput screening with multivalent reagents*. Immunology, 2010. 129(1): p. 55-61
64. Gonzalez, L. C., et al., *A coreceptor interaction between the CD28 and TNF receptor family members B and T lymphocyte attenuator and herpesvirus entry mediator*. Proc Natl Acad Sci USA, 2005. 102(4): p. 1116-21.
65. Yu, X., et al., *The surface protein TIGIT suppresses T cell activation by promoting the generation of mature immunoregulatory dendritic cells*. Nat Immunol, 2009. 10(1): p. 48-57.
66. Ramani, S. R., et al., *A secreted protein microarray platform for extracellular protein interaction discovery*. Anal Biochem, 2012. 420(2): p. 127-38.
67. Lin, H., et al., *Discovery of a cytokine and its receptor by functional screening of the extracellular proteome*. Science, 2008. 320(5877): p. 807-11.
68. Palmer, E., *Cell-based microarrays: overview*. Methods Mol Biol, 2011. 706: p. 1-12.
69. Ziauddin, J. and D. M. Sabatini, *Microarrays of cells expressing defined cDNAs*. Nature, 2001. 411(6833): p. 107-10.
70. Takai, Y., et al., *Nectins and nectin-like molecules: roles in contact inhibition of cell movement and proliferation*. Nat Rev Mol Cell Biol, 2008. 9(8): p. 603-15.
71. Takai, Y., et al., *The immunoglobulin-like cell adhesion molecule nectin and its associated protein afadin*. Annu Rev Cell Dev Biol, 2008. 24: p. 309-42.
72. Chan, C. J., D. M. Andrews, and M. J. Smyth, *Receptors that interact with nectin and nectin-like proteins in the immunosurveillance and immunotherapy of cancer*. Curr Opin Immunol, 2012. 24(2): p. 246-51.
73. Wang, X., et al., *Blockade of both B7-H4 and CTLA-4 co-signaling pathways enhances mouse islet allograft survival*. Islets, 2012. 4(4).
74. Yi, K. H. and L. Chen, *Fine tuning the immune response through B7-H3 and B7-H4*. Immunol Rev, 2009. 229(1): p. 145-51.
75. Mirza, N. and D. Gabrilovich, *Comment on "Cutting edge: induction of B7-H4 on APCs through IL-10: novel suppressive mode for regulatory T cells"*. J Immunol, 2007. 178(8): p. 4705-6; author reply 4706.
76. Krambeck, A. E., et al., *B7-H4 expression in renal cell carcinoma and tumor vasculature: associations with cancer progression and survival*. Proc Natl Acad Sci USA, 2006. 103(27): p. 10391-6.
77. Sica, G. L., et al., *B7-H4, a molecule of the B7 family, negatively regulates T cell immunity*. Immunity, 2003. 18(6): p. 849-61.
78. Wei, J., et al., *Tissue-specific expression of B7x protects from CD4 T cell-mediated autoimmunity*. J Exp Med, 2011. 208(8): p. 1683-94.
79. Zang, X., et al., *B7-H3 and B7x are highly expressed in human prostate cancer and associated with disease spread and poor outcome*. Proc Natl Acad Sci USA, 2007. 104(49): p. 19458-63.
80. Zang, X., et al., *B7x: a widely expressed B7 family member that inhibits T cell activation*. Proc Natl Acad Sci USA, 2003. 100(18): p. 10388-92.
81. Wang, L., et al., *VISTA, a novel mouse Ig superfamily ligand that negatively regulates T cell responses*. J Exp Med, 2011. 208(3): p. 577-92.
82. Sun, Y., et al., *B7-H3 and B7-H4 expression in non-small-cell lung cancer*. Lung Cancer, 2006. 53(2): p. 143-51.
83. Fauci, J. M., et al., *A review of B7-H3 and B7-H4 immune molecules and their role in ovarian cancer*. Gynecol Oncol, 2012. 127(2): p. 420-5.
84. Guo, G., et al., *The characteristic expression of B7-H3 and B7-H4 in liver biopsies from patients with HBV-related acute-on-chronic liver failure*. Pathol Int, 2012. 62(10): p. 665-74.
85. Guo, G., et al., *The expression and distribution of immunomodulatory proteins B7-H1, B7-DC, B7-H3, and B7-H4 in rheumatoid synovium*. Clin Rheumatol, 2012. 31(2): p. 271-81.
86. Triebel, F., et al., *LAG-3, a novel lymphocyte activation gene closely related to CD4*. J Exp Med, 1990. 171(5): p. 1393-405.
87. Triebel, F., *LAG-3: a regulator of T-cell and DC responses and its use in therapeutic vaccination*. Trends Immunol, 2003. 24(12): p. 619-22.
88. Chun, T., et al., *The effect of soluble LAG-3 (CD223) treatment in fetal thymic organ culture*. Biotechnol Lett, 2004. 26(17): p. 1371-7.
89. Okazaki, T., et al., *PD-1 and LAG-3 inhibitory co-receptors act synergistically to prevent autoimmunity in mice*. J Exp Med, 2011. 208(2): p. 395-407.
90. Sierro, S., P. Romero, and D. E. Speiser, *The CD4-like molecule LAG-3, biology and therapeutic applications*. Expert Opin Ther Targets, 2011. 15(1): p. 91-101.
91. Abeler-Dorner, L., et al., *Butyrophilins: an emerging family of immune regulators*. Trends Immunol, 2012. 33(1): p. 34-41.
92. Cubillos-Ruiz, J. R. and J. R. Conejo-Garcia, *It never rains but it pours: potential role of butyrophilins in inhibiting anti-tumor immune responses*. Cell Cycle, 2011. 10(3): p. 368-9.
93. Arnett, H. A., S. S. Escobar, and J. L. Viney, *Regulation of costimulation in the era of butyrophilins*. Cytokine, 2009. 46(3): p. 370-5.
94. Elleder, D., et al., *The receptor for the subgroup C avian sarcoma and leukosis viruses, Tvc, is related to mammalian butyrophilins, members of the immunoglobulin superfamily*. J Virol, 2005. 79(16): p. 10408-19.
95. Kuespert, K., S. Pils, and C. R. Hauck, *CEACAMs: their role in physiology and pathophysiology*. Curr Opin Cell Biol, 2006. 18(5): p. 565-71.
96. Barrow, A. D. and J. Trowsdale, *The extended human leukocyte receptor complex: diverse ways of modulating immune responses*. Immunol Rev, 2008. 224: p. 98-123.

97. Aslanidis, C. and P. J. de Jong, *Ligation-independent cloning of PCR products (LIC-PCR)*. Nucleic Acids Res, 1990. 18(20): p. 6069-74.
98. Bandaranayake, A. D., et al., *Daedalus: a robust, turnkey platform for rapid production of decigram quantities of active recombinant proteins in human cell lines using novel lentiviral vectors*. Nucleic Acids Res, 2011. 39(21): p. e143.
99. Lindquist, R. A., et al., *Genome-scale RNAi on living-cell microarrays identifies novel regulators of Drosophila melanogaster TORC1-S6K pathway signaling*. Genome Res, 2011. 21(3): p. 433-46.
100. Wheeler, D. B., et al., *RNAi living-cell microarrays for loss-of-function screens in Drosophila melanogaster cells*. Nat Methods, 2004. 1(2): p. 127-32.
101. Graham, F. L., *Growth of 293 cells in suspension culture*. J Gen Virol, 1987. 68 (Pt 3): p. 937-40.
102. Stegmayer, C., et al., *Direct transport across the plasma membrane of mammalian cells of Leishmania HASPB as revealed by a CHO export mutant*. J Cell Sci, 2005. 118(Pt 3): p. 517-27.
103. Grutzkau, A. and A. Radbruch, *Small but mighty: how the MACS-technology based on nanosized superparamagnetic particles has helped to analyze the immune system within the last 20 years*. Cytometry A, 2010. 77(7): p. 643-7.
104. Thudi, M., et al., *Current state-of-art of sequencing technologies for plant genomics research*. Brief Funct Genomics, 2012. 11(1): p. 3-11.
105. Koboldt, D. C., et al., *Massively parallel sequencing approaches for characterization of structural variation*. Methods Mol Biol, 2012. 838: p. 369-84.
106. Morozova, O. and M. A. Marra, *Applications of next-generation sequencing technologies in functional genomics*. Genomics, 2008. 92(5): p. 255-64.
107. Whitehead, T. A., et al., *Optimization of affinity, specificity and function of designed influenza inhibitors using deep sequencing*. Nat Biotechnol, 2012. 30(6): p. 543-8.
108. Smith, A. M., et al., *Competitive genomic screens of barcoded yeast libraries*. J Vis Exp, 2011(54).
109. Lee, W., et al., *Genome-wide requirements for resistance to functionally distinct DNA-damaging agents*. PLoS Genet, 2005. 1(2): p. e24.
110. Pierce, S. E., et al., *Genome-wide analysis of barcoded Saccharomyces cerevisiae gene-deletion mutants in pooled cultures*. Nat Protoc, 2007. 2(11): p. 2958-74.
111. McLellan, A. S., et al., *The Wasp System: An open source environment for managing and analyzing genomic data*. Genomics, 2012.
112. Golden, A., et al., *The Einstein Genome Gateway using WASP—a high throughput multi-layered life sciences portal for XSEDE*. Stud Health Technol Inform, 2012. 175: p. 182-91.
113. Jiang, L., et al., *Synthetic spike-in standards for RNA-seq experiments*. Genome Res, 2011. 21(9): p. 1543-51.

What is claimed is:

1. A variant programmed death-1 ligand (PD-L1) polypeptide, wherein:
    a) the variant PD-L1 polypeptide comprises an amino acid substitution selected from E60D and E60R, wherein the variant PD-L1 polypeptide exhibits:
   i) reduced binding affinity to PD-1 compared to wild-type PD-L1; and
   ii) reduced binding affinity to B7-1 compared to wild-type PD-L1; or b) the variant PD-L1 polypeptide comprises an amino acid substitution selected from I116D, I116R, G120A, G120R, A121R, A121D, and D122R, wherein the variant PD-L1 polypeptide exhibits:
   i) reduced binding affinity to PD-1 compared to wild-type PD-L1; and
   ii) reduced binding affinity to B7-1 compared to wild-type PD-L1.

2. The variant PD-L1 polypeptide of claim 1, wherein the variant PD-L1 polypeptide is immobilized on a solid support.

3. The variant PD-L1 polypeptide of claim 2, wherein solid support is a microbead.

4. A variant programmed death ligand-1 (PD-L1) polypeptide that binds specifically to PD-1, wherein said PD-L1 polypeptide contains an amino acid residue point mutation of Gly-119, wherein said point mutation is selected from G119A, G119D, and G119R wherein Gly-119 corresponds to residue 104 of SEQ ID NO:4.

5. A fusion polypeptide comprising:
A) a variant programmed death-1 ligand (PD-L1) polypeptide, wherein:
  a) the variant PD-L1 polypeptide comprises an amino acid substitution selected from D122A, Y123D, Y123R, Y123A, K124D, K124R, R125A, and R125D, wherein the variant PD-L1 polypeptide:
    i) exhibits reduced binding affinity to PD-1 compared to wild-type PD-L1; and
    ii) retains at least 40% of wild-type binding affinity to B7-1; or
  b) variant PD-L1 polypeptide comprises an amino acid substitution selected from E60D and E60R, wherein the variant PD-L1 polypeptide exhibits:
    i) reduced binding affinity to PD-1 compared to wild-type PD-L1; and
    ii) reduced binding affinity to B7-1 compared to wild-type PD-L1; or
  c) the variant PD-L1 polypeptide comprises an amino acid substitution selected from I116A, G119D, G119R, and G120D, wherein the variant PD-L1 polypeptide:
    i) retains at least 75% wild-type binding affinity to PD-L1; and
    ii) exhibits reduced binding affinity to B7-1 compared to wild-type PD-L1; or
  d) the variant PD-L1 polypeptide comprises an amino acid substitution selected from I116D, I116R, G120A, G120R, A121R, A121D, and D122R, wherein the variant PD-L1 polypeptide exhibits:
    i) reduced binding affinity to PD-1 compared to wild-type PD-L1; and
    ii) reduced binding affinity to B7-1 compared to wild-type PD-L1, wherein E60, I116, G119, G120, A121, D122, Y123, K124, and R125 correspond to amino acids E45, I101, G104, G105, A106, D107, Y108, K109, and R110 of the amino acid sequence set forth in SEQ ID NO:4; and
B) a fusion partner polypeptide.

6. The fusion polypeptide of claim 5, wherein the fusion partner polypeptide is a fluorescent polypeptide.

7. The fusion polypeptide of claim 5, wherein the fusion partner polypeptide is an immunoglobulin Fc polypeptide.

* * * * *

UNITED STATES PATENT AND TRADEMARK OFFICE
CERTIFICATE OF CORRECTION

PATENT NO. : 11,226,339 B2
APPLICATION NO. : 16/044608
DATED : January 18, 2022
INVENTOR(S) : Steven Almo et al.

It is certified that error appears in the above-identified patent and that said Letters Patent is hereby corrected as shown below:

In the Specification

Column 1, Line 62, replace "expres" with --- express ---

Column 7, Line 27, replace "7C0" with --- 7C ---

Signed and Sealed this
Fifth Day of July, 2022

Katherine Kelly Vidal
*Director of the United States Patent and Trademark Office*